US012305180B2

(12) United States Patent
Miranda et al.

(10) Patent No.: US 12,305,180 B2
(45) Date of Patent: May 20, 2025

(54) WHEAT TRANSGENIC EVENT IND-ØØ412-7

(71) Applicant: Bioceres LLC, Wilmington, DE (US)

(72) Inventors: Patricia Miranda, Sante Fe (AR); Martin Vazquez, Sante Fe (AR); Carlos Dezar, Sante Fe (AR); Francisco Ayala, Sante Fe (AR); Geronimo Watson, Sante Fe (AR)

(73) Assignee: BIOCERES LLC, Wilmington, DE (US)

( * ) Notice: Subject to any disclaimer, the term of this patent is extended or adjusted under 35 U.S.C. 154(b) by 306 days.

(21) Appl. No.: 17/795,343

(22) PCT Filed: Feb. 5, 2020

(86) PCT No.: PCT/US2020/016832
§ 371 (c)(1),
(2) Date: Jul. 26, 2022

(87) PCT Pub. No.: WO2021/158217
PCT Pub. Date: Aug. 12, 2021

(65) Prior Publication Data

US 2023/0075569 A1 Mar. 9, 2023

(51) Int. Cl.
*C12N 15/82* (2006.01)
*C07K 14/415* (2006.01)

(52) U.S. Cl.
CPC ........ *C12N 15/8271* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 6,121,521 | A | 9/2000 | Desai |
| 2013/0263327 | A1 | 10/2013 | Chan et al. |
| 2016/0130594 | A1 | 5/2016 | Kumar et al. |

FOREIGN PATENT DOCUMENTS

| | | | |
|---|---|---|---|
| AR | 090110 | A1 | 10/2014 |
| AR | 081216 | B2 | 5/2015 |

OTHER PUBLICATIONS

Ayala et al. Transgenic Res. 28:165-176. (Year: 2019).*
González et al. (Journal of Experimental Botany. 70(5): 1669-1681. (Year: 2019).*
Duque et al., "Abiotic Stress Responses in Plants: Unraveling the Complexity of Genes and Networks to Survive," Chapter 3: Abiotic Stress-Plant Responses and Applications in Agriculture (2013): pp. 49-101 (54 pages).
González et al., "Field-grown transgenic wheat expressing the sunflower gene HaHB4 significantly outyields the wild type," Journal of Experimental Botany, 2019, pp. 1669-1681, vol. 70, No. 5 (13 pages).
Sayed, "Chlorophyll fluorescence as a tool in cereal crop research," Photosynthetica, 2003, pp. 321-330, vol. 41, No. 3 (10 pages).
International Search Report (PCT/ISA/210) issued in PCT Application No. PCT/US20/16832 dated Jun. 22, 2020 (six (6) pages).
English-language Written Opinion (PCT/ISA/237) issued in PCT Application No. PCT/US20/16832 dated Jun. 22, 2020 (eight (8) pages).
GenBank Accession LR722619.1 . *Hordeum vulgars* subsp. vulgars genome assembly, chromosome: 4H. Oct. 10, 2019 [online]. [Retrieved Apr. 27, 2020). Retrieved from the internet:< URL: https://www.ncbi.nlm.nih.gov/nuccore/LR722619.1/ > Especially nt 60716-60912 and nt 80969-81222 (one (1) page).
GenBank Accession LS480641.1 . Triticum aestivum genome assembly, chromosome: II. Jun. 7, 2018 [online]. [Retrieved Apr. 27, 2020]. Retrieved from the internet <URL: https://www.ncbi.nlm.nih.gov/nuccore/LS480641 > Especially nt 2922266-2921965 and nt 2921205-2920682 (282 pages).
International Preliminary Report on Patentability (PCT/IB/326 & PCT/IB/373), including Written Opinion (PCT/ISA/237) issued in PCT Application No. PCT/US2020/016832 dated Aug. 18, 2022 (10 pages).

* cited by examiner

*Primary Examiner* — Mykola V. Kovalenko
*Assistant Examiner* — David R Byrnes
(74) *Attorney, Agent, or Firm* — Crowell & Moring LLP

(57) ABSTRACT

The present invention refers to a wheat plant, seed or part of it comprising event IND-ØØ412-7, a commodity product resulting from the seed, a recombinant DNA molecule comprised in event IND-ØØ412-7, DNA primers and probes useful for detecting event IND-ØØ412-7, DNA detection kit, method for producing a wheat plant tolerant to abiotic stresses and method for detecting the presence of DNA belonging to wheat event IND-ØØ412-7 in a sample.

2 Claims, 17 Drawing Sheets

Specification includes a Sequence Listing.

FIGURE 1
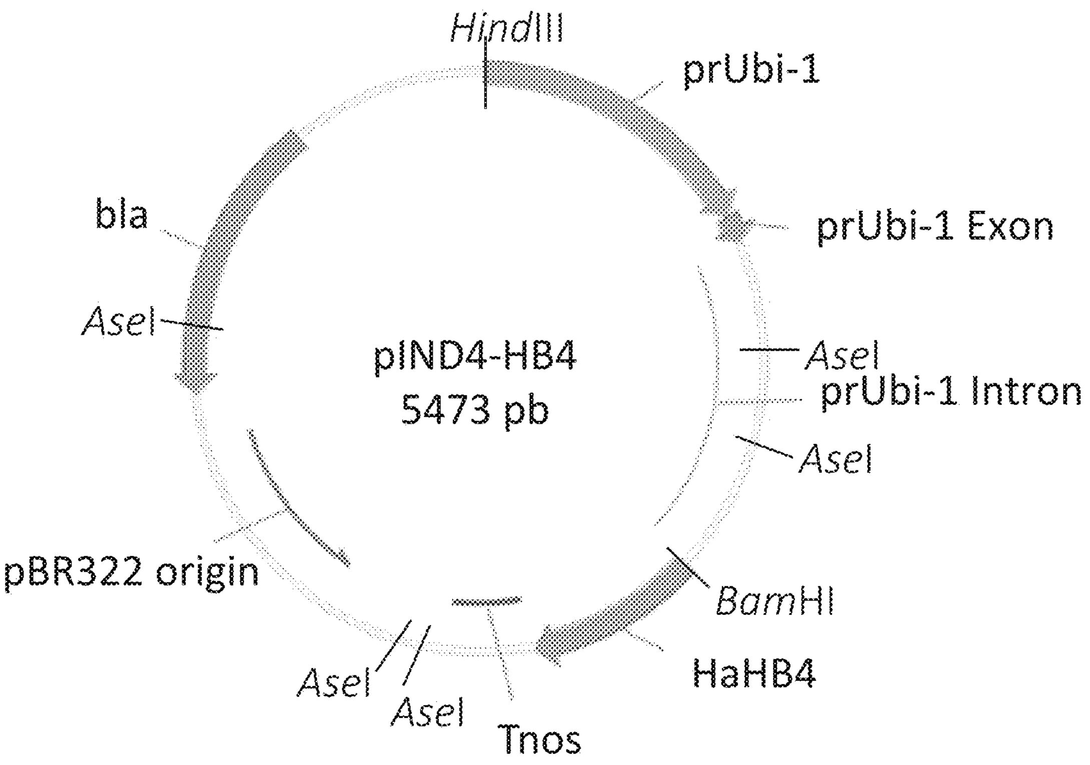
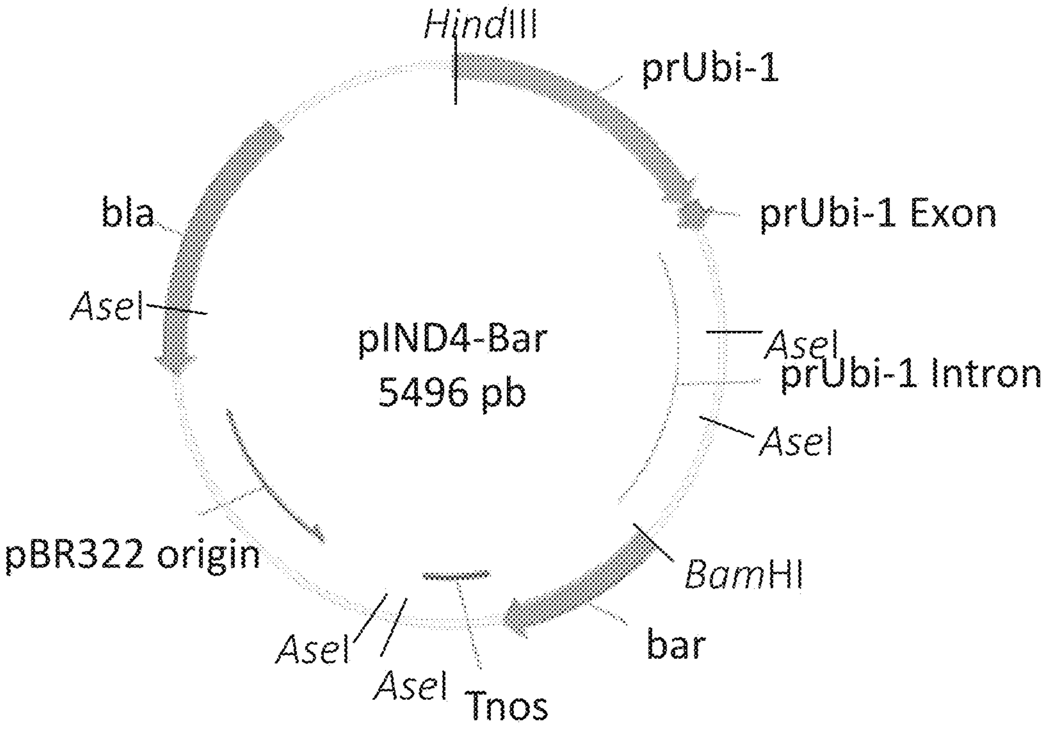

FIGURE 2

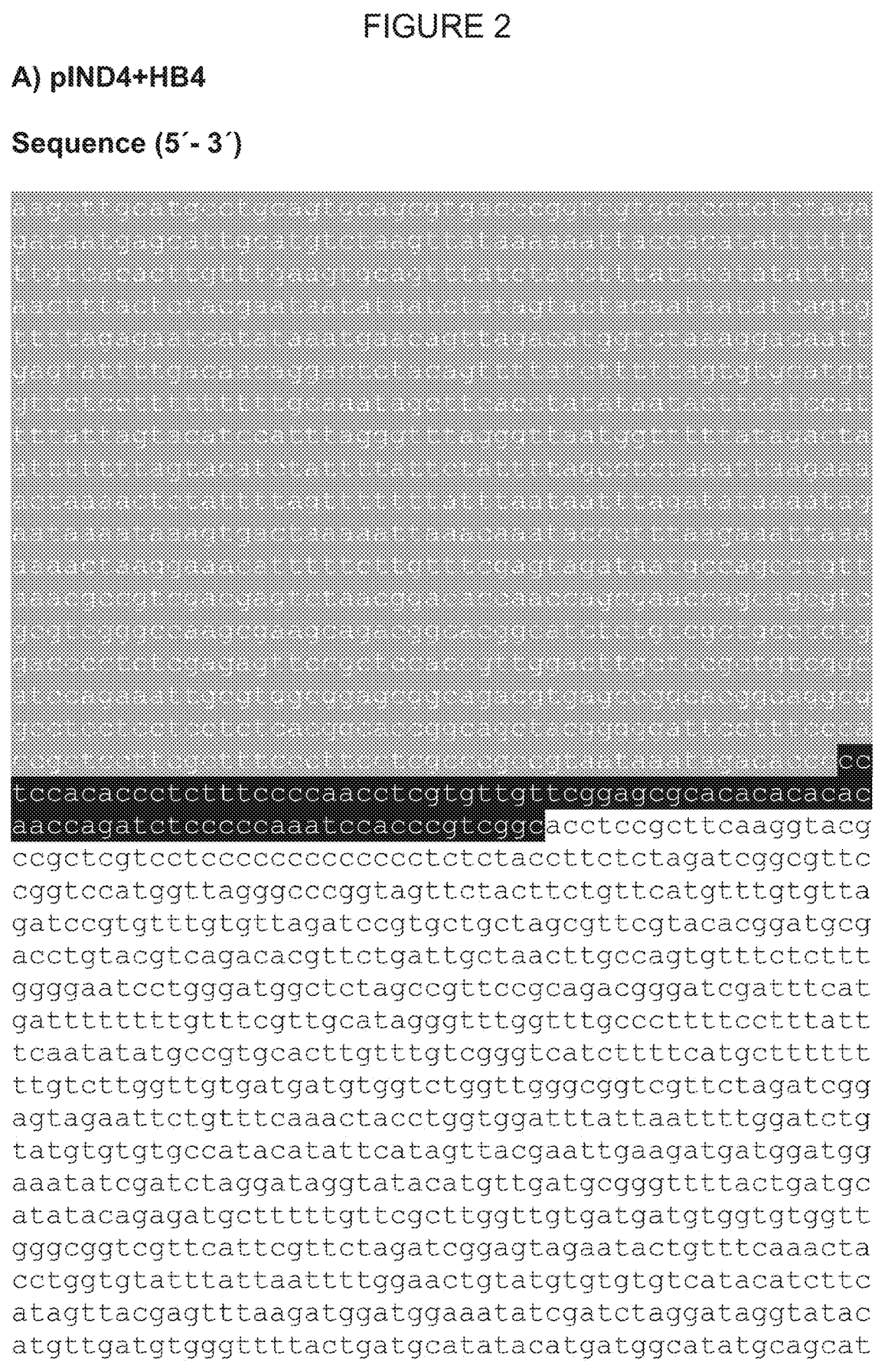

A) pIND4+HB4

Sequence (5´- 3´)

[illegible] cc
tccacaccctctttccccaacctcgtgttgttcggagcgcacacacacac
aaccagatctcccccaaatccacccgtcggcacctccgcttcaaggtacg
ccgctcgtcctccccccccccccctctctaccttctctagatcggcgttc
cggtccatggttagggcccggtagttctacttctgttcatgtttgtgtta
gatccgtgtttgtgttagatccgtgctgctagcgttcgtacacggatgcg
acctgtacgtcagacacgttctgattgctaacttgccagtgtttctcttt
ggggaatcctgggatggctctagccgttccgcagacgggatcgatttcat
gattttttttgtttcgttgcatagggtttggtttgcccttttcctttatt
tcaatatatgccgtgcacttgtttgtcgggtcatcttttcatgcttttt
ttgtcttggttgtgatgatgtggtctggttgggcggtcgttctagatcgg
agtagaattctgtttcaaactacctggtggatttattaattttggatctg
tatgtgtgtgccatacatattcatagttacgaattgaagatgatggatgg
aaatatcgatctaggataggtatacatgttgatgcgggttttactgatgc
atatacagagatgctttttgttcgcttggttgtgatgatgtggtgtggtt
gggcggtcgttcattcgttctagatcggagtagaatactgtttcaaacta
cctggtgtatttattaattttggaactgtatgtgtgtgtcatacatcttc
atagttacgagtttaagatggatggaaatatcgatctaggataggtatac
atgttgatgtgggttttactgatgcatatacatgatggcatatgcagcat

FIGURE 2 CONT.

ctattcatatgctctaaccttgagtacctatctattataataaacaagta
tgttttataattattttgatcttgatatacttggatgatggcatatgcag
cagctatatgtggatttttttagccctgccttcatacgctatttatttgc
ttggtactgtttcttttgtcgatgctcaccctgttgtttggtgttacttc
tgcaggtcgactctagaggatccgatccaccatgtctcttcaacaagtaa
caaccaccaggaagaaccgaaacgaggggcggagacgatttaccgacaaa
caaataagtttcctagagtacatgtttgagacacagtcgagacccgagtt
aaggatgaaacaccagttggcacataaactcgggcttcatcctcgtcaag
tggcgatatggttccagaacaaacgcgcgcgatcaaagtcgaggcagatt
gagcaagagtataacgcgctaaagcataactacgagacgcttgcgtctaa
atccgagtctctaaagaaagagaatcaggccctactcaatcaattggagg
tgctgagaaatgtagccgaaaagcatcaagagaaaactagtagtagtggc
agcggtgaagaatcggatgatcggtttacgaactctccggacgttatgtt
tggtcaagaaatgaatgttccgttttgcgacggttttgcgtaccttgaag
aaggaaacagtttgttggagattgaagaacaactgccagaccttcaaaag
tggtgggagttctaagagctcgaatttccccgatcgttcaaacatttggc
aataaagtttcttaagattgaatcctgttgccggtcttgcgatgattatc
atataatttctgttgaattacgttaagcatgtaataattaacatgtaatg
catgacgttatttatgagatgggtttttatgattagagtcccgcaattat
acatttaatacgcgatagaaaacaaaatatagcgcgcaaactaggataaa
ttatcgcgcgcggtgtcatctatgttactagatcggaattcgtaatcatg
gtcatagctgtttcctgtgtgaaattgttatccgctcacaattccacaca
acatacgagccggaagcataaagtgtaaagcctggggtgcctaatgagtg
agctaactcacattaattgcgttgcgctcactgcccgctttccagtcggg
aaacctgtcgtgccagctgcattaatgaatcggccaacgcgcggggagag
gcggtttgcgtattgggcgctcttccgcttcctcgctcactgactcgctg
cgctcggtcgttcggctgcggcgagcggtatcagctcactcaaaggcggt
aatacggttatccacagaatcaggggataacgcaggaaagaacatgtgag
caaaaggccagcaaaaggccaggaaccgtaaaaaggccgcgttgctggcg
tttttccataggctccgcccccctgacgagcatcacaaaaatcgacgctc
aagtcagaggtggcgaaacccgacaggactataaagataccaggcgtttc
cccctggaagctccctcgtgcgctctcctgttccgaccctgccgcttacc
ggatacctgtccgcctttctcccttcgggaagcgtggcgctttctcatag
ctcacgctgtaggtatctcagttcggtgtaggtcgttcgctccaagctgg
gctgtgtgcacgaaccccccgttcagcccgaccgctgcgccttatccggt
aactatcgtcttgagtccaacccggtaagacacgacttatcgccactggc
agcagccactggtaacaggattagcagagcgaggtatgtaggcggtgcta
cagagttcttgaagtggtggcctaactacggctacactagaaggacagta
tttggtatctgcgctctgctgaagccagttaccttcggaaaaagagttgg
tagctcttgatccggcaaacaaaccaccgctggtagcggtggtttttttg

FIGURE 2 CONT.

tttgcaagcagcagattacgcgcagaaaaaaaggatctcaagaagatcct
ttgatcttttctacggggtctgacgctcagtggaacgaaaactcacgtta
agggattttggtcatgagattatcaaaaaggatcttcacctagatccttt
taaattaaaaatgaagttttaaatcaatctaaagtatatatgagtaaact
tggtctgacagttaccaatgcttaatcagtgaggcacctatctcagcgat
ctgtctatttcgttcatccatagttgcctgactccccgtcgtgtagataa
ctacgatacgggagggcttaccatctggccccagtgctgcaatgataccg
cgagacccacgctcaccggctccagatttatcagcaataaaccagccagc
cggaagggccgagcgcagaagtggtcctgcaactttatccgcctccatcc
agtctattaattgttgccgggaagctagagtaagtagttcgccagttaat
agtttgcgcaacgttgttgccattgctacaggcatcgtggtgtcacgctc
gtcgtttggtatggcttcattcagctccggttcccaacgatcaaggcgag
ttacatgatcccccatgttgtgcaaaaaagcggttagctccttcggtcct
ccgatcgttgtcagaagtaagttggccgcagtgttatcactcatggttat
ggcagcactgcataattctcttactgtcatgccatccgtaagatgctttt
ctgtgactggtgagtactcaaccaagtcattctgagaatagtgtatgcgg
cgaccgagttgctcttgcccggcgtcaatacgggataataccgcgccaca
tagcagaactttaaaagtgctcatcattggaaaacgttcttcggggcgaa
aactctcaaggatcttaccgctgttgagatccagttcgatgtaacccact
cgtgcacccaactgatcttcagcatcttttactttcaccagcgtttctgg
gtgagcaaaaacaggaaggcaaaatgccgcaaaaaagggaataagggcga
cacggaaatgttgaatactcatactcttcctttttcaatattattgaagc
atttatcagggttattgtctcatgagcggatacatatttgaatgtattta
gaaaaataaacaaataggggttccgcgcacatttccccgaaaagtgccac
ctgacgtctaagaaaccattattatcatgacattaacctataaaaatagg
cgtatcacgaggccctttcgtctcgcgcgtttcggtgatgacggtgaaaa
cctctgacacatgcagctcccggagacggtcacagcttgtctgtaagcgg
atgccgggagcagacaagcccgtcagggcgcgtcagcgggtgttggcggg
tgtcggggctggcttaactatgcggcatcagagcagattgtactgagagt
gcaccatatgcggtgtgaaataccgcacagatgcgtaaggagaaaatacc
gcatcaggcgccattcgccattcaggctgcgcaactgttgggaagggcga
tcggtgcgggcctcttcgctattacgccagctggcgaaagggggatgtgc
tgcaaggcgattaagttgggtaacgccagggttttcccagtcacgacgtt
gtaaaacgacggccagtgcc Exon Ubi 1 Intrón HAHB4 Tnos

FIGURE 2 CONT.

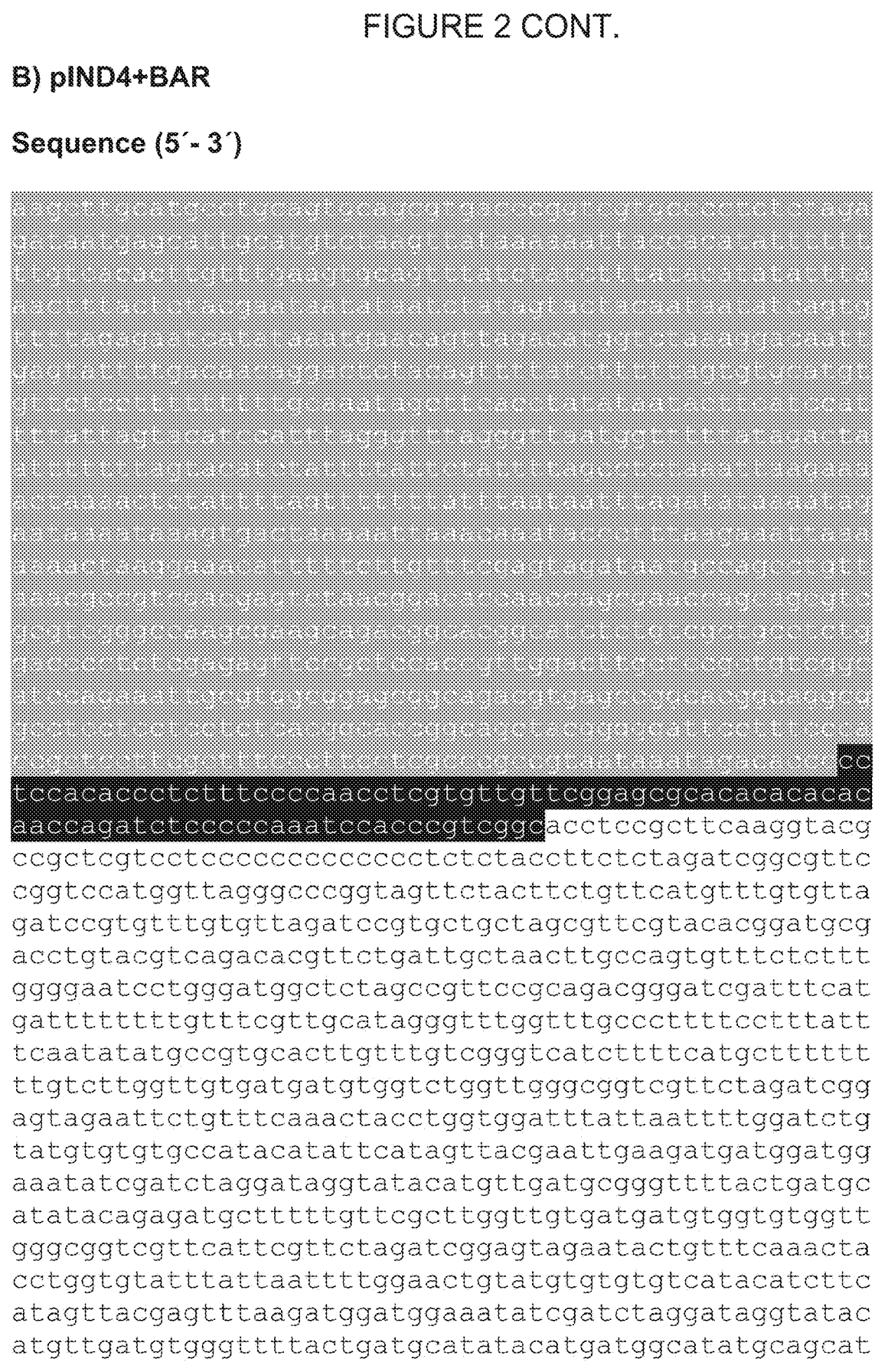

B) pIND4+BAR

Sequence (5´- 3´)

[illegible]cc
tccacaccctctttccccaacctcgtgttgttcggagcgcacacacacac
aaccagatctcccccaaatccacccgtcggcacctccgcttcaaggtacg
ccgctcgtcctcccccccccccctctctaccttctctagatcggcgttc
cggtccatggttagggcccggtagttctacttctgttcatgtttgtgtta
gatccgtgtttgtgttagatccgtgctgctagcgttcgtacacggatgcg
acctgtacgtcagacacgttctgattgctaacttgccagtgtttctcttt
ggggaatcctgggatggctctagccgttccgcagacgggatcgatttcat
gattttttttgtttcgttgcatagggtttggtttgcccttttcctttatt
tcaatatatgccgtgcacttgtttgtcgggtcatcttttcatgcttttt
ttgtcttggttgtgatgatgtggtctggttgggcggtcgttctagatcgg
agtagaattctgtttcaaactacctggtggatttattaattttggatctg
tatgtgtgtgccatacatattcatagttacgaattgaagatgatggatgg
aaatatcgatctaggataggtatacatgttgatgcgggttttactgatgc
atatacagagatgcttttttgttcgcttggttgtgatgatgtggtgtggtt
gggcggtcgttcattcgttctagatcggagtagaatactgtttcaaacta
cctggtgtatttattaattttggaactgtatgtgtgtgtcatacatcttc
atagttacgagtttaagatggatggaaatatcgatctaggataggtatac
atgttgatgtgggttttactgatgcatatacatgatggcatatgcagcat

FIGURE 2 CONT.

ctattcatatgctctaaccttgagtacctatctattataataaacaagta
tgttttataattattttgatcttgatatacttggatgatggcatatgcag
cagctatatgtggatttttttagccctgccttcatacgctatttatttgc
ttggtactgtttcttttgtcgatgctcaccctgttgtttggtgttacttc
tgcaggtcgactctagaggatccatcgattaggaagtaaccatgagccca
gaacgacgcccggccgacatccgccgtgccaccgaggcggacatgccggc
ggtctgcaccatcgtcaaccactacatcgagacaagcacggtcaacttcc
gtaccgagccgcaggaaccgcaggagtggacggacgacctcgtccgtctg
cgggagcgctatccctggctcgtcgccgaggtggacggcgaggtcgccgg
catcgcctacgcgggcccctggaaggcacgcaacgcctacgactggacgg
ccgagtcgaccgtgtacgtctcccccgccaccagcggacgggactgggc
tccacgctctacacccacctgctgaagtccctggaggcacagggcttcaa
gagcgtggtcgctgtcatcgggctgcccaacgacccgagcgtgcgcatgc
acgaggcgctcggatatgccccccgcggcatgctgcgggcggccggcttc
aagcacgggaactggcatgacgtgggtttctggcagctggacttcagcct
gccggtaccgccccgtccggtcctgcccgtcaccgagatctgatccgtcg
acctgcagatcgttcaaacatttggcaataaagtttcttaagattgaatc
ctgttgccggtcttgcgatgattatcatataatttctgttgaattacgtt
aagcatgtaataattaacatgtaatgcatgacgttatttatgagatgggt
ttttatgattagagtcccgcaattatacatttaatacgcgatagaaaaca
aaatatagcgcgcaaactaggataaattatcgcgcgcggtgtcatctatg
ttactagatcggaattcgtaatcatggtcatagctgtttcctgtgtgaaa
ttgttatccgctcacaattccacacaacatacgagccggaagcataaagt
gtaaagcctggggtgcctaatgagtgagctaactcacattaattgcgttg
cgctcactgcccgctttccagtcgggaaacctgtcgtgccagctgcatta
atgaatcggccaacgcgcggggagaggcggtttgcgtattgggcgctctt
ccgcttcctcgctcactgactcgctgcgctcggtcgttcggctgcggcga
gcggtatcagctcactcaaaggcggtaatacggttatccacagaatcagg
ggataacgcaggaaagaacatgtgagcaaaaggccagcaaaaggccagga
accgtaaaaaggccgcgttgctggcgtttttccataggctccgcccccct
gacgagcatcacaaaaatcgacgctcaagtcagaggtggcgaaacccgac
aggactataaagataccaggcgtttccccctggaagctccctcgtgcgct
ctcctgttccgaccctgccgcttaccggatacctgtccgcctttctccct
tcgggaagcgtggcgctttctcatagctcacgctgtaggtatctcagttc
ggtgtaggtcgttcgctccaagctgggctgtgtgcacgaaccccccgttc
agcccgaccgctgcgccttatccggtaactatcgtcttgagtccaacccg
gtaagacacgacttatcgccactggcagcagccactggtaacaggattag
cagagcgaggtatgtaggcggtgctacagagttcttgaagtggtggccta
actacggctacactagaaggacagtatttggtatctgcgctctgctgaag
ccagttaccttcggaaaaagagttggtagctcttgatccggcaaacaaac

FIGURE 2 CONT.

caccgctggtagcggtggtttttttgtttgcaagcagcagattacgcgca
gaaaaaaaggatctcaagaagatcctttgatcttttctacggggtctgac
gctcagtggaacgaaaactcacgttaagggattttggtcatgagattatc
aaaaaggatcttcacctagatccttttaaattaaaaatgaagttttaaat
caatctaaagtatatatgagtaaacttggtctgacagttaccaatgctta
atcagtgaggcacctatctcagcgatctgtctatttcgttcatccatagt
tgcctgactccccgtcgtgtagataactacgatacgggagggcttaccat
ctggccccagtgctgcaatgataccgcgagacccacgctcaccggctcca
gatttatcagcaataaaccagccagccggaagggccgagcgcagaagtgg
tcctgcaactttatccgcctccatccagtctattaattgttgccgggaag
ctagagtaagtagttcgccagttaatagtttgcgcaacgttgttgccatt
gctacaggcatcgtggtgtcacgctcgtcgtttggtatggcttcattcag
ctccggttcccaacgatcaaggcgagttacatgatcccccatgttgtgca
aaaaagcggttagctccttcggtcctccgatcgttgtcagaagtaagttg
gccgcagtgttatcactcatggttatggcagcactgcataattctcttac
tgtcatgccatccgtaagatgcttttctgtgactggtgagtactcaacca
agtcattctgagaatagtgtatgcggcgaccgagttgctcttgcccggcg
tcaatacgggataataccgcgccacatagcagaactttaaaagtgctcat
cattggaaaacgttcttcggggcgaaaactctcaaggatcttaccgctgt
tgagatccagttcgatgtaacccactcgtgcacccaactgatcttcagca
tcttttactttcaccagcgtttctgggtgagcaaaaacaggaaggcaaaa
tgccgcaaaaaagggaataagggcgacacggaaatgttgaatactcatac
tcttcctttttcaatattattgaagcatttatcagggttattgtctcatg
agcggatacatatttgaatgtatttagaaaaataaacaaataggggttcc
gcgcacatttccccgaaaagtgccacctgacgtctaagaaaccattatta
tcatgacattaacctataaaaataggcgtatcacgaggccctttcgtctc
gcgcgtttcggtgatgacggtgaaaacctctgacacatgcagctcccgga
gacggtcacagcttgtctgtaagcggatgccgggagcagacaagcccgtc
agggcgcgtcagcgggtgttggcgggtgtcggggctggcttaactatgcg
gcatcagagcagattgtactgagagtgcaccatatgcggtgtgaaatacc
gcacagatgcgtaaggagaaaataccgcatcaggcgccattcgccattca
ggctgcgcaactgttgggaagggcgatcggtgcgggcctcttcgctatta
cgccagctggcgaaagggggatgtgctgcaaggcgattaagttgggtaac
gccagggttttcccagtcacgacgttgtaaaacgacggccagtgcc Exon Ubi 1 Intrón HAHB4 Tnos

FIGURE 3

```
>JPLa
  1 taatggtgagtgtatgcgcttgcgtctgtattgtgtttaaaaactcattctaagaaact  60
 61 cgtcatacagtgtccaccgtcaaggagccatctagtagggtgtggatgggcatgtgacag 120
121 gaaccttgtcgtgtgcacgttgtatgtcggtcttgttcaatatgtcgtctgtttcctcgg 180
181 cttacatgctcttttacgtgtcgtgcacccaactgatcttcagcatcttttactttcacc 240
241 agcgtttctgggtgagcaaaaacaggaaggcaaaatgccgcaaaaaagggaataagggcg 300
  1 Wheat Chr 2D 200
201 bla (i)      300

>JPLb
47227 [illegible] 47286
47287 [illegible]gtcgactctagaggtccctc47346
47347 gaccatggctgtaaggtcgccgaatacaagggcatgggtggcgaggcctaagaggagtat 47406
47407 aatttcttagacatttgtcaattataaacttcttggtaaaagagcatgtaagccgaggaa 47466
47467 acagacgacatattgaacaagaccgacatacaacgtgcacacgacaaggttcctgtcaca 47526
47527 tgcccatccacaccctactagatggctccttgacggtggacactgtatgacgagtttctt 47586
47587 agaatgagtttttaaacacaatac                                     47611
47227 prUbi-1 (i) 47326
47327 Wheat Chr 2D 47611

>JPSa
  1 gagcgcgctttcctatttaggatccaaattggcactgatactaaactgcttagacgaatc  60
 61 gcctggagtaaaatcaacaagctcggtttcagcagccgacttaaacttcatcgccgggtc 120
121 atgctcggtggttggcttctttagagacgtcatatccgccaggtcaacattattttgata 180
181 aaaattcatctcctctgccgcacaaacagactcagcataagccgcatcgccttcttcaca 240
241 ttctagggctacctttcgactcccattgagggagtcccggattaggggtgtttggaaca 300
301 ccacgatgcctgtagcaatggcaacaacgttgcgcaaactattaactggcgaactactta 360
361 ctctagcttcccggtaacaattaatagactgg                             392
  1 Wheat Chr 2D 292
293 bla (i)392

>JPSb
19791 ccaccgttggacttgctccctttattttattctattttatatctaaattattaaataaaa 19850
19851                                         gtcccgaacagtgtcctgga19910
19911 ggccgcacacgcttcggccccgaccctcgattcggagcccgctgcgttcgttgaggaaga19970
19971 acgattggacgtcacctcagaggctgcgacattaaaggcggtcgagtcgaacgccgaccc20030
20031 cgcactccgcgctgcccattactccgaggagccggattcttctccggcctccgggccttc20090
20091 catgcccctgccgaccgaatccgattgggcacctgtaatggagttcaccgccgcggacat20150
20151 ctttcagtgttcacctttcagtgacatcctgaattatctcaagtctctctctttatcagg20210
20211 agagcccaggccggattatggtctgcgaggttgggattcggacgatgaagaaattcaaag20270
20271 cccacccaccacccacttaatagccactgtcgacgatttaaccgacatgctcgacttcgg 20330
20331 ctccgaagacttcgacggtatggacgacgaaggaggagacgaaccggaaccagcacccac 20390
20391 agggcactggatatccaccacacacaat20418
47227 prUbi-1 (i) 47326
19891 Wheat Chr 2D20418
```

Wheat Chr 2D | prUbi-1 (i) | [illegible] | bla (i)

FIGURE 5
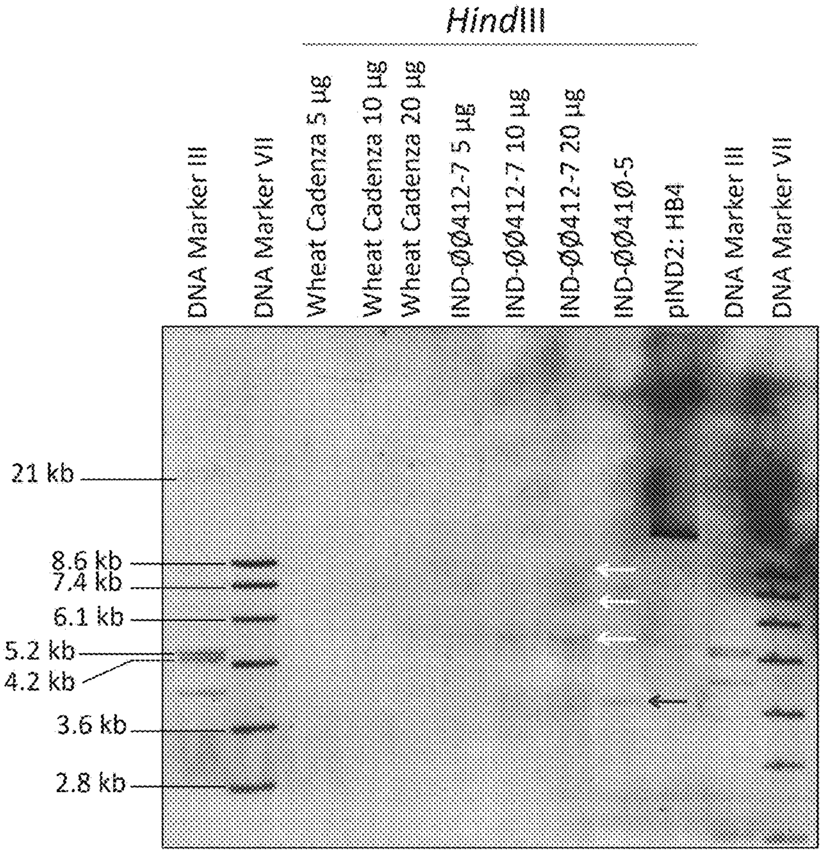
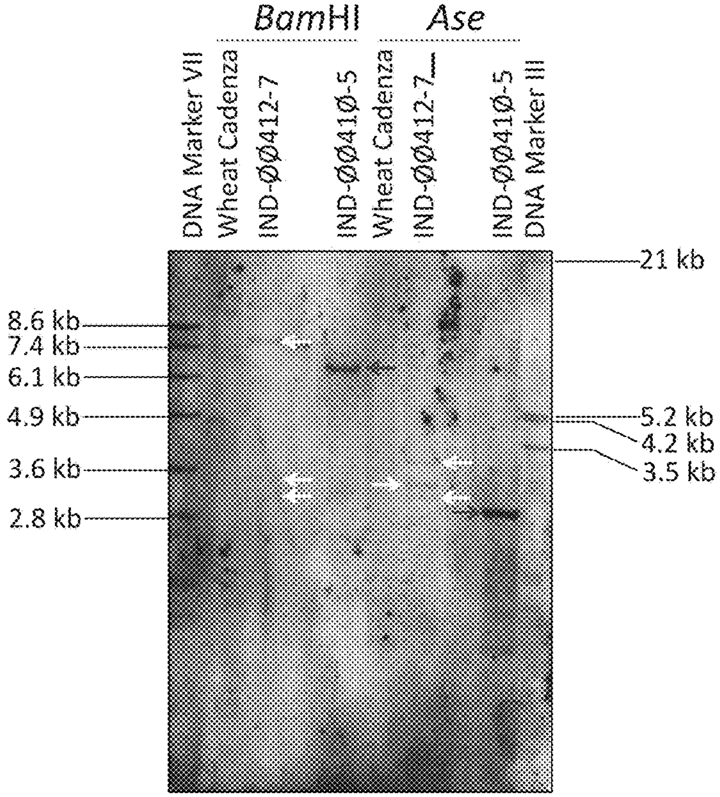

FIGURE 6
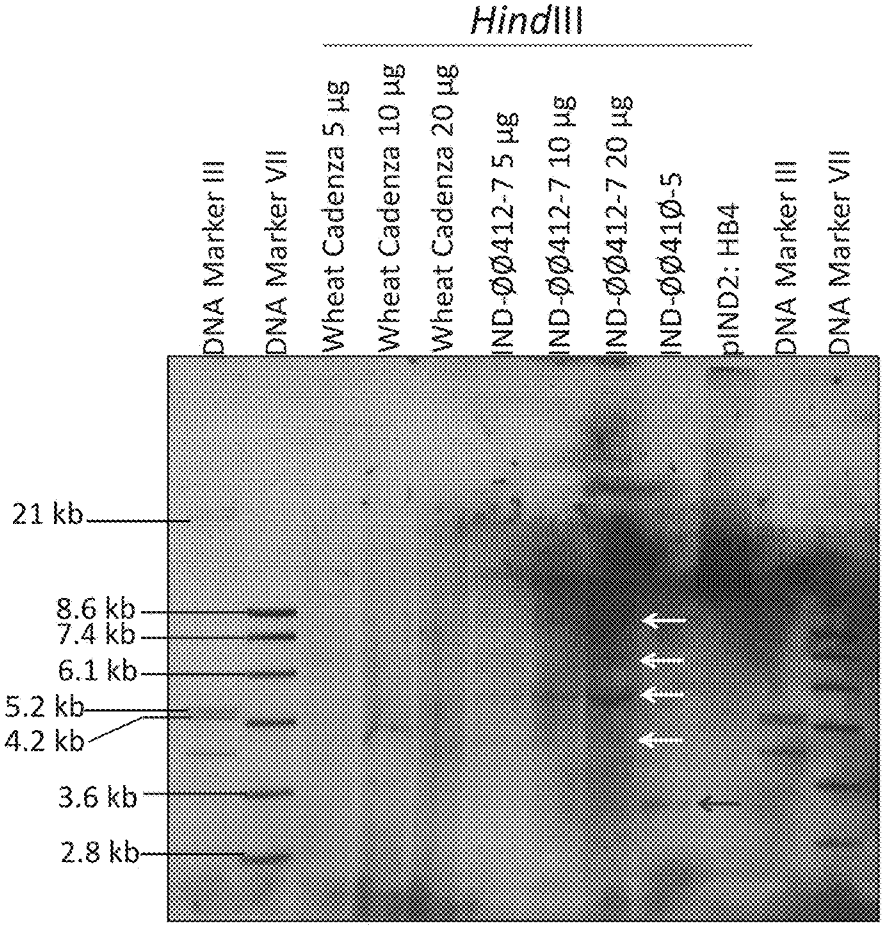
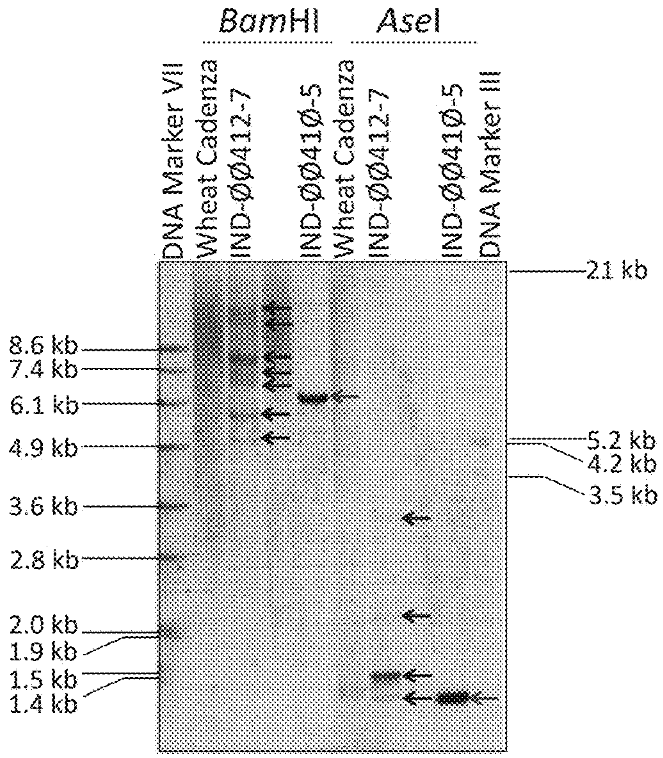

| Peak | Size (bp) | Conc. (ng/uL) | Rel. Conc. % | Molarity (nmole/L) | From (bp) | CV% |
|---|---|---|---|---|---|---|
| 1 | 1 (LM) | 1.6397 | | 2142.610 | 0 | 311.79 |
| 2 | 5951 | 28.5610 | 87.3 | 7.902 | 992 | 48.19 |
| 3 | 20000 | 4.1586 | 12.7 | 0.342 | 20000 | 15.66 |

FIGURE 9
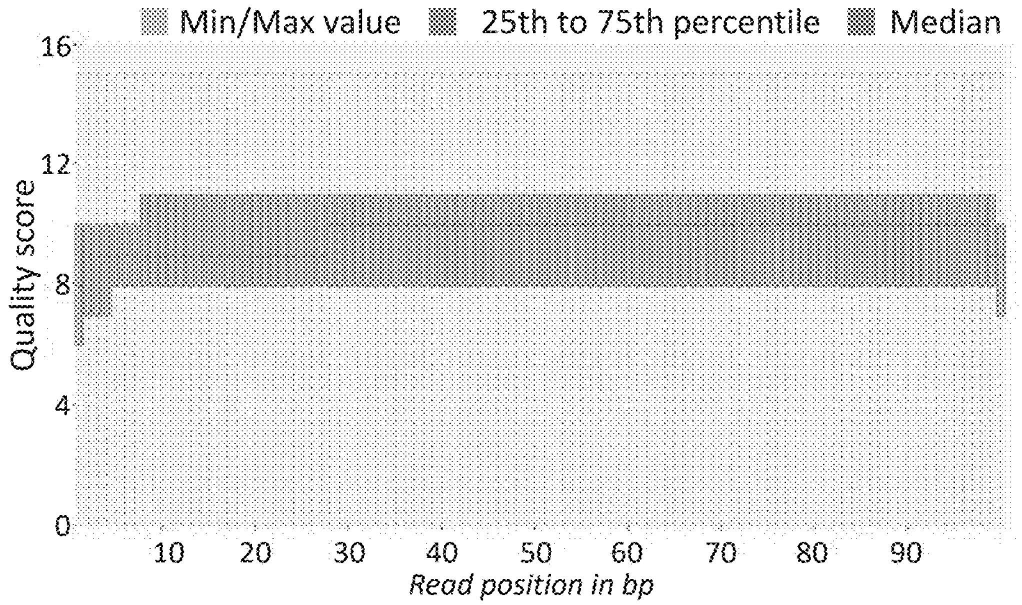
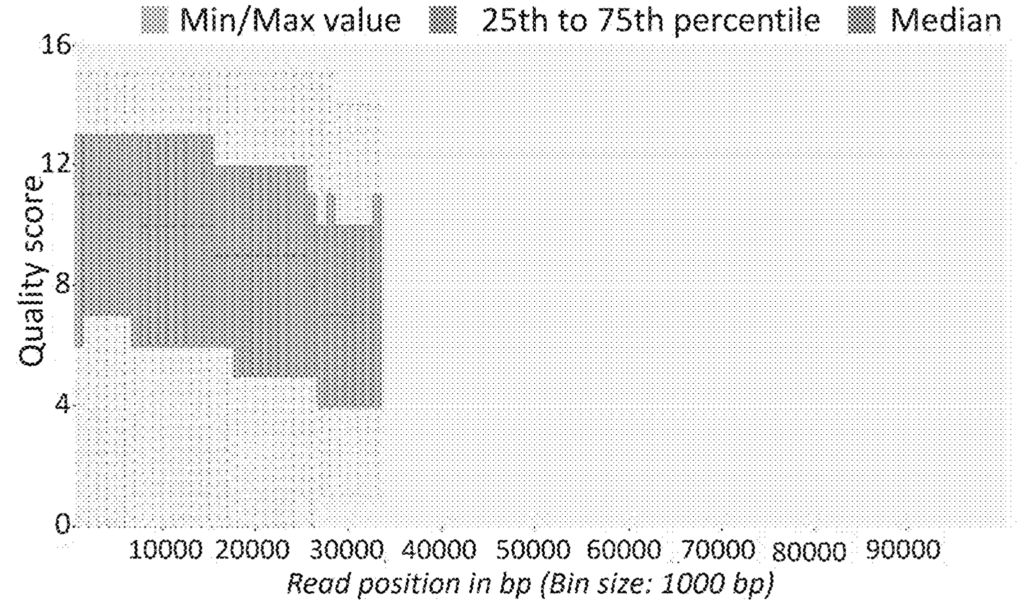

SEQUENCE LISTING

<160> NUMBER OF SEQ ID NOS: 14

<210> SEQ ID NO 1
<211> LENGTH: 47126
<212> TYPE: DNA
<213> ORGANISM: Artificial Sequence
<220> FEATURE:
<223> OTHER INFORMATION: Long insert without flanking regions

<400> SEQUENCE: 1
tcgtgcaccc aactgatctt cagcatcttt tactttcacc agcgtttctg ggtgagcaaa 60
aacaggaagg caaaatgccg caaaaaaggg aataagggcg acacggaaat gttgaatact 120
catactcttc ctttttcaat attattgaag catttatcag ggttattgtc tcatgagcgg 180
atacatattt gaatgtattt agaaaaataa acaaataggg gttccgcgca catttccccg 240
aaaagtgcca cctgacgtct aagaaaccat tattatcatg acattaacct ataaaaatag 300
gcgtatcacg aggccctttc gtctcgcgcg tttcggtgat gacggtgaaa acctctgaca 360
catgcagctc ccggagacgg tcacagcttg tctgtaagcg gatgccggga gcagacaagc 420

```
ccgtcagggc gcgtcagcgg gtgttggcgg gtgtcggggc tggcttaact atgcggcatc    480
agagcagatt gtactgagag tgcaccatat gcggtgtgaa ataccgcaca gatgcgtaag    540
gagaaaatac cgcatcaggc gccattcgcc attcaggctg cgcaactgtt gggaagggcg    600
atcggtgcgg gcctcttcgc tattacgcca gctggcgaaa gggggatgtg ctgcaaggcg    660
attaagttgg gtaacgccag ggttttccca gtcacgacgt tgtaaaacga cggccagtgc    720
caagcttgca tgcctgcagt gcagcgtgac ccggtcgtgc ccctctctag agataatgag    780
cattgcatgt ctaagttata aaaaattacc acatattttt tttgtcacac ttgtttgaag    840
tgcagtttat ctatctttat acatatattt aaactttact ctacgaataa tataatctat    900
agtactacaa taatatcagt gttttagaga atcatataaa tgaacagtta gacatggtct    960
aaaggacaat tgagtatttt gacaacagga ctctacagtt ttatcttttt agtgtgcatg   1020
tgttctcctt tttttttgca aatagcttca cctatataat acttcatcca ttttattagt   1080
acatccattt agggtttagg gttaatggtt tttatagact aatttttta gtacatctat   1140
tttattctat tttagcctct aaattaagaa aactaaaact ctattttagt tttttattt   1200
aataatttag atataaaata gaataaaata aagtgactaa aaattaaaca aatacccttt   1260
aagaaattaa aaaaactaag gaaacatttt tcttgtttcg agtagataat gccagcctgt   1320
taaacgccgt cgacgagtct aacggacacc aaccagcgaa ccagcagcgt cgcgtcgggc   1380
caagcgaagc agacggcacg gcatctctgt cgctgcctct ggacccctct cgagagttcc   1440
gctccaccgt tggacttgct ccgctgtcgg catccagaaa ttgcgtggcg gagcggcaga   1500
cgtgagccgg cacggcaggc ggcctcctcc tcctctcacg gcaccggcag ctacggggga   1560
ttcctttccc accgctcctt cgctttccct tcctcgcccg ccgtaataaa tagacacccc   1620
ctccacaccc tctttcccca acctcgtgtt gttcggagcg cacacacaca caaccagatc   1680
tcccccaaat ccacccgtcg gcgtacgccg ctcgtcctcc cccccccccc ctctctacct   1740
tctctagatc ggcgttccgg tccatggtta gggcccggta gttctacttc tgttcatgtt   1800
tgtgttagat ccgtgtttgt gttagatccg tgctgctagc gttcgtacac ggatgcgacc   1860
tgtacgtcag acacgtaacg tccggagagt tcgtaaaccg atcatccgat tcttcaccgc   1920
tgccactact actagttttc tcttgatgct tttcggctac atttctcagc acctccaatt   1980
gattgagtag ggcctgattc tctttcttta gagactcgga tttagacgca agcgtctcgt   2040
agttatgctt tagcgcgtta tactcttgct caatctgcct cgactttgat cgcgcgcgtt   2100
tgttctggaa ccatatcgcc acttgacgag gatgaagccc gagtttatgt gccaactggt   2160
gtttcatcct taactcgggt ctcgactgtg tctcaaacat gtactctagg aaacttattt   2220
gtttgtcggt aaatcgtctc cgcccctcgt ttcggttctt cctggtggtt gttacttgtt   2280
gaagagacat ggatccgggt gtgatcctct atagtcgacc tgcagaagta acaccaaaca   2340
acagggtgag catcgacaaa agaaacagta ccaagcaaat aaatagcgta tgaaggcagg   2400
gctaaaaaaa tccacatata gctgctgcat atgccatcat ccaagtatat caagatcaaa   2460
ataattataa aacatacttg tttattataa tagataggta ctcaaggtta gagcatatga   2520
atagatgctg catatgccat catgtatatg catcagtaaa acccacatca acatgtatac   2580
ctatcctaga tcgatatttc catccatctt aaactcgtaa ctatgaagat gtatgacaca   2640
cacatacagt tccaaaatta ataaatacac caggtagttt gaaacagtat tctactccga   2700
tctagaacga atgaacgacc gcccaaccac accacatcat cacaaccaag cgaacaaaaa   2760
gcatctctgt atatgcatca gtaaaacccg catcaacatg tatacctatc ctagatcgat   2820
```

-continued

```
atttccatcc atcatcttca attcgtaact atgaatatgt atggcacaca catacagatc   2880
caaaattaat aaatccacca ggtagtttga aacagaattg gaattcgtaa tcatggtcat   2940
agctgtttcc tgtgtgaaat tgttatccgc tcacaattcc acacaacata cgagccggaa   3000
gcataaagtg taaagcctgg ggtgcctaat gagtgagcta actcacatta attgcgttgc   3060
gctcactgcc cgctttccag tcgggaaacc tgtcgtgcca gctgcattaa tgaatcggcc   3120
aacgcgcggg gagaggcggt ttgcgtattg ggcgctcttc cgcttcctcg ctcactgact   3180
cgctgcgctc ggtcgttcgg ctgcggcgag cggtatcagc tcactcaaag gcggtaatac   3240
ggttatccac agaatcaggg gataacgcag gaaagaacat gtgagcaaaa ggccagcaaa   3300
aggccaggaa ccgtaaaaag gccgcgttgc tggcgttttt ccataggctc cgcccccctg   3360
acgagcatca caaaaatcga cgctcaagtc agaggtggcg aaacccgaca ggactataaa   3420
gataccaggc gtttccccct ggaagctccc tcgtgcgctc tcctgttccg accctgccgc   3480
ttaccggata cctgtccgcc tttctccctt cgggaagcgt ggcgctttct catagctcac   3540
gctgtaggta tctcagttcg gtgtaggtcg ttcgctccaa gctgggctgt gtgcacgaac   3600
cccccgttca gcccgaccgc tgcgccttat ccggtaacta tcgtcttgag tccaacccgg   3660
taagacacga cttatcgcca ctggcagcag ccactggtaa caggattagc agagcgaggt   3720
atgtaggcgg tgctacagag ttcttgaagt ggtggcctaa ctacggctac actagaagga   3780
cagtatttgg tatctgcgct ctgctgaagc cagttacctt cggaaaaaga gttggtagct   3840
cttgatccgg caaacaaacc accgctggta gcggtggttt ttttgtttgc aagcagcaga   3900
ttacgcgcag aaaaaaagga tctcaagaag atcctttgat cttttctacg gggtctgacg   3960
ctcagtggaa cgaaaactca cgttaaggga ttttggtcat gagattatca aaaaggatct   4020
tcacctagat ccttttaaat taaaaatgaa gttttaaatc aatctaaagt atatatgagt   4080
aaacttggtc tgacagtttt caaatatgta tccgctcatg agacaataac cctgataaat   4140
gcttcaataa tattgaaaaa ggaagagtat gagtattcaa catttccgtg tcgcccttat   4200
tccctttttt gcggcatttt gccttcctgt ttttgctcac ccagaaacgc tggtgaaagt   4260
aaaagatgct gaagatcagt tgggtgcacg agtgggttac atcgaactgg atctcaacag   4320
cggtaagatc cttgagagtt ttcgccccga agaacgtttt ccaatgatga gcacttttaa   4380
agttctgcta tgtggcgcgg tattatcccg tattgacgcc gggcaagagc aactcggtcg   4440
ccgcatacac tattctcaga atgacttggt tgagtactca ccagtcacag aaaagcatct   4500
tacggatggc atgacagtaa gagaattatg cagtgctgcc ataaccatga gtgataacac   4560
tgcggccaac ttacttctga caacgatcgg aggaccgaag gagctaaccg cttttttgca   4620
caacatgggg gatcatgtaa ctcgccttga tcgttgggaa ccggagctga atgaagccat   4680
accaaacgac gagcgtgaca ccacgatgcc tgtagcaatg gcaacaacgt tgcgcaaact   4740
attaactggc gaactactta ctctagcttc ccggcaacaa ttaatagact ggatggaggc   4800
ggataaagtt gcaggaccac ttctgcgctc ggcccttccg gctggctggt ttattgctga   4860
taaatctgga gccggtgagc gtgggtctcg cggtatcatt gcagcactgg ggccagatgg   4920
taagccctcc cgtatcgtag ttatctacac gacggggagt caggcaacta tggatgaacg   4980
aaatagacag atcgctgaga taggtgcctc actgattaag cattggtaaa actgtcagac   5040
caagtttact catatatact ttagattgat ttaaaacttc atttttaatt taaaaggatc   5100
taggtgaaga tcctttttga taatctcatg accaaaatcc cttaacgtga gttttcgttc   5160
```

-continued

```
cactgagcgt cagaccccgt agaaagatcg ttcaaacatt tggcaataaa gtttcttaag   5220
attgaatcct gttgccggtc ttgcgatgat tatcatataa tttctgttga attacgttaa   5280
gcatgtaata attaacatgt aatgcatgac gttatttatg agatgggttt ttatgattag   5340
agtcccgcaa ttatacattt aatacgcgat agaaaacaaa atatagcgcg caaactagga   5400
taaattatcg cgcgcggtgt catctatgtt actagatcgg atccatgagc ccagaacgac   5460
gcccggccga catccgccgt gccaccgagg cggacatgcc ggcggtctgc accatcgtca   5520
accactacat cgagacaagc acggtcaact tccgtaccga gccgcaggaa ccgcaggagt   5580
ggacggacga cctcgtccgt ctgcgggagc gctatccctg gctcgtcgcc gaggtggacg   5640
gcgaggtcgc cggcatcgcc tacgcgggcc cctggaaggc acgcaacgcc tacgactgga   5700
cggccgagtc gaccgtgtac gtctccccc gccaccagcg gacgggactg ggctccacgc   5760
tctacaccca cctgctgaag tccctggagg cacagggctt caagagcgtg gtcgctgtca   5820
tcgggctgcc caacgacccg agcgtgcgca tgcacgaggc gctcggatat gcccccgcg   5880
gcatgctgcg ggcggccggc ttcaagcacg ggaactggca tgacgtgggt ttctggcagc   5940
tggacttcag cctgccggta ccgccccgtc cggtcctgcc cgtcaccgag atcgatcgtt   6000
caaacatttg gcaataaagt ttcttaagat tgaatcctgt tgccggtctt gcgatgatta   6060
tcatataatt tctgttgaat tacgttaagc atgtaataat taacatgtaa tgcatgacgt   6120
tatttatgag atgggttttt atgattagag tcccgcaatt atacatttaa tacgcgatag   6180
aaaacaaaat atagcgcgca aactaggata aattatcgcg cgcggtgtca tctatgttac   6240
tagatcggaa ttcgtaatca tggtcatagc tgtttcctgt gtgaaattgt tatccgctca   6300
caattccaca caacatacga gccggaagca taaagtgtaa agcctggggt gcctaatgag   6360
tgagctaact cacattaatt gcgttgcgct cactgcccgc tttccagtcg ggaaacctgt   6420
cgtgccagct gcattaatga atcggccaac gcgcggggag aggcggtttg cgtattgggc   6480
gctcttccgc ttcctcgctc actgactcgc tgcgctcggt cgttcggctg cggcgagcgg   6540
tatcagctca ctcaaaggcg gtaatacggt tatccacaga atcaggggat aacgcaggaa   6600
agaacatgtg agcaaaaggc cagcaaaagg ccaggaaccg taaaaaggcc gcgttgctgg   6660
cgtttttcca taggctccgc ccccctgacg agcatcacaa aaatcgacgc tcaagtcaga   6720
ggtggcgaaa cccgacagga ctataaagat accaggcgtt tccccctgga agctccctcg   6780
tgcgctctcc tgttccgacc ctgccgctta ccggatacct gtccgccttt ctcccttcgg   6840
gaagcgtggc gctttctcat agctcacgct gtaggtatct cagttcggtg taggtcgttc   6900
gctccaagct gggctgtgtg cacgaacccc ccgttcagcc cgaccgctgc gccttatccg   6960
gtaactatcg tcttgagtcc aacccggtaa gacacgactt atcgccactg gcagcagcca   7020
ctggtaacag gattagcaga gcgaggtatg taggcggtgc tacagagttc ttgaagtggt   7080
ggcctaacta cggctacact agaaggacag tatttggtat ctgcgctctg ctgaagccag   7140
ttaccttcgg aaaaagagtt ggtagctctt gatccggcaa acaaaccacc gctggtagcg   7200
gtggtttttt tgtttgcaag cagcagatta cgcgcagaaa aaaaggatct caagaagatc   7260
ctttgatctt ttctacgggg tctgacgctc agtggaacga aaactcacgt taagggattt   7320
tggtcatgag attatcaaaa aggatcttca cctagatcct tttaaattaa aaatgaagtt   7380
ttaaatcaat ctaaagtata tatgagtaaa cttggtctga cagttaccaa tgcttaatca   7440
gtgaggcacc tatctcagcg atctgtctat ttcgttcatc catagttgcc tgactccccg   7500
tcgtgtagat aactacgata cgggagggct taccatctgg ccccagtgct gcaatgatac   7560
```

-continued

```
cgcgagaccc acgctcaccg gctccagatt tatcagcaat aaaccagcca gccggaaggg   7620
ccgagcgcag aagtggtcct gcaactttat ccgcctccat ccagtctatt aattgttgcc   7680
gggaagctag agtaagtagt tcgccagtta atagtttgcg caacgttgtt gccattgcta   7740
caggcatcgt ggtgtcacgc tcgtcgtttg gtatggcttc attcagctcc ggttcccaac   7800
gatcaaggcg agttacatga tcccccatgt tgtgcaaaaa agcggttagc tccttcggtc   7860
ctccgatcgt tgtcagaagt aagttggccg cagtgttatc actcatggtt atggcagcac   7920
tgcataattc tcttactgtc atgccatccg taagatgctt ttctgtgact ggtgagtact   7980
caaccaagtc attctgagaa tagtgtatgc ggcgaccgag ttgctcttgc ccggcgtcaa   8040
tacgggataa taccgcgcca catagcagaa ctttaaaagt gctcatcatt ggaaaacgtt   8100
cttcggggcg aaaactctca aggatcttac cgctgttgag atccagttcg atgtaaccca   8160
ctcgtgcacc caactgatct tcagcatctt ttactttcac cagcgtttct gggtgagcaa   8220
aaacaggaag gcaaaatgcc gcaaaaaagg gaataagggc gacacggaaa tgttgaatac   8280
tcatactctt cctttttcaa tattattgaa gcatttatca gggttattgt ctcatgagcg   8340
gatacatatt tgaatgtatt tagaaaaata aacaaatagg ggttccgcgc acatttcccc   8400
gaaaagtgcc acctgacgtc taagaaacca ttattatcat gacattaacc tataaaaata   8460
ggcgtatcac gaggcccttt cgtctcgcgc gtttcggtga tgacggtgaa aacctctgac   8520
acatgcagct cccggagacg gtcacagctt gtctgtaagc ggatgccggg agcagacaag   8580
cccgtcaggg cgcgtcagcg ggtgttggcg ggtgtcgggg ctggcttaac tatgcggcat   8640
cagagcagat tgtactgaga gtgcaccata tgcggtgtga aataccgcac agatgcgtaa   8700
ggagaaaata ccgcatcagg cgccattcgc cattcaggct gcgcaactgt tgggaagggc   8760
gatcggtgcg ggcctcttcg ctattacgcc agctggcgaa agggggatgt gctgcaaggc   8820
gattaagttg ggtaacgcca gggttttccc agtcacgacg ttgtaaaacg acggccagtg   8880
caagcttgca tgcctgcagt gcagcgtgac ccggtcgtgc ccctctctag agataatgag   8940
cattgcatgt ctaagttata aaaaattacc acatattttt tttgtcacac ttgtttgaag   9000
tgcagtttat ctatctttat acatatattt aaactttact ctacgaataa tataatctat   9060
agtactacaa taatatcagt gttttagaga atcatataaa tgaacagtta gacatggtct   9120
aaaggacaat tgagtatttt gacaacagga ctctacagtt ttatcttttt agtgtgcatg   9180
tgttctcctt tttttttgca aatagcttca cctatataat acttcatcca ttttattagt   9240
acatccattt agggtttagg gttaatggtt tttatagact aattttttta gtacatctat   9300
tttattctat tttagcctct aaattaagaa aactaaaact ctattttagt ttttttattt   9360
aataatttag atataaaata gaataaaata aagtgactaa aaattaaaca aataccottt   9420
aagaaattaa aaaaactaag gaaacatttt tcttgtttcg agtagataat gccagcctgt   9480
taaacgccgt cgacgagtct aacggacacc aaccagcgaa ccagcagcgt cgcgtcgggc   9540
caagcgaagc agacggcacg gcatctctgt cgctgcctct ggacccctct cgagagttcc   9600
gctccaccgt tggacttgct ccgctgtcgg catccagaaa ttgcgtggcg gagcggcaga   9660
cgtgagccgg cacggcaggc ggcctcctcc tcctctcacg gcaccggcag ctacggggga   9720
ttcctttccc accgctcctt cgctttccct tcctcgcccg ccgtaataaa tagacacccc   9780
ctccacaccc tctttcccca acctcgtgtt gttcggagcg cacacacaca caaccagatc   9840
tcccccaaat ccacccgtcg gcacctccgc ttcaaggtac gccgctcgtc ctcccccccc   9900
```

-continued

```
ccccctctct accttctcta gatcggcgtt ccggtccatg gttagggccc ggtagttcta   9960
cttctgttca tgtttgtgtt agatccgtgt ttgtgttaga tccgtgctgc tagcgttcgt  10020
acacggatgc gacctgtacg tcagacacgt tctgattgct aacttgccag tgtttctctt  10080
tggggaatcc tgggatggct ctagccgttc cgcagacggg atcgatttca tgattttttt  10140
tgtttcgttg catagggttt ggtttgccct tttcctttat ttcaatatat gccgtgcact  10200
tgtttgtcgg gtcatctttt catgcttttt tttgtcttgg ttgtgatgat gtggtctggt  10260
tgggcggtcg ttctagatcg gagtagaatt ctgtttcaaa ctacctggtg gatttattaa  10320
ttttggatct gtatgtgtgt gccatacata ttcatagtta cgaattgaag atgatggatg  10380
gaaatatcga tctaggatag gtatacatgt tgatgcgggt tttactgatg catatacaga  10440
gatgcttttt gttcgcttgg ttgtgatgat gtggtgtggt tgggcggtcg ttcattcgtt  10500
ctagatcgga gtagaatact gtttcaaact acctggtgta tttattaatt ttggaactgt  10560
atgtgtgtgt catacatctt catagttacg agtttaagat ggatggaaat atcgatctag  10620
gataggtata catgttgatg tgggttttac tgatgcatat acatgatggc atatgcagca  10680
tctattcata tgctctaacc ttgagtacct atctattata ataaacaagt atgttttata  10740
attattttga tcttgatata cttggatgat ggcatatgca gcagctatat gtggattttt  10800
ttagccctgc cttcatacgc tatttatttg cttggtactg tttcttttgt cgatgctcac  10860
cctgttgttt ggtgttactt ctgcagggat ccatgagccc agaacgacgc ccggccgaca  10920
tccgccgtgc caccgaggcg gacatgccgg cggtctgcac catcgtcaac cactacatcg  10980
agacaagcac ggtcaacttc cgtaccgagc cgcaggaacc gcaggagtgg acggacgacc  11040
tcgtccgtct gcgggagcgc tatccctggc tcgtcgccga ggtggacggc gaggtcgccg  11100
gcatcgccta cgcgggcccc tggaaggcac gcaacgccta cgactggacg gccgagtcga  11160
ccgtgtacgt ctcccccgc caccagcgga cgggactggg ctccacgctc tacacccacc  11220
tgctgaagtc cctggaggca cagggcttca agagcgtggt cgctgtcatc gggctgccca  11280
acgacccgag cgtgcgcatg cacgaggcgc tcggatatgc cccccgcggc atgctgcggg  11340
cggccggctt caagcacggg aactggcatg acgtgggttt ctggcagctg gacttcagcc  11400
tgccggtacc gccccgtccg gtcctgcccg tcaccgagat cgatcgttca aacatttggc  11460
aataaagttt cttaagattg aatcctgttg ccggtcttgc gatgattatc atataatttc  11520
tgttgaatta cgttaagcat gtaataatta acatgtaatg catgacgtta tttatgagat  11580
gggtttttat gattagagtc ccgcaattat acatttaata cgcgatagaa aacaaaatat  11640
agcgcgcaaa ctaggataaa ttatcgcgcg cggtgtcatc tatgttacta gatctgctac  11700
aggcatcgtg gtgtcacgct cgtcgtttgg tatggcttca ttcagctccg gttcccaacg  11760
atcaaggcga gttacatgat cccccatgtt gtgcaaaaaa gcggttagct ccttcggtcc  11820
tccgatcgtt gtcagaagta agttggccgc agtgttatca ctcatggtta tggcagcact  11880
gcataattct cttactgtca tgccatccgt aagatgcttt tctgtgactg gtgagtactc  11940
aaccaagtca ttctgagaat agtgtatgcg gcgaccgagt tgctcttgcc cggcgtcaat  12000
acgggataat accgcgccac atagcagaac tttaaaagtg ctcatcattg gaaaacgttc  12060
ttcggggcga aaactctcaa ggatcttacc gctgttgaga tccagttcga tgtaacccac  12120
tcgtgcaccc aactgatctt cagcatcttt tactttcacc agcgtttctg ggtgagcaaa  12180
aacaggaagg caaaatgccg caaaaaaggg aataagggcg acacggaaat gttgaatact  12240
catactcttc ctttttcaat attattgaag catttatcag ggttattgtc tcatgagcgg  12300
```

```
atacatattt gaatgtattt agaaaaataa acaaataggg gttccgcgca catttccccg  12360
aaaagtgcca cctgacgtct aagaaaccat tattatcatg acattaacct ataaaaatag  12420
gcgtatcacg aggccctttc gtctcgcgcg tttcggtgat gacggtgaaa acctctgaca  12480
catgcagctc ccggagacgg tcacagcttg tctgtaagcg gatgccggga gcagacaagc  12540
ccgtcagggc gcgtcagcgg gtgttggcgg gtgtcggggc tggcttaact atgcggcatc  12600
agagcagatt gtactgagag tgcaccatat gcggtgtgaa ataccgcaca gatgcgtaag  12660
gagaaaatac cgcatcaggc gccattcgcc attcaggctg cgcaactgtt gggaagggcg  12720
atcggtgcgg gcctcttcgc tattacgcca gctggcgaaa gggggatgtg ctgcaaggcg  12780
attaagttgg gtaacgccag ggttttccca gtcacgacgt tgtaaaacga cggccagtgc  12840
caagcttgca tgcctgcagt gcagcgtgac ccggtcgtgc ccctctctag agataatgag  12900
cattgcatgt ctaagttata aaaaattacc acatattttt tttgtcacac ttgtttgaag  12960
tgcagtttat ctatctttat acatatattt aaactttact ctacgaataa tataatctat  13020
agtactacaa taatatcagt gttttagaga atcatataaa tgaacagtta gacatggtct  13080
aaaggacaat tgagtatttt gacaacagga ctctacagtt ttatcttttt agtgtgcatg  13140
tgttctcctt ttttttttgca aatagcttca cctatataat acttcatcca ttttattagt  13200
acatccattt agggtttagg gttaatggtt tttatagact aatttttttta gtacatctat  13260
tttattctat tttagcctct aaattaagaa aactaaaact ctattttagt tttttttattt  13320
aataatttag atataaaata gaataaaata aagtgactaa aaattaaaca aatacccttt  13380
aagaaattaa aaaaactaag gaaacatttt tcttgtttcg agtagataat gccagcctgt  13440
taaacgccgt ttgttgaata gaatacaaac cctagaaaaa caaggcacat ctcggcgccg  13500
ccaatagaag gcagaaaccc tagccgtcat ttttcttgaa gaatatagag cgacgtcgat  13560
aggaagatac ttaaatgttg aatccaagca cctagaataa tgagttagat tagaagaaaa  13620
ctatcaactt cgaaatcaag aagaaatgtt ttattctgtt gcataaaact ttcgcgtgga  13680
gaagctctgt tcagagcccg ggtagccact gggcacgtct cctagatact ggactcatcg  13740
gacgctctcc tcgagccatt aatatggtcc gtcctgtaga aaccccaacc cgtgaaatca  13800
aaaaactcga cggcctgtgg gcattcagtc tggatcgcga aaactgtgga attgatcagc  13860
gttggtggga aagcgcgtta caagaaagcc gggcaattgc tctcctgttc cgaccctgcc  13920
gcttaccgga tacctgtccg cctttctccc ttcgggaagc gtggcgcttt ctcatagctc  13980
acgctgtagg tatctcagtt cggtgtaggt cgttcgctcc aagctcggca tccggtcagt  14040
ggcagtgaag ggcgaacagt tcctgattaa ccacaaaccg ttctacttta ctggctttgg  14100
tcgtcatgaa gatgcggact tgcgtggcaa aggattcgat aacgtgctga tggtgcacga  14160
ccacgcattg atggactgga ttggggccaa ctcctaccgt acctcgcatt acccttacgc  14220
tgaagagatg ctcgactggg cagatgaaca tggcatcgtg gtgattgatg aaactgctgc  14280
tgtcggcttt aacctctctt taggcattgg tttcgaagcg ggcaacaagc cgaaagaact  14340
gtacagcgaa gaggcagtca acggggaaac tcagcaagcg cacttacagg cgattaaaga  14400
gctgatagcg cgtgacaaaa accacccaag cgtggtgatg tggagtattg ccaacgaacc  14460
ggatacccgt ccgcaaggtg cacgggaata tttcgcgcca ctggcggaag caacgcgtaa  14520
actcgacccg acgcgtccga tcacctgcgt caatgtaatg ttctgcgacg ctcacaccga  14580
taccatcagc gatctctttg atgtgctgtg cctgaaccgt tattacggat ggtatgtcca  14640
```

-continued aagcggcgat ttggaaacgg cagagaaggt actggaaaaa gaacttctgg cctggcagga 14700
gaaactgcat cagccgatta tcatcaccga atacggcgtg gatacgttag ccgggctgca 14760
ctcaatgtac accgacatgt ggagtgaaga gtatcagtgt gcatggctgg atatgtatca 14820
ccgcgtcttt gatcgcgtca gcgccgtcgt cggtgaacag gtatggaatt tcgccgattt 14880
tgcgacctcg caaggcatat tgcgcgttgg cggtaacaag aaagggatct tcactcgcga 14940
ccgcaaaccg aagtcggcgg ctcgctcagt gtgtgtgact ctgctggtgc tggggaatgg 15000
agctcggggc accgtatttg tagcgcgcgc gccgctgtac gtggcgccct ggcgcggcta 15060
cgtggagggg agctgcgtgc cagaggggag gcgggccgcc acgtcgcacg gccgtgctta 15120
tcgggccatc ggcgaggtgc gtgccagctt gggcgtcgcg tgtcgtggag cgctcctgct 15180
cgcggcggag ctggttgagt ggattgcgat gcggtgcttg gtacagagct cgatggacaa 15240
ctcgaggaga gcgtccgatg agtccagtat ctaggagacg tgcccagtgg ctacccgggc 15300
tctgaacaga gcttctccac gcgaaagttt tatgcaacag aataaaacat ttcttcttga 15360
tttcgaagtt gatagttttc ttctaatcta actcattatt ctaggtgctt ggattcaaca 15420
tttaagtatc ttcctatcga cgtcgctcta tattcttcaa gaaaaatgac ggctagggtt 15480
tctgccttct attggtcatt acgcgcagaa aaaaaggatc tcaagaagat cctttgatct 15540
tttctacggg gtctgacgct cagtggaacg aaaactcacg ttaagggatt ttggtcatga 15600
gattatcaaa aaggatcttc acctagatcc ttttaaatta aaaatgaagt tttaaatcaa 15660
tctaaagtat atatgagtaa acttggtctg acagttttac caatgcttaa tcagtgaggc 15720
acctatctca gcgatctgtc tatttcgttc atccatagtt gcctgactcc ccgtcgtgta 15780
gataactacg atacgggagg gcttaccatc tggccccagt gctgcaatga taccgcgaga 15840
cccacgctca ccggctccag atttatcagc aataaaccag ccagccggaa gggccgagcg 15900
cagaagtggt cctgcaactt tatccgcctc catccagtct attaattgtt gccgggaagc 15960
tagagtaagt agttcgccag ttaatagttt gcgcaacgtt gttgccattg ctacaggcat 16020
cgtggtgtca cgctcgtcgt ttggtatggc ttcattcagc tccggttccc aacgatcaag 16080
gcgagttaca tgatccccca tgttgtgcaa aaaagcggtt agctccttcg gtcctccgat 16140
cgttgtcaga agtaagttgg ccgcagtgtt atcactcatg gttatggcag cactgcataa 16200
ttctcttact gtcatgccat ccgtaagatg cttttctgtg actggtgagt actcaaccaa 16260
gtcattctga gaatagtgta tgcggcgacc gagttgctct tgcccggcgt caatacggga 16320
taataccgcg ccacatagca gaactttaaa agtgctcatc attggaaaac gttcttcggg 16380
gcgaaaactc tcaaggatct taccgctgtt gagatccagt tcgatgtaac ccactcgtgc 16440
acccaactga tcttcagcat cttttacttt caccagcgtt tctgggtgag caaaaacagg 16500
aaggcaaaat gccgcaaaaa agggaataag ggcgacacgg aaatgttgaa tactcatact 16560
cttccttttt caatattatt gaagcattta tcagggttat tgtctcatga gcggatacat 16620
atttgaatgt atttagaaaa ataaacaaat aggggttccg cgcacatttc cccgaaaagt 16680
gccacctgac gtctaagaaa ccattattat catgacatta acctataaaa ataggcgtat 16740
cacgaggccc tttcgtctcg cgcgtttcgg tgatgacggt gaaaacctct gacacatgca 16800
gctcccggag acggtcacag cttgtctgta agcggatgcc gggagcagac aagcccgtca 16860
gggcgcgtca gcgggtgttg gcgggtgtcg gggctggctt aactatgcgg catcagagca 16920
gattgtactg agagtgcacc atatgcggtg tgaaataccg cacagatgcg taaggagaaa 16980
ataccgcatc aggcgccatt cgccattcag gctgcgcaac tgttgggaag ggcgatcggt 17040
gcgggcctct tcgctattac gccagctggc gaaaggggga tgtgctgcaa ggcgattaag 17100
ttgggtaacg ccagggtttt cccagtcacg acgttgtaaa acgacggcca gtgccaagct 17160
tgcatgcctg cagtgcagcg tgacccggtc gtgcccctct ctagagataa tgagcattgc 17220
atgtctaagt tataaaaaat taccacatat ttttttgtc acacttgttt gaagtgcagt 17280
ttatctatct ttatacatat atttaaactt tactctacga ataatataat ctatagtact 17340
acaatgtacg ccgctcgtcc tcccccccc cccctctcta ccttctctag atcggcgttc 17400
cggtccatgg ttagggcccg gtagttctac ttctgttcat gtttgtgtta gatccgtgtt 17460
tgtgttagat ccgtgctgct agcgttcgta cacggatgcg acctgtacgt cagacacgtt 17520
ctgattgcta acttgccagt gtttctcttt ggggaatcct gggatggctc tagccgttcc 17580
gcagacggga tcgatttcat gatttttttt gtttcgttgc atagggtttg gtttgccctt 17640
ttcctttatt tcaatatatg ccgtgcactt gtttgtcggg tcatcttttc atgctttttt 17700
ttgtcttggt tgtgatgatg tggtctggtt gggcggtcgt tctagatcgg agtagaattc 17760
tgtttcaaac tacctggtgg atttattaat tttggatctg tatgtgtgtg ccatacatat 17820
tcatagttac gaattgaaga tgatggatgg aaatatcgat ctaggatagg tatacatgtt 17880
gatgcgggtt ttactgatgc atatacagag atgctttttg ttcgcttggt tgtgatgatg 17940
tggtgtggtt gggcggtcgt tcattcgttc tagatcggag tagaatactg tttcaaacta 18000
cctggtgtat ttattaattt tggaactgta tgtgtgtgtc atacatcttc atagttacga 18060
gtttaagatg gatggaaata tcgatctagg ataggtatac atgttgatgt gggttttact 18120
gatgcatata catgatggca tatgcagcat ctattcatat gctctaacct tgagtaccta 18180
tctattataa taaacaagta tgttttataa ttattttgat cttgatatac ttggatgatg 18240
gcatatgcag cagctatatg tggatttttt tagccctgcc ttcatacgct atttatttgc 18300
ttggtactgt ttcttttgtc gatgctcacc ctgttgtttg gtgttacttc tgcagtcgac 18360
tcgtagagga tccatcccga ttaggaaagt agagcatgag cccagaacga cgcccggccg 18420
acatccgccg tgccaccgag gcggacatgc cggcggtctg caccatcgtc aaccactaca 18480
tcgagacaag cacggtcaac ttccgtaccg agccgcagga accgcaggag tggacggacg 18540
acctcgtccg tctgcgggag cgctatccct ggctcgtcgc cgaggtggac ggcgaggtcg 18600
ccggcatcgc ctacgcgggc ccctggaagg cacgcaacgc ctacgactgg acggccgagt 18660
cgaccgtgta cgtctccccc cgccaccagc ggacgggact gggctccacg ctctacaccc 18720
acctgctgaa gtccctggag gcacagggct tcaagagcgt ggtcgctgtc atcgggctgc 18780
ccaacgaccc gagcgtgcgc atgcacgagg cgctcggata tgcccccgc ggcatgctgc 18840
gggcggccgg cttcaagcac gggaactggc atgacgtggg tttctggcag ctggacttca 18900
gcctgccggt accgccccgt ccggtcctgc ccgtcaccga gatcatatga atagatgctg 18960
catatgccat catgtatatg catcagtaaa acccacatca acatgtatac ctatcctaga 19020
tcgatatttc catccatctt aaactcgtaa ctatgaagat gtatgacaca cacatacagt 19080
tccaaaattt ataaatacac caggtagttt gaaacagtat tctactccga tctagaacga 19140
atgaacgacc gcccaaccac accacatcat cacaaccaag cgaacaaaaa gcatctctgt 19200
atatgcatca gtaaaacccg catcaacatg tatacctatc ctagatcgat atttccatcc 19260
atcatcttca attcgtaact atgaatatgt atggcacaca catacagatc caaaattaat 19320
aaatccacca ggtagtttga aacagaattc tactccgatc tagaacgacc gcccaaccag 19380

-continued

```
accacatcat cacaaccaag acaaaaaaaa gcatgaaaag atgacccgac aaacaagtgc  19440
acggcatata ttgaaataaa ggaaaagggc aaaccaaacc ctatgcaacg aaacaaaaaa  19500
aatcatgaaa tcgatcccgt ctgcggaacg gctagagcca tcccaggatt ccccaaagag  19560
aaacactggc aagttagcaa tcagaacgtg tctgacgtac aggtcgcatc cgtgtacgaa  19620
cgctagcagc acggatctaa cacaaacacg gatctaacac aaacatgaac agaagtagaa  19680
ctaccgggcc ctaaccatgg accggaacgc cgatctagag aaggtagaga gggggggggg  19740
gggaggacga gcggcgtacg ccgacgggtg gatttggggg agatctggtt gtgtgtgtgt  19800
gcgctccgaa caacacgagg ttggggaaag agggtgtgga gggggtgtct atttattacg  19860
gcgggcgagg aagggaaagc gaaggagcgg tgggaaagga atccccccgta gctgccggtg  19920
ccgtgagagg aggaggaggc cgcctgccgt gccggctcac gtctgccgct ccgccacgca  19980
atttctggat gccgacagcg gagcaagtcc aacggtggag cggaactctc gagaggggtc  20040
cagaggcagc gacagagatg ccgtgccgtc tgcttcgctt ggcccgacgc gacgctgctg  20100
gttcgctggt tggtgtccgt tagactcgtc gacggcgttt aacaggctgg cattatctac  20160
tcgaaacaag aaaaatgttt ccttagtttt tttaatttct taaagggtat ttgtttaatt  20220
tttagtcact ttattttatt ctattttata tctaaattat taaataaaaa aactaaaata  20280
gagttttagt tttcttaatt tagaggctaa aatagaataa aatagatgta ctaaaaaaat  20340
tagtctataa aaaccattaa ccctaaaccc taaatggatg tactaataaa atggatgaag  20400
tattatatag gtgaagctat ttgcaaaaaa aaaggagaac acatgcacac taaaaagata  20460
aaactgtaga gtcctgttgt caaaatactc aattgtcctt tagaccatgt ctaactgttc  20520
atttatatga ttctctaaaa cactgatatt attgtagtac tatagattat attattcgta  20580
gagtaaagtt taaatatatg tataaagata gataaactgc acttcaaaca agtgtgacaa  20640
aaaaaatatg tggtaatttt ttataactta gacatgcaat gctcattatc tctagagagg  20700
ggcacgaccg ggtcacgctg cactgcaggc atgcaagctt gcactggccg tcgttttaca  20760
acgtcgtgac tgggaaaacc ctggcgttac ccaacttaat cgccttgcag cacatccccc  20820
tttcgccagc tggcgtaata gcgaagaggc ccgcaccgat cgcccttccc aacagttgcg  20880
cagcctgaat ggcgaatggc gcctgatgcg gtattttctc cttacgcatc tgtgcggtat  20940
ttcacaccgc atatggtgca ctctcagtac aatctgctct gatgccgcat agttaagcca  21000
gccccgacac ccgccaacac ccgctgacgc gccctgacgg gcttgtctgc tcccggcatc  21060
cgcttacaga caagctgtga ccgtctccgg gagctgcatg tgtcagaggt tttcaccgtc  21120
atcaccgaaa cgcgcgagac gaaagggcct cgtgatacgc ctatttttat aggttaatgt  21180
catgataata atggtttctt agacgtcagg tggcactttt cggggaaatg tgcgcggaac  21240
ccctatttgt ttatttttct aaatacattc aaatatgtat ccgctcatga gacaataacc  21300
ctgataaatg cttcaataat attgaaaaag gaagagtatg agtattcaac atttccgtgt  21360
cgcccttatt cccttttttg cggcattttg ccttcctgtt tttgctcacc cagaaacgct  21420
ggtgaaagta aaagatgctg aagatcagtt gggtgcacga gtgggttaca tcgaactgga  21480
tctcaacagc ggtaagatcc ttgagagttt tcgccccgaa gaacgttttc caatgatgag  21540
cacttttaaa gttctgctat gtggcgcggt attatcccgt attgacgccg ggcaagagca  21600
actcggtcgc cgcatacact attctcagaa tgacttggtt gagtactcac cagtcacaga  21660
aaagcatctt acggatggca tgacagtaag agaattatgc agtgctgcca taaccatgag  21720
tgataacact gcggccaact tacttctgac aacgatcgga ggaccgaagg agctaaccgc  21780
```

tttttgcac aacatggggg atcatgtaac tcgccttgat cgttgggaac cggagctgaa 21840
tgaagccata ccaaacgacg agcgtgacac cacgatgcct gtagcaatgg caacaacgtt 21900
gcgcaaacta ttaactggcg aactacttac tctagcttcc cggcaacaat taatagactg 21960
gatggaggcg gataaagttg caggaccact tctgcgctcg gcccttccgg ctggctggtt 22020
tattgctgat aaatctggag ccggtgagcg tgggtctcgc ggtatcattg cagcactggg 22080
gccagatggt aagccctccc gtatcgtagt tatctacacg acggggagtc aggcaactat 22140
ggatgaacga aatagacaga tcgctgagat aggtgcctca ctgattaagc attggtaact 22200
gtcagaccaa gtttactcat atatacttta gattgattta aaacttcatt tttaatttaa 22260
aaggatctag gtgaagatcc tttttgataa tctcatgacc aaaatccctt aacgtgagtt 22320
ttcgttccac tgagcgtcag accccgtaga aaagatcaaa ggatcttctt gagatccttt 22380
ttttctgcgc gtaatctgct gcttgcaaac aaaaaaacca ccgctaccag cggtggtttg 22440
tttgccggat caagagctac caactctttt tccgaaggta actggcttca gcagagcgca 22500
gataccaaat actgtccttc tagtgtagcc gtagttaggc caccacttca agaactctgt 22560
agcaccgcct acatacctcg ctctgctaat cctgttacca gtggctgctg ccagtggcga 22620
taagtcgtgt cttaccgggt tggactcaag acgatagtta ccggataagg cgcagcggtc 22680
gggctgaacg gggggttcgt gcacacagcc cagcttggag cgaacgacct acaccgaact 22740
gagataccta cagcgtgagc tatgagaaag cgccacgctt cccgaaggga gaaaggcgga 22800
caggtatccg gtaagcggca gggtcggaac aggagagcgc acgagggagc ttccaggggg 22860
aaacgcctgg tatctttata gtcctgtcgg gtttcgccac ctctgacttg agcgtcgatt 22920
tttgtgatgc tcgtcagggg ggcggagcct atggaaaaac gccagcaacg cggccttttt 22980
acggttcctg gccttttgct ggccttttgc tcacatgttc tttcctgcgt tatcccctga 23040
ttctgtggat aaccgtatta ccgcctttga gtgagctgat accgctcgcc gcagccgaac 23100
gaccgagcgc agcgagtcag tgagcgagga agcggaagag cgcccaatac gcaaaccgcc 23160
tctccccgcg cgttggccga ttcatttatg cagctggcac gacaggtttc ccgactggaa 23220
agcgggcagt gagcgcaacg caatttatgt gagttagctc actcattagg caccccaggc 23280
tttacacttt atgcttccgg ctcgtatgtt aagcttgcat gcctgcagtg cagcgtgacc 23340
cggtcgtgcc cctctctaga gataatgagc attgcatgtc taagttataa aaaattacca 23400
catatttttt ttgtcacact tgtttgaagt gcagtttatc tatctttata catatattta 23460
aactttactc tacgaataat ataatctata gtactacaat aatatcagtg ttttagagaa 23520
tcatataaat gaacagttag acatggtcta aaggacaatt gagtattttg acaacaggac 23580
tctacagttt tatcttttta gtgtgcatgt gttctccttt ttttttgcaa atagcttcac 23640
ctatataata cttcatccat tttattagta catccattta gggtttaggg ttaatggttt 23700
ttatagacta atttttttag tacatctatt ttattctatt ttagcctcta aattaagaaa 23760
actaaaactc tattttagtt tttttattta ataatttaga tataaaatag aataaaataa 23820
agtgactaaa aattaaacaa ataccctta agaaattaaa aaaactaagg aaacattttt 23880
cttgtttcga gtagataatg ccagcctgtt aaacgccgtc gacgagtcta acggacacca 23940
accagcgaac cagcagcgtc gcgtcgggcc aagcgaagca gacggcacgg catctctgtc 24000
gctgcctctg gacccctctc gagagttccg ctccaccgtt ggacttgctc cgctgtcggc 24060
atccagaaat tgcgtggcgg agcggcagac gtgagccggc acggcaggcg gcctcctcct 24120

-continued

```
cctctcacgg caccggcagc tacgggggat tcctttccca ccgctccttc gctttccctt  24180
cctcgcccgc cgtaataaat agacacccga actgtatgtg tgtgtcatac atcttcatag  24240
ttacgagttt aagatggatg gaaatatcga tctaggatag gtatacatgt tgatgtgggt  24300
tttactgatg catatacatg atggcatatg cagcatctat tcatatgctc taaccttgag  24360
tacctatcta ttataataaa caagtatgtt ttataattat tttgatcttg atatacttgg  24420
atgatggcat atgcagcagc tatatgtgga tttttttagc cctgccttca tacgctattt  24480
atttgcttgg tactgtttct tttgtcgatg ctcaccctgt tgtttggtgt tacttctgca  24540
gggatccatg tctcttcaac aagtaacaac caccaggaag aaccgaaacg aggggcggag  24600
acgatttacc gacaaacaaa taagtttcct agagtacatg tttgagacac agtcgagacc  24660
cgagttaagg atgaaacacc agttggcaca taaactcggg cttcatcctc gtcaagtggc  24720
gatatggttc cagaacaaac gcgcgcgatc aaagtcgagg cagattgagc aagagtataa  24780
cgcgctaaag cataactacg agacgcttgc gtctaaatcc gagtctctaa agaaagagaa  24840
tcaggcccta ctcaatcaat tggaggtgct gagaaatgta gccgaaaagc atcaagagaa  24900
aactagtagt agtggcagcg gtgaagaatc ggatgatcgg tttacgaact ctccggacgt  24960
tatgtttggt caagaaatga atgttccgtt ttgcgacggt tttgcgtacc ttgaagaagg  25020
aaacagtttg ttggagattg aagaacaact gccagacctt caaaagtggt gggagttcga  25080
tcgttcaaac atttggcaat aaagtttctt aagattgaat cctgttgccg gtcttgcgat  25140
gattatcata taatttctgt tgaattacgt taagcatgta ataattaaca tgtaatgcat  25200
gacgttattt atgagatggg tttttatgat tagagtcccg caattataca tttaatacgc  25260
gatagaaaac aaaatatagc gcgcaaacta ggataaatta tcgcgcgcgg tgtcatctat  25320
gttactagat cggaattcgt aatcatggtc atagctgttt cctgtgtgaa attgttatcc  25380
gctcacaatt ccacacaaca tacgagccgg aagcataaag tgtaaagcct ggggtgccta  25440
atgagtgagc taactcacat taattgcgtt gcgctcactg cccgctttcc agtcgggaaa  25500
cctgtcgtgc cagctgcatt aatgaatcgg ccaacgcgcg gggagaggcg gtttgcgtat  25560
tgggcgctct tccgcttcct cgctcactga ctcgctgcgc tcggtcgttc ggctgcggcg  25620
agcggtatca gctcactcaa aggcggtaat acggttatcc acagaatcag gggataacgc  25680
aggaaagaac atgtgagcaa aaggccagca aaaggccagg aaccgtaaaa aggccgcgtt  25740
gctggcgttt ttccataggc tccgcccccc tgacgagcat cacaaaaatc gacgctcaag  25800
tcagaggtgg cgaaacccga caggactata aagataccag gcgtttcccc ctggaagctc  25860
cctcgtgcgc tctcctgttc cgaccctgcc gcttaccgga tacctgtccg cctttctccc  25920
ttcgggaagc gtggcgcttt ctcatagctc acgctgtagg tatctcagtt cggtgtaggt  25980
cgttcgctcc aagctgggct gtgtgcacga accccccgtt cagcccgacc gctgcgcctt  26040
atccggtaac tatcgtcttg agtccaaccc ggtaagacac gacttatcgc cactggcagc  26100
agccactggt aacaggatta gcagagcgag gtatgtaggc ggtgctacag agttcttgaa  26160
gtggtggcct aactacggct acactagaag gacagtattt ggtatctgcg ctctgctgaa  26220
gccagttacc ttcggaaaaa gagttggtag ctcttgatcc ggcaaacaaa ccaccgctgg  26280
tagcggtggt ttttttgttt gcaagcagca gattacgcgc agaaaaaaag gatctcaaga  26340
agatcctttg atcttttcta cggggtctga cgctcagtgg aacgaaaact cacgttaagg  26400
gattttggtc atgagattat caaaaaggat cttcacctag atccttttaa attaaaaatg  26460
aagttttaaa tcaatctaaa gtatatatga gtaaacttgg tctgacagtt gatcgttggg  26520
```

```
aaccggagct gaatgaagcc ataccaaacg acgagcgtga caccacgatg cctgtagcaa   26580

tggcaacaac gttgcgcaaa ctattaactg gcgaactact tactctagct tcccggcaac   26640

aattaataga ctggatggag gcggataaag ttgcaggacc acttctgcgc tcggcccttc   26700

cggctggctg gtttattgct gataaatctg gagccggtga gcgtgggtct cgcggtatca   26760

ttgcagcact ggggccagat ggtaagccct cccgtatcgt agttatctac acgacgggga   26820

gtcaggcaac tatggatgaa cgaaatagac agatcgctga gataagactg tcagaccaag   26880

tttactcata tatactttag attgatttaa aacttcattt ttaatttaaa aggatctagg   26940

tgaagatcct ttttgataat ctcatgacca aaatcccttta acgtgagttt tcgttccact   27000

gagcgtcaga ccccgtagaa aagatcaaag gatcttcttg agatcctttt tttctgcgcg   27060

taatctgctg cttgcaaaca aaaaaaccac cgctaccagc ggtggtttgt ttgccggatc   27120

aagagctacc aactcttttt ccgaaggtaa ctggcttcag cagagcgcag ataccaaata   27180

ctgtccttct agtgtagccg tagttaggcc accacttcaa gaactctgta gcaccgccta   27240

catacctcgc tctgctaatc ctgttaccag tggctgctgc cagtggcgat aagtcgtgtc   27300

ttaccgggtt ggactcaaga cgatagttac cggataaggc gcagcggtcg ggctgaacgg   27360

ggggttcgtg cacacagccc agcttggagc gaacgaccta caccgaactg agatacctac   27420

agcgtgagct atgagaaagc gccacgcttc ccgaagggag aaaggcggac aggtatccgg   27480

taagcggcag ggtcggaaca ggagagcgca cgagggagct tccaggggga aacgcctggt   27540

atctttatag tcctgtcggg tttcgccacc tctgacttga gcgtcgattt ttgtgatgct   27600

cgtcaggggg gcggagccta tggaaaaacg ccagcaacgc gacgctgggc cgccttttta   27660

cggttcctgg ccttttgctg gccttttgct cacatgttct ttcctgcgtt atcccctgat   27720

tctgtggata accgtattac cgcctttgag tgagctgata gtgtcacgca gatcctatga   27780

aatttggtcg atgattgtct tttatggatc cgttcagacc aagtcttcgt gtgtctatgt   27840

tatcgtgcct ttaaattgaa tccttttcgat ttatgcttct ttttgtcagc ggtggttgat   27900

cttctgatgt gctggttaca aagggtctta gcataacaat tttccaattg tctactacaa   27960

caagttttgt ctaacttcga tgaagcctag gtgatgacga tttcaacttg cttcggtgct   28020

tgtaactgtt attagatggt ctacggatct aaatgtaact tctattattt gttgtgtttt   28080

ttgtattatt atgatggatg atgaatagat taaaagatcc cgcaaataaa accttaaatg   28140

ataaatgtca cacgtcacgt gcatggcact ccggccctaa tgccttttgt agctattcta   28200

gtaacgcaag gatagcaaat ttccgtgaca cgacgcaagt ttttgttaaa aataaattaa   28260

agcaagaaaa ttgtcatact tgctaacgaa aattgccatc cttgcctatt catcatccat   28320

cataataata caaaaaacac aacaaataat agaagttaca tttagatccg tagaccatct   28380

aataacagtt acaagcaccg aagcaagttg gtgccgtctg cttcgcttgg cccgacgcga   28440

cgctgctggt tcgctggttg gtgtccgtta gactcgtcga cggcgtttaa caggctggca   28500

ttatctactc gaaacaagaa aaatgtttcc ttagtttttt taatttctta aagggtattt   28560

gtttaatttt tagtcacttt attttattct atttttatatc taaattatta aataaaaaaa   28620

ctaaaataga gttttagttt tcttaattta gaggctaaaa tagaataaaa tagatgtact   28680

aaaaactcaa ttgtcctttta gaccatgtct aactgttcat ttatatgatt ctctaaggca   28740

ctggccgtcg ttttacaacg tcgtgactgg gaaaaccctg gcgttaccca acttaatcgc   28800

cttgcagcac atcccccttt cgccagctgg cgtaatagcg aagaggcccg caccgatcgc   28860
```

-continued ccttcccaac agttgcgcag cctgaatggc gaatggcgcc tgatgcggta ttttctcctt 28920
acgcatctgt gcggtatttc acaccgcata tggtgcactc tcagtacaat ctgctctgat 28980
gccgcatagt taagccagcc ccgacacccg ccaacacccg ctgacgcgcc ctgacgggct 29040
tgtctgctcc cggcatccgc ttacagacaa gctgtgaccg tctccgggag ctgcatgtgt 29100
cagaggtttt caccgtcatc accgaaacgc gcgagacgaa agggcctcgt gatacgccta 29160
tttttatagg ttaatgtcat gataataatg gtttcttaga cgtcaggtgg cacttttcgg 29220
ggaaatgtgc gcggaacccc tatttgttta tttttctaaa tacattacca atgcttaatc 29280
agtgaggcac ctatctcagc gatctgtcta tttcgttcat ccatagttgc ctgactcccc 29340
gtcgtgtaga taactacgat acgggagggc ttaccatctg gccccagtgc tgcaatgata 29400
ccgcgagacc cacgctcacc ggctccagat ttatcagcaa taaaccagcc agccggaagg 29460
gccgagcgca gaagtggtcc tgcaacttta tccgcctcca tccagtctat taattgttgc 29520
cgggaagcta gagtaagtag ttcgccagtt aatagtttgc gcaacgttgt tgccattgct 29580
acaggcatcg tggtgtcacg ctcgtcgttt ggtatggctt cattcagctc cggttcccaa 29640
cgatcaaggc gagttacatg atcccccatg ttgtgcaaaa aagcggttag ctccttcggt 29700
cctccgaata ccgcgccaca tagcagaact ttaaaagtgc tcatcattgg aaaacgttct 29760
tcggggcgaa aactctcaag gatcttaccg ctgttgagat ccagttcgat gtaacccact 29820
cgtgcaccca actgatcttc agcatctttt actttcacca gcgtttctgg gtgagcaaaa 29880
acaggaaggc aaaatgccgc aaaaaaggga ataagggcga cacggaaatg ttgaatactc 29940
atactcttcc tttttcaata ttattgaagc atttatcagg gttattgtct catgagcgga 30000
tacatatttg aagatctcgg tgacgggcag gaccggacgg ggcggtaccg gcaggctgaa 30060
gtccagctgc cagaaaccca cgtcatgcca gttcccgtgc ttgaagccgg ccgcccgcag 30120
catgccgcgg ggggcatatc cgagcgcctc gtgcatgcgc acgctcgggt cgttgggcag 30180
cccgatgaca gcgaccacgc tcttgaagcc ctgtgcctcc agggacttca gcaggtgggt 30240
gtagagcgtg gagcccagtc ccgtccgctg gtggcggggg gagacgtaca cggtcgactc 30300
ggccgtccag tcgtaggcgt tgcgtgcctt ccaggggccc gcgtaggcga tgccggcgac 30360
ctcgccgtat ggatgaagta ttatataggt gaagctattt gcaaaaaaaa aggagaacac 30420
atgcacacta aaaagataaa actgtagagt cctgttgtca aaatactcaa ttgtccttta 30480
gaccatgtct aactgttcat ttatatgatt ctctaaaaca ctgatattat tgtagtacta 30540
tagattatat tattcgtaga gtaaagttta aatatatgta taaagataga taaactgcac 30600
ttcaaacaag tgtgacaaaa aaaatatgtg gtaatttttt ataacttaga catgcaatgc 30660
tcattatctc tagagagggg cacgaccggg tcacgctgca ctgcaggcat gcaagcttct 30720
gcagaagtaa caccaaacaa cagggtgagc atcgacaaaa gaaacagtac caagcaaata 30780
aatagcgtat gaaggcaggg ctaaaaaaat ccacatatag ctgctgcata tgccatcatc 30840
caagtatatc aagatcaaaa taattataaa acatacttgt ttattataat agataggtac 30900
tcaaggttag agcatatgaa tagatgctgc atatgccatc atgtatatgc atcagtaaaa 30960
cccacatcaa catgtatacc tatcctagat cgatatttcc atccatctta aactcgtaac 31020
tatgaagatg tatgacacac acatacagtt ccaaaattaa taaatacacc aggtagtttg 31080
aaacagtatt ctactccgat ctagaacgaa tgaacgaccg cccaaccaca ccacatcatc 31140
acaaccaagc gaacaaaaag catctctgta tatgcatcag taaaacccgc atcaacatgt 31200
atacctatcc tagatcgata tttccatcca tcatcttcaa ttcgtaacta tgaatatgta 31260

-continued

```
tggcacacac atacagatcc aaaattaata aatccaccag gtagtttgaa acagaattct  31320
actccgatct agaacgaccg cccaaccaga ccacatcatc acaaccaaga caaaaaaaag  31380
catgaaaaga tgacccgaca aacaagtgca cggcatatat tgaaataaag gaaaagggca  31440
aaccaaaccc tatgcaacga aacaaaaaaa atcatgaaat cgatcccgtc tgcggaacgg  31500
ctagagccat cccaggattc cccaaagaga aacactggca agttagcaat cagaacgtgt  31560
ctgacgtaca ggtcgcatcc gtgtacgaac gctagcagca cggatctaac acaaacacgg  31620
atctaacaca aacatgaaca gaagtagaac taccgggccc taaccatgga ccggaacgcc  31680
gatctagaga aggtagagag gggggggggg ggaggacgag cggcgtacct tgaagcggag  31740
gtgccgacgg gtggatttgg gggagatctg gttgtgtgtg tgtgcgctcc gaacaacacg  31800
aggttgggga aagagggtgt ggagggggtg tctatttatt acggcgggcg aggaagggaa  31860
agcgaaggag cggtgggaaa ggaatccccc gtagctgccg gtgccgtgag aggaggagga  31920
ggccgcctgc cgtgccggct cacgtctgcc gctccgccac gcaatttctg gatgccgaca  31980
gcggagcaag tccaacggtg gagcggaact ctcgagaggg gtccagaggc agcgacagag  32040
atgccgtgcc gtctgcttcg cttggcccga cgcgacgctg ctggttcgct ggttggtgtc  32100
cgttagactc gtcgacggcg tttaacaggc tggcattatc tactcgaaac aagaaaaatg  32160
tttccttagt ttttttaatt tcttaaaggg tatttgttta atttttagtc actttatttt  32220
attctatttt atatctaaat tattaaataa aaaaactaaa atagagtttt agttttctta  32280
atttagaggc taaaatagaa taaaatagat gtactaaaaa aattagtcta taaaaaccat  32340
taaccctaaa ccctaaatgg atgtactaat aaaatggatg aagtattata taggtgaagc  32400
tatttgcaaa aaaaaaggag aacacatgca cactaaaaag ataaaactgt agagtcctgt  32460
tgtcaaaata ctcaattgtc ctttagacca tgtctaactg ttcatttata tgattctcta  32520
aaacactgat attattgtag tactatagat tatattattc gtagagtaaa gtttaaatat  32580
atgtataaag atagataaac tgcacttcaa acaagtgtga caaaaaaaat atgtggtaat  32640
tttttataac ttagacatgc aatgctcatt atctctagag aggggcacga ccgggtcacg  32700
ctgcactgca ggcatgcaag cttgcactgg ccgtcgtttt acaacgtcgt gactgggaaa  32760
accctggcgt tacccaactt aatcgccttg cagcacatcc ccctttcgcc agctggcgta  32820
atagcgaaga ggcccgcacc gatcgccctt cccaacagtt gcgcagcctg aatggcgaat  32880
ggcgcctgat gcggtatttt ctccttacgc atctgtgcgg tatttcacac cgcatatggt  32940
gcactctcag tacaatctgc tctgatgccg catagttaag ccagccccga cacccgccaa  33000
cacccgctga cgcgccctga cgggcttgtc tgctcccggc atccgcttac agacaagctg  33060
tgaccgtctc cgggagctgc atgtgtcaga ggttttcacc gtcatcaccg aaacgcgcga  33120
gacgaaaggg cctcgtgata cgcctatttt tataggttaa tgtcatgata ataatggttt  33180
cttagacgtc aggtggcact tttcggggaa atgtgcgcgg aacccctatt tgtttatttt  33240
tctaaataca ttcaaatatg tatccgctca tgagacaata accctgataa atgcttcaat  33300
aatattgaaa aaggaagagt atgagtattc aacatttccg tgtcgccctt attccctttt  33360
ttgcggcatt ttgccttcct gtttttgctc acccagaaac gctggtgaaa gtaaaagatg  33420
ctgaagatca gttgggtgca cgagtgggtt acatcgaact ggatctcaac agcggtaaga  33480
tccttgagag ttttcgcccc gaagaacgtt ttccaatgat gagcactttt aaagttctgc  33540
tatgtggcgc ggtattatcc cgtattgacg ccgggcaaga gcaactcggt cgccgcatac  33600
```

-continued actattctca gaatgacttg gttgagtact caccagtcac agaaaagcat cttacggatg 33660
gcatgacagt aagagaatta tgcagtgctg ccataaccat gagtgataac actgcggcca 33720
acttacttct gacaacgatc ggaggaccga aggagctaac cgcttttttg cacaacatgg 33780
gggatcatgt aactcgcctt gatcgttggg aaccggagct gaatgaagcc ataccaaacg 33840
acgagcgtga caccacgatg cctgtagcaa tggcaacaac gttgcgcaaa ctattaactg 33900
gcgaactact tactctagct tcccggcaac aattaataga ctggatggag gcggataaag 33960
ttgcaggacc acttctgcgc tcggcccttc cggctggctg gtttattgct gataaatctg 34020
gagccggtga gcgtgggtct cgcggtatca ttgcagcact ggggccagat ggtaagccct 34080
cccgtatcgt agttatctac acgacgggga gtcaggcaac tatggatgaa cgaaatagac 34140
agatcgctga gataggtgcc tcactgatta agcattggta actgtcagac caagtttact 34200
catatatact ttagattgat ttaaaacttc atttttaatt taaaaggatc taggtgaaga 34260
tcctttttga taatctcatg accaaaatcc cttaacgtga gttttcgttc cactgagcgt 34320
cagaccccgt agaaaagatc aaaggatctt cttgagatcc tttttttctg cgcgtaatct 34380
gctgcttgca aacaaaaaaa ccaccgctac cagcggtggt ttgtttgccg gatcaagagc 34440
taccaactct ttttccgaag gtaactggct tcagcagagc gcagatacca aatactgtcc 34500
ttctagtgta gccgtagtta ggccaccact tcaagaactc tgtagcaccg cctacatacc 34560
tcgctctgct aatcctgtta ccagtggctg ctgccagtgg cgataagtcg tgtcttaccg 34620
ggttggactc aagacgatag ttaccggata aggcgcagcg gtcgggctga acggggggtt 34680
cgtgcacaca gcccagcttg gagcgaacga cctacaccga actgagatac ctacagcgtg 34740
agctatgaga aagcgccacg cttcccgaag ggagaaaggc ggacaggtat ccggtaagcg 34800
gcagggtcgg aacaggagag cgcacgaggg agcttccagg gggaaacgcc tggtatcttt 34860
atagtcctgt cgggtttcgc cacctctgac ttgagcgtcg atttttgtga tgctcgtcag 34920
gggggcggag cctatggaaa aacgccagca acgcggcctt tttacggttc ctggcctttt 34980
gctggccttt tgctcacatg ttctttcctg cgttatcccc tgattctgtg gataaccgta 35040
ttaccgcctt tgagtgagct gataccgctc gccgcagccg aacgaccgag cgcagcgagt 35100
cagtgagcga ggaagcggaa gagcgcccaa tacgcaaacc gcctctcccc gcgcgttggc 35160
cgattcatta atgcagctgg cacgacaggt ttcccgactg gaaagcgggc agtgagcgca 35220
acgcaattaa tgtgagttag ctcactcatt aggcacccca ggctttacac tttatgcttc 35280
cggctcgtat gttgtgtgga attgtgagcg gataacaatt tcacacagga aacagctatg 35340
accatgatta cgaattccga tcgttcaaac atttggcaat aaagtttctt aagattgaat 35400
cctgttgccg gtcttgcgat gattatcata taatttctgt tgaattacgt taagcatgta 35460
ataattaaca tgtaatgcat gacgttattt atgagatggg tttttatgat tagagtcccg 35520
caattataca tttaatacgc gatagaaaac aaaatatagc gcgcaaacta ggataaatta 35580
tcgcgcgcgg tgtcatctat gttactagat cgatctcggt gacgggcagg accggacggg 35640
gcggtaccgg caggctgaag tccagctgcc agaaacccac gtcatgccag ttcccgtgct 35700
tgaagccggc cgcccgcagc atgccgcggg gggcatatcc gagcgcctcg tgcatgcgca 35760
cgctcgggtc gttgggcagc ccgatgacag cgaccacgct cttgaagccc tgtgcctcca 35820
gggacttcag caggtgggtg tagagcgtgg agcccagtcc cgtccgctgg tggcgggggg 35880
agacgtacac ggtcgactcg gccgtccagt cgtaggcgtt gcgtgccttc caggggcccg 35940
cgtaggcgat gccggcgacc tcgccgtcca cctcggcgac gagccaggga tagcgctccc 36000

-continued gcagacggac gaggtcgtcc gtccactcct gcggttcctg cggctcggta cggaagttga 36060
ccgtgcttgt ctcgatgtag tggttgacga tggtgcagac cgccggcatg tccgcctcgg 36120
tggcacggcg gatgtcggcc gggcgtcgtt ctgggctcat ggatccaagc ttgcatgcct 36180
gcagtgcagc gtgacccggt cgtgcccctc tctagagata atgagcattg catgtctaag 36240
ttataaaaaa ttaccacata tttttttgt cacacttgtt tgaagtgcag tttatctatc 36300
tttatacata tatttaaact ttactctacg aataatataa tctatagtac tacaataata 36360
tcagtgtttt agagaatcat ataaatgaac agttagacat ggtctaaagg acaattgagt 36420
attttgacaa caggactcta cagttttatc tttttagtgt gcatgtgttc tccttttttt 36480
ttgcaaatag cttcacctat ataatacttc atccatttta ttagtacatc catttagggt 36540
ttagggttaa tggtttttat agactaattt ttttagtaca tctattttat tctattttag 36600
cctctaaatt aagaaaacta aaactctatt ttagtttttt tatttaataa tttagatata 36660
aaatagaata aaataaagtg actaaaaatt aaacaaatac cctttaagaa attaaaaaaa 36720
ctaaggaaac atttttcttg tttcgagtag ataatgccag cctgttaaac gccgtcgacg 36780
agtctaacgg acaccaacca gcgaaccagc agcgtcgcgt cgggccaagc gaagcagacg 36840
gcacggcatc tctgtcgctg cctctggacc cctctcgaga gttccgctcc accgttggac 36900
ttgctccgct gtcggcatcc agaaattgcg tggcggagcg gcagacgtga gccggcacgg 36960
caggcggcct cctcctcctc tcacggcacc ggcagctacg gggggattcct ttcccaccgc 37020
tccttcgctt tcccttcctc gcccgccgta ataaatagac acccccctcca caccctcttt 37080
ccccaacctc gtgttgttcg gagcgcacac acacacaacc agatctcccc caaatccacc 37140
cgtcggcacc tccgcttcaa ggtacgccgc tcgtcctccc cccccccccc tctctacctt 37200
ctctagatcg gcgttccggt ccatggttag ggcccggtag ttctacttct gttcatgttt 37260
gtgttagatc cgtgtttgtg ttagatccgt gctgctagcg ttcgtacacg gatgcgacct 37320
gtacgtcaga cacgttctga ttgctaactt gccagtgttt ctctttgggg aatcctggga 37380
tggctctagc cgttccgcag acgggatcga tttcatgatt ttttttgttt cgttgcatag 37440
ggtttggttt gccctttcc tttatttcaa tatatgccgt gcacttgttt gtcgggtcat 37500
cttttcatgc ttttttttgt cttggttgtg atgatgtggt ctggttgggc ggtcgttcta 37560
gatcggagta gaattctgtt tcaaactacc tggtggattt attaattttg gatctgtatg 37620
tgtgtgccat acatattcat agttacgaat tgaagatgat ggatggaaat atcgatctag 37680
gataggtata catgttgatg cgggttttac tgatgcatat acagagatgc tttttgttcg 37740
cttggttgtg atgatgtggt gtggttgggc ggtcgttcat tcgttctaga tcggagtaga 37800
atactgtttc aaactacctg gtgtatttat taattttgga actgtatgtg tgtgtcatac 37860
atcttcatag ttacgagttt aagatggatg gaaatatcga tctaggatag gtatacatgt 37920
tgatgtgggt tttactgatg catatacatg atggcatatg cagcatctat tcatatgctc 37980
taaccttgag tacctatcta ttataataaa caagtatgtt ttataattat tttgatcttg 38040
atatacttgg atgatggcat atgcagcagc tatatgtgga ttttttagc cctgccttca 38100
tacgctattt atttgcttgg tactgtttct tttgtcgatg ctcaccctgt tgtttggtgt 38160
tacttctgca gggatccatg agcccagaac gacgcccggc cgacatccgc cgtgccaccg 38220
aggcggacat gccggcggtc tgcaccatcg tcaaccacta catcgagaca agcacggtca 38280
acttccgtac cgagccgcag gaaccgcagg agtggacgga cgacctcgtc cgtctgcggg 38340

-continued

```
agcgctatcc ctggctcgtc gccgaggtgg acggcgaggt cgccggcatc gcctacgcgg  38400
gcccctggaa ggcacgcaac gcctacgact ggacggccga gtcgaccgtg tacgtctccc  38460
cccgccacca gcggacggga ctgggctcca cgctctacac ccacctgctg aagtccctgg  38520
aggcacaggg cttcaagagc gtggtcgctg tcatcgggct gcccaacgac ccgagcgtgc  38580
gcatgcacga ggcgctcgga tatgcccccc gcggcatgct gcgggcggcc ggcttcaagc  38640
acgggaactg gcatgacgtg ggtttctggc agctggactt cagcctgccg gtaccgcccc  38700
gtccggtcct gcccgtcacc gagatctgat ccgtcgacct gcagatcgtt caaacatttg  38760
gcaataaagt ttcttaagat tgaatcctgt tgccggtctt gcgatgatta tcatataatt  38820
tctgttgaat tacgttaagc atgtaataat taacatgtaa tgcatgacgt tatttatgag  38880
atgggttttt atgattagag tcccgcaatt atacatttaa tacgcgatag aaaacaaaat  38940
atagcgcgca aactaggata aattatcgcg cgcggtgtca tctatgttac tagatcggaa  39000
ttcgtaatca tggtcatagc tgtttcctgt gtgaaattgt tatccgctca caattccaca  39060
caacatacga gccggaagca taaagtgtaa agcctggggt gcctaatgag tgagctaact  39120
cacattaatt gcgttgcgct cactgcccgc tttccagtcg ggaaacctgt cgtgccagct  39180
gcattaatga atcggccaac gcgcggggag aggcggtttg cgtattgggc gctcttccgc  39240
ttcctcgctc actgactcgc tgcgctcggt cgttcggctg cggcgagcgg tatcagctca  39300
ctcaaaggcg gtaatacggt tatccacaga atcaggggat aacgcaggaa agaacatgtg  39360
agcaaaaggc cagcaaaagg ccaggaaccg taaaaaggcc gcgttgctgg cgtttttcca  39420
taggctccgc ccccctgacg agcatcacaa aaatcgacgc tcaagtcaga ggtggcgaaa  39480
cccgacagga ctataaagat accaggcgtt tccccctgga agctccctcg tgcgctctcc  39540
tgttccgacc ctgccgctta ccggatacct gtccgccttt ctcccttcgg gaagcgtggc  39600
gctttctcat agctcacgct gtaggtatct cagttcggtg taggtcgttc gctccaagct  39660
gggctgtgtg cacgaacccc ccgttcagcc cgaccgctgc gccttatccg gtaactatcg  39720
tcttgagtcc aacccggtaa gacacgactt atcgccactg gcagcagcca ctggtaacag  39780
gattagcaga gcgaggtatg taggcggtgc tacagagttc ttgaagtggt ggcctaacta  39840
cggctacact agaaggacag tatttggtat ctgcgctctg ctgaagccag ttaccttcgg  39900
aaaaagagtt ggtagctctt gatccggcaa acaaaccacc gctggtagcg gtggtttttt  39960
tgtttgcaag cagcagatta cgcgcagaaa aaaaggatct caagaagatc ctttgatctt  40020
ttctacgggg tctgacgctc agtggaacga aaactcacgt taagggattt tggtcatgag  40080
attatcaaaa aggatcttca cctagatcct tttaaattaa aaatgaagtt ttaaatcaat  40140
ctaaagtata tatgagtaaa cttggtctga cagttaccaa tgcttaatca gtgaggcacc  40200
tatctcagcg atctgtctat ttcgttcatc catagttgcc tgactccccg tcgtgtagat  40260
aactacgata cgggagggct taccatctgg ccccagtgct gcaatgatac cgcgagaccc  40320
acgctcaccg gctccagatt tatcagcaat aaaccagcca gccggaaggg ccgagcgcag  40380
aagtggtcct gcaactttat ccgcctccat ccagtctatt aattgttgcc gggaagctag  40440
agtaagtagt tcgccagtta atagtttgcg caacgttgtt gccattgcta caggcatcgt  40500
ggtgtcacgc tcgtcgtttg gtatggcttc attcagctcc ggttcccaac gatcaaggcg  40560
agttacatga tcccccatgt tgtgcaaaaa agcggttagc tccttcggtc ctccgatcgt  40620
tgtcagaagt aagttggccg cagtgttatc actcatggtt atggcagcac tgcataattc  40680
tcttactgtc atgccatccg taagatgctt ttctgtgact ggtgagtact caaccaagtc  40740
```

attctgagaa tagtgtatgc ggcgaccgag ttgctcttgc ccggcgtcaa tacgggataa 40800
taccgcgcca catagcagaa ctttaaaagt gctcatcatt ggaaaacgtt cttcggggcg 40860
aaaactctca aggatcttac cgctgttgag atccagttcg atgtaaccca ctcgtgcacc 40920
caactgatct tcagcatctt ttactttcac cagcgtttct gggtgagcaa aaacaggaag 40980
gcaaaatgcc gcaaaaaagg gaataagggc gacacggaaa tgttgaatac tcatactctt 41040
cctttttcaa tattattgaa gcatttatca gggttattgt ctcatgagcg gatacatatt 41100
tgaatgtatt tagaaaaata aacaaatagg ggttccgcgc acatttcccc gaaaagtgcc 41160
acctgacgtc taagaaacca ttattatcat gacattaacc tataaaaata ggcgtatcac 41220
gaggcccttt cgtctcgcgc gtttcggtga tgacggtgaa aacctctgac acatgcagct 41280
cccggagacg gtcacagctt gtctgtaagc ggatgccggg agcagacaag cccgtcaggg 41340
cgcgtcagcg ggtgttggcg ggtgtcgggg ctggcttaac tatgcggcat cagagcagat 41400
tgtactgaga gtgcaccata tgcggtgtga aataccgcac agatgcgtaa ggagaaaata 41460
ccgcatcagg cgccattcgc cattcaggct gcgcaactgt tgggaagggc gatcggtgcg 41520
ggcctcttcg ctattacgcc agctggcgaa agggggatgt gctgcaaggc gattaagttg 41580
ggtaacgcca gggttttccc agtcacgacg ttgtaaaacg acggccagtg caagcttgca 41640
tgcctgcagt gcagcgtgac ccggtcgtgc ccctctctag agataatgag cattgcatgt 41700
ctaagttata aaaaattacc acatattttt tttgtcacac ttgtttgaag tgcagtttat 41760
ctatctttat acatatattt aaactttact ctacgaataa tataatctat agtactacaa 41820
taatatcagt gttttagaga atcatataaa tgaacagtta gacatggtct aaaggacaat 41880
tgagtatttt gacaacagga ctctacagtt ttatcttttt agtgtgcatg tgttctcctt 41940
ttttttgca aatagcttca cctatataat acttcatcca ttttattagt acatccattt 42000
agggtttagg gttaatggtt tttatagact aattttttta gtacatctat tttattctat 42060
tttagcctct aaattaagaa aactaaaact ctattttagt ttttttattt aataatttag 42120
atataaaata gaataaaata aagtgactaa aaattaaaca aataccottt aagaaattaa 42180
aaaaactaag gaaacatttt tcttgtttcg agtagataat gccagcctgt taaacgccgt 42240
cgacgagtct aacggacacc aaccagcgaa ccagcagcgt cgcgtcgggc caagcgaagc 42300
agacggcacg gcatctctgt cgctgcctct ggacccctct cgagagttcc gctccaccgt 42360
tggacttgct ccgctgtcgg catccagaaa ttgcgtggcg gagcggcaga cgtgagccgg 42420
cacggcaggc ggcctcctcc tcctctcacg gcaccggcag ctacggggga ttcctttccc 42480
accgctcctt cgctttccct tcctcgcccg ccgtaataaa tagacacccc ctccacaccc 42540
tctttcccca acctcgtgtt gttcggagcg cacacacaca caaccagatc tcccccaaat 42600
ccacccgtcg gcacctccgc ttcaaggtac gccgctcgtc ctcccccccc cccctctct 42660
accttctcta gatcggcgtt ccggtccatg gttagggccc ggtagttcta cttctgttca 42720
tgtttgtgtt agatccgtgt ttgtgttaga tccgtgctgc tagcgttcgt acacggatgc 42780
gacctgtacg tcagacacgt tctgattgct aacttgccag tgtttctctt tggggaatcc 42840
tgggatggct ctagccgttc cgcagacggg atcgatttca tgattttttt tgtttcgttg 42900
catagggttt ggtttgccct tttcctttat ttcaatatat gccgtgcact tgtttgtcgg 42960
gtcatctttt catgcttttt tttgtcttgg ttgtgatgat gtggtctggt tgggcggtcg 43020
ttctagatcg gagtagaatt ctgtttcaaa ctacctggtg gatttattaa ttttggatct 43080

-continued

```
gtatgtgtgt gccatacata ttcatagtta cgaattgaag atgatggatg gaaatatcga  43140
tctaggatag gtatacatgt tgatgcgggt tttactgatg catatacaga gatgcttttt  43200
gttcgcttgg ttgtgatgat gtggtgtggt tgggcggtcg ttcattcgtt ctagatcgga  43260
gtagaatact gtttcaaact acctggtgta tttattaatt ttggaactgt atgtgtgtgt  43320
catacatctt catagttacg agtttaagat ggatggaaat atcgatctag gataggtata  43380
catgttgatg tgggttttac tgatgcatat acatgatggc atatgcagca tctattcata  43440
tgctctaacc ttgagtacct atctattata ataaacaagt atgttttata attattttga  43500
tcttgatata cttggatgat ggcatatgca gcagctatat gtggattttt ttagccctgc  43560
cttcatacgc tatttatttg cttggtactg tttcttttgt cgatgctcac cctgttgttt  43620
ggtgttactt ctgcaggtcg actctagagg atccatcgat taggaagtaa ccatgagccc  43680
agaacgacgc ccggccgaca tccgccgtgc caccgaggcg gacatgccgg cggtctgcac  43740
catcgtcaac cactacatcg agacaagcac ggtcaacttc cgtaccgagc cgcaggaacc  43800
gcaggagtgg acggacgacc tcgtccgtct gcgggagcgc tatccctggc tcgtcgccga  43860
ggtggacggc gaggtcgccg gcatcgccta cgcgggcccc tggaaggcac gcaacgccta  43920
cgactggacg gccgagtcga ccgtgtacgt ctcccccgc caccagcgga cgggactggg  43980
ctccacgctc tacacccacc tgctgaagtc cctggaggca cagggcttca agagcgtggt  44040
cgctgtcatc gggctgccca acgacccgag cgtgcgcatg cacgaggcgc tcggatatgc  44100
cccccgcggc atgctgcggg cggccggctt caagcacggg aactggcatg acgtgggttt  44160
ctggcagctg gacttcagcc tgccggtacc gccccgtccg gtcctgcccg tcaccgagat  44220
ctgatccgtc gacctgcaga tcgttcaaac atttggcaat aaagtttctt aagattgaat  44280
cctgttgccg gtcttgcgat gattatcata taatttctgt tgaattacgt taagcatgta  44340
ataattaaca tgtaatgcat gacgttattt atgagatggg tttttatgat tagagtcccg  44400
caattataca tttaatacgc gatagaaaac aaaatatagc gcgcaaacta ggataaatta  44460
tcgcgcgcgg tgtcatctat gttactagat cggaattcgt aatcatggtc atagctgttt  44520
cctgtgtgaa attgttatcc gctcacaatt ccacacaaca tacgagccgg aagcataaag  44580
tgtaaagcct ggggtgccta atgagtgagc taactcacat taattgcgtt gcgctcactg  44640
cccgctttcc agtcgggaaa cctgtcgtgc cagctgcatt aatgaatcgg ccaacgcgcg  44700
gggagaggcg gtttgcgtat tgggcgctct tccgcttcct cgctcactga ctcgctgcgc  44760
tcggtcgttc ggctgcggcg agcggtatca gctcactcaa aggcggtaat acggttatcc  44820
acagaatcag gggataacgc aggaaagaac atgtgagcaa aaggccagca aaaggccagg  44880
aaccgtaaaa aggccgcgtt gctggcgttt ttccataggc tccgcccccc tgacgagcat  44940
cacaaaaatc gacgctcaag tcagaggtgg cgaaacccga caggactata aagataccag  45000
gcgtttcccc ctggaagctc cctcgtgcgc tctcctgttc cgaccctgcc gcttaccgga  45060
tacctgtccg cctttctccc ttcgggaagc gtggcgcttt ctcatagctc acgctgtagg  45120
tatctcagtt cggtgtaggt cgttcgctcc aagctgggct gtgtgcacga accccccgtt  45180
cagcccgacc gctgcgcctt atccggtaac tatcgtcttg agtccaaccc ggtaagacac  45240
gacttatcgc cactggcagc agccactggt aacaggatta gcagagcgag gtatgtaggc  45300
ggtgctacag agttcttgaa gtggtggcct aactacggct acactagaag gacagtattt  45360
ggtatctgcg ctctgctgaa gccagttacc ttcggaaaaa gagttggtag ctcttgatcc  45420
ggcaaacaaa ccaccgctgg tagcggtggt ttttttgttt gcaagcagca gattacgcgc  45480
```

-continued

```
agaaaaaaag gatctcaaga agatcctttg atcttttcta cggggtctga cgctcagtgg  45540

aacgaaaact cacgttaagg gattttggtc atgagattat caaaaaggat cttcacctag  45600

atccttttaa attaaaaatg aagttttaaa tcaatctaaa gtatatatga gtaaacttgg  45660

tctgacagtt accaatgctt aatcagtgag gcacctatct cagcgatctg tctatttcgt  45720

tcatccatag ttgcctgact ccccgtcgtg tagataacta cgatacggga gggcttacca  45780

tctggcccca gtgctgcaat gataccgcga gacccacgct caccggctcc agatttatca  45840

gcaataaacc agccagccgg aagggccgag cgcagaagtg gtcctgcaac tttatccgcc  45900

tccatccagt ctattaattg ttgccgggaa gctagagtaa gtagttcgcc agttaatagt  45960

ttgcgcaacg ttgttgccat tgctacaggc atcgtggtgt cacgctcgtc gtttggtatg  46020

gcttcattca gctccggttc ccaacgatca aggcgagtta catgatcccc catgttgtgc  46080

aaaaaagcgg ttagctcctt cggtcctccg atcgttgtca gaagtaagtt ggccgcagtg  46140

ttatcactca tggttatggc agcactgcat aattctctta ctgtcatgcc atccgtaaga  46200

tgcttttctg tgactggtga gtactcaacc aagtcattct gagaatagtg tatgcggcga  46260

ccgagttgct cttgcccggc gtcaatacgg gataataccg cgccacatag cagaacttta  46320

aaagtgctca tcattggaaa acgttcttcg gggcgaaaac tctcaaggat cttaccgctg  46380

ttgagatcca gttcgatgta acccactcgt gcacccaact gatcttcagc atcttttact  46440

ttcaccagcg tttctgggtg agcaaaaaca ggaaggcaaa atgccgcaaa aaagggaata  46500

agggcgacac ggaaatgttg aatactcata ctcttccttt ttcaatatta ttgaagcatt  46560

tatcagggtt attgtctcat gagcggatac atatttgaat gtatttagaa aaataaacaa  46620

ataggggttc cgcgcacatt tccccgaaaa gtgccacctg acgtctaaga aaccattatt  46680

atcatgacat taacctataa aaataggcgt atcacgaggc cctttcgtct cgcgcgtttc  46740

ggtgatgacg gtgaaaacct ctgacacatg cagctcccgg agacggtcac agcttgtctg  46800

taagcggatg ccgggagcag acaagcccgt cagggcgcgt cagcgggtgt tggcgggtgt  46860

cggggctggc ttaactatgc ggcatcagag cagattgtac tgagagtgca ccatatgcgg  46920

tgtgaaatac cgcacagatg cgtaaggaga aaataccgca tcaggcgcca ttcgccattc  46980

aggctgcgca actgttggga agggcgatcg gtgcgggcct cttcgctatt acgccagctg  47040

gcgaaagggg gatgtgctgc aaggcgatta agttgggtaa cgccagggtt ttcccagtca  47100

cgacgttgta aaacgacggc cagtgc                                      47126
```

<210> SEQ ID NO 2
<211> LENGTH: 19598
<212> TYPE: DNA
<213> ORGANISM: Artificial Sequence
<220> FEATURE:
<223> OTHER INFORMATION: Short insert without flanking regions

<400> SEQUENCE: 2

```
ttggaacacc acgatgcctg tagcaatggc aacaacgttg cgcaaactat taactggcga     60

actacttact ctagcttccc ggtaacaatt aatagactgg atggaggcgg ataaagttgt    120

aggaccactt ctgcgctcgg cccttccggc tggctggttt attgctgata aatctggagc    180

cggactctag gcttcccggg caacaaatta attagactgg atggagggat aaagtttgca    240

gaccactttc tgcgctcggc ccttccgctg ggctgttcta tgcccgctga aatcaccagt    300

ctctctctac aaatctatct ctctctataa taatgtgtga gtagttccca gataagggaa    360
```

-continued

```
ttagggttct tatagggttt cgctcatgtg ttgagcatat aagaaaccct tagtatgtat    420
ttgtatttgg gctggcttaa ctatgcggca tcagagcaga ttgtactgag agtgcaccat    480
atgcggtgtg aaataccgca cagatgcgta aggagaaaat accgcatcag gcgccattcg    540
ccattcaggc tgcgcaactg ttgggaaggg cgatcggtgc gggcctcttc gctattacgc    600
cagctggcga aagggggatg tgctgcaagg cgattaagtt gggtaacgcc agggttttcc    660
cagtcacgac gttgtaaaac gacggccagt gcaagcttgc atgcctgcag tgcagcgtga    720
cccggtcgtg cccctctcta gagataatga gcattgcatg tctaagttat aaaaaattac    780
cacatatttt ttttgtcaca cttgtttgaa gtgcagttta tctatcttta tacatatatt    840
taaactttac tctacgaata atataatcta tagtactaca ataatatcag tgttttagag    900
aatcatataa atgaacagtt agacatggtc taaaggacaa ttgagtattt tgacaacagg    960
actctacagt tttatctttt tagtgtgcat gtgttctcct ttttttttgc aaatagcttc   1020
acctatataa tacttcatcc attttattag tacatccatt tagggtttag ggttaatggt   1080
ttttatagac taattttttt agtacatcta ttttattcta ttttagcctc taaattaaga   1140
aaactaaaac tctattttag ttttttttatt taataattta gatataaaat agaataaaat   1200
aaagtgacta aaaattaaac aaataccctt taagaaatta aaaaaactaa ggaaacattt   1260
ttcttgtttc gagtagataa tgccagcctg ttaaacgccg tcgacgagtc taacggacac   1320
caaccagcga accagcagcg tcgcgtcggg ccaagcgaag cagacggcac ggcatctctg   1380
tcgctgcctc tggacccctc tcgagagttc cgctccaccg ttggacttgc tccgctgtcg   1440
gcatccagaa attgcgtggc ggagcggcag acgtgagccg gcacggcagg cggcctcctc   1500
ctcctctcac ggcaccggca gctacggggg attcctttcc caccgctcct tcgctttccc   1560
ttcctcgccc gccgtaataa atagacaccc cctccacacc ctctttcccc aacctcgtgt   1620
tgttcggagc gcacacacac acaaccagat ctccccccaaa tccacccgtc ggcgtacgcc   1680
gctcgtcctc cccccccccc cctctctacc ttctctagat cggcgttccg gtccatggtt   1740
agggcccggt agttctactt ctgttcatgt ttgtgttaga tccgtgtttg tgttagatcc   1800
gtgctgctag cgttcgtaca cggatgcgac ctgtacgtca gacacgttct gattgctaac   1860
ttgccagtgt ttctctttgg ggaatcctgg gatggctcta gccgttccgc agacgggatc   1920
gatttcatga ttttttttgt ttcgttgcat agggtttggt ttgccctttt cctttatttc   1980
aatatatgcc gtgcacttgt ttgtcgggtc atcttttcat gctttttttt gtcttcctgt   2040
ttttgctcac ccagaaacgc tggtgaaagt aaaagatgct gaagatcagt tgggtgcacg   2100
agtgggttac atcgaactgg atctcaacag cggtaagatc cttgagagtt ttcgccccga   2160
agaacgtttt ccaatgatga gcacttttaa agttctgcta tgtggcgcgg tattatcccg   2220
tattgacgcc gggcaagagc aactcggtcg ccgcatacac tattctcaga atgacttggt   2280
tgagtactca ccagtcacag aaaagcatct tacggatggc atgacagtaa gagaattatg   2340
cagtgctgcc ataaccatga gtgataacac tgcggccaac ttacttctga caacgatcgg   2400
aggaccgaag gagctaaccg cttttttgca caacatgggg gatcatgtaa ctcgccttga   2460
tcgttgggaa ccggagctga atgaagccat accaaacgac gagcgtgaca ccacgatgcc   2520
tgtagcaatg gcaacaacgt tgcgcaaact attaactgtt attgccggga aaagtgtacg   2580
tatcaccgtt tgtgtgaaca acgaactgaa ctggcagact atcccctgca gaagtaacac   2640
caaacaacag ggtgagcatc gacaaaagaa acagtaccaa gcaaataaat agcgtatgaa   2700
ggcagggcta aaaaaatcca catatagctg ctgcatatgc catcatccaa gtatatcaag   2760
```

-continued

```
atcaaaataa ttataaaaca tacttgttta ttataataga taggtactca aggttagagc   2820
atatgaatag atgctgcata tgccatcatg tatatgcatc agtaaaaccc acatcaacat   2880
gtatacctat cctagatcga tatttccatc catcttaaac tcgtaactat gaagatgtat   2940
gacacacaca tacagttcca aaattaataa atacaccagg tagtttgaaa cagtattcta   3000
ctccgatcta gaacgaatga acgaccgccc aaccacacca catcatcaca accaagcgaa   3060
caaaaagcat ctctgtatat gcatcagtaa aacccgcatc aacatgtata cctatcctag   3120
aagtactata gattatatta ttcgtagagt aaagtttaaa tatatgtata aagatagata   3180
aactgcactt caaacaagtg tgacaaaaaa aatatgtggt aatttttat aacttagaca   3240
tgcaatgctc attatctcta gagaggggca cgaccgggtc acgctgcact gcaggcatgc   3300
aagcttggca ctggccgtcg ttttacaacg tcgtgactgg gaaaaccctg gcgttaccca   3360
acttaatcgc cttgcagcac atcccccttt cgccagctgg cgtaatagcg aagaggcccg   3420
caccgatcgc ccttcccaac agttgcgcag cctgaatggc gaatggcgcc tgatgcggta   3480
ttttctcctt acgcatctgt gcggtatttc acaccgcata tggtgcactc tcagtacaat   3540
ctgctctgat gccgcatagt taagccagcc ccgacacccg ccaacacccg ctgacgcgcc   3600
ctgacgggct tgtctgctcc cggcatccgc ttacagacaa gctgtgaccg tctccgggag   3660
ctgcatgtgt cagaggtttt caccgtcatc accgaaacgc gcgagacgaa agggcctcgt   3720
gatacgccta tttttatagg ttaatgtcat gataataatg gtttcttaga cgtcaggtgg   3780
cacttttcgg ggaaatgtgc gcggaacccc tatttgttta tttttctaaa tacattacca   3840
atgcttaatc agtgaggcac ctatctcagc gatctgtcta tttcgttcat ccatagttgc   3900
ctgactcccc gtcgtgtaga taactacgat acgggagggc ttaccatctg gccccagtgc   3960
tgcaatgata ccgcgagacc cacgctcacc ggctccagat ttatcagcaa taaaccagcc   4020
agccggaagg gccgagcgca gaagtggtcc tgcaacttta tccgcctcca tccagtctat   4080
taattgttgc cgggaagcta gagtaagtag ttcgccagtt aatagtttgc gcaacgttgt   4140
tgccattgct acaggcatcg tggtgtcacg ctcgtcgttt ggtatggctt cattcagctc   4200
cggttcccaa cgatcaaggc gagttacatg atcccccatg ttgtgcaaaa aagcggttag   4260
ctccttcggt cctccgatcg ttgtcagaag taagttggcc gcagtgttat cactcatggt   4320
tatggcagca ctgcataatt ctcttactgt catgccatcc gtaagatgct tttctgtgac   4380
tggtgagtac tcaaccaagt cattctgaga atagtgtatg cggcgaccga gttgctcttg   4440
cccggcgtca atacgggata ataccgcgcc acatagcaga actttaaaag tgctcatcat   4500
tggaaaacgt tcttcggggc gaaaactctc aaggatctta ccgctgttga gatccagttc   4560
gatgtaaccc actcgtgcac ccaactgatc ttcagcatct tttactttca ccagcgtttc   4620
tgggtgagca aaaacaggaa ggcaaaatgc cgcaaaaaag ggaataaggg cgacacggaa   4680
atgttgaata ctcatactct tcctttttca atattattga agcatttatc agggttattg   4740
tctcatgagc ggatacatat ttgaaaactg tcagaccaag tttactcata tatactttag   4800
attgatttaa aacttcattt ttaatttaaa aggatctagg tgaagatcct ttttgataat   4860
ctcatgacca aaatccctta acgtgagttt tcgttccact gagcgtcaga ccccgtagaa   4920
aagatcaaag gatcttcttg agatcctttt tttctgcgcg taagccaata gaaggcagaa   4980
accctagccg tcatttttct tgaagaatat agagcgacgt cgataggaag atacttaaat   5040
gttgaatcca agcacctaga ataatgagtt agattagaag aaaactatca acttcgaaat   5100
```

-continued

```
caagaagaaa tgttttattc tgttgcataa aactttcgcg tggagaagct ctgttcagag   5160
cccgggtagc cactgggcac gtctcctaga tactggactc atcggacgct ctcctcgagt   5220
tgtccatcga gctctgtacc aagcaccgca tcgcaatcca ctcaaccagc tccgccgcga   5280
gcaggagcgc tccacgacac gcgacgccca agctggcacg cacctcgccg atggcccgat   5340
aagcacggcc gtgcgacgtg gcggcccgcc tcccctctgg cacgcagctc cctccacgt    5400
agccgcgcca gggcgccacg tacagcggcg cgcgcgctac aaatacggtg ccccgagctc   5460
cattccccag caccagcaga gtcacacaca ctgagcgagc taaaccatca ggaagtgatg   5520
gagcatcagg gcggctatac gccatttgaa gccgatgtca cgccgtatgt tattgccggg   5580
aaaagtgtac gtatcaccgt ttgtgccgga atccatcgca gcgtaatgct ctacaccacg   5640
ccgaacacct gggtggacga tatcaccgtg gtgacgcatg tcgcgcaaga ctgtaaccac   5700
gcgtctgttg actggcaggt ggtggccaat ggtgatgtca gcgttgaact gcgtgatgcg   5760
gatcaacagg tggttgcaac tggacaaggc actagcggga ctttgcaagt ggtgaatccg   5820
cacctctggc aaccgggtga aggttatctc tatgaactgt gcgtcacagc caaaagccag   5880
acagagtgtg atatctaccc gcttcgcgtc ggcatccggt cagtggcagt gaagggcgaa   5940
cagttcctga ttaaccacaa accgttctac tttactggct ttggtcgtca tgaagatgcg   6000
gacttgcgtg gcaaaggatt cgataacgtg ctgttaccaa tgcttaatca gtgaggcacc   6060
tatctcagcg atctgtctat ttcgttcatc catagttgcc tgactccccg tcgtgtagat   6120
aactacgata cgggagggct taccatctgg ccccagtgct gcaatgatac cgcgagaccc   6180
acgctcaccg gctccagatt tatcagcaat aaaccagcca gccggaaggg ccgagcgcag   6240
aagtggtcct gcaactttat ccgcctccat ccagtctatt aattgttgcc gggaagctag   6300
agtaagtagt tcgccagtta atagtttgcg caacgttgtt gccattgcta caggcatcgt   6360
ggtgtcacgc tcgtcgtttg gtatggcttc attcagctcc ggttcccaac gatcaaggcg   6420
agttacatga tcccccatgt tgtgcaaaaa agcggttagc tccttcggtc ctccgatcgt   6480
tgtcagaagt aagttggccg cagtgttatc actcatggtt atggcagcac tgcataattc   6540
tcttactgtc atgccatccg taagatgctt ttctgtgact ggtgagtact caaccaagtc   6600
attctgagaa tagtgtatgc ggcgaccgag ttgctcttgc ccggcgtcaa tacgggataa   6660
taccgcgcca catagcagaa ctttaaaagt gctcatcatt ggaaaacgtt cttcggggcg   6720
aaaactctca aggatcttac cgctgttgag atccagttcg atgtaaccca ctcgtgcacc   6780
caactgatct tcagcatctt ttactttcac cagcgtttct gggtgagcaa aaacaggaag   6840
gcaaaatgcc gcaaaaaagg gaataagggc gacacggaaa tgttgaatac tcatactctt   6900
cctttttcaa tattattgaa gcatttatca gggttattgt ctcatgagcg gatacatatt   6960
tgaatgtatt tagaaaaata aacaaatagg ggttccgcgc acatttcccc gaaaagtgcc   7020
acctgacgtc taagaaacca ttattatcat gacattaacc tataaaaata ggcgtatcac   7080
gaggcccttt cgtctcgcgc gtttcggtga tgacggtgaa aacctctgac acatgcagct   7140
cccggagacg gtcacagctt gtctgtaagc ggatgccggg agcagacaag cccgtcaggg   7200
cgcgtcagcg ggtgttggcg ggtgtcgggg ctggcttaac tatgcggcat cagagcagat   7260
tgtactgaga gtgcaccata tgcggtgtga aataccgcac agatgcgtaa ggagaaaata   7320
ccgcatcagg cgccattcgc cattcaggct gcgcaactgt tgggaagggc gatcggtgcg   7380
ggcctcttcg ctattacgcc agctggcgaa agggggatgt gctgcaaggc gattaagttg   7440
ggtaacgcca gggttttccc agtcacgacg ttgtaaaacg acggccagtg caagcttgca   7500
```

tgcctgcagt gcagcgtgac ccggtcgtgc ccctctctag agataatgag cattgcatgt 7560
ctaagttata aaaaattacc acatattttt tttgtcacac ttgtttgaag tgcagtttat 7620
ctatctttat acatatattt aaactttact ctacgaataa tataatctat agtactacaa 7680
taatatcagt gttttagaga atcatataaa tgaacagtta gacatggtct aaaggacaat 7740
tgagtatttt gacaacagga ctctacagtt ttatcttttt agtgtgcatg tgttctcctt 7800
tttttttgca aatagcttca cctatataat acttcatcca ttttattagt acatccattt 7860
agggtttagg gttaatggtt tttatagact aatttttta gtacatctat tttattctat 7920
tttagcctct aaattaagaa aactaaaact ctattttagt ttttttattt aataatttag 7980
atataaaata gaataaaata aagtgactaa aaattaaaca aataccettt aagaaattaa 8040 aaaaactaag gaaacatttt tcttgtttcg agtagataat gccagcctgt taaacgccgt 8100
cgacgagtct aacggacacc aaccagcgaa ccagcagcgt cgcgtcgggc caagcgaagc 8160
agacggcacg gcatctctgt ctgaatagaa tacaaaccct agaaaaacaa ggcacatctc 8220
ggcgccgcca atagaaggca gaaaccctag ccgtcatttt tcttgaagaa tatagagcga 8280
cgtcgatagg aagatactta aatgttgaat ccaagcacct agaataatga gttagattag 8340
aagaaaacta tcaacttcga aatcaagaag aaatgtttta ttctgttgca taaaactttc 8400
gcgtggagaa gctctgttca gagcccgggt agccactggg cacgtctcct agatactgga 8460
ctcatcggac gctctcctcg agttgtccat cgagctctgt accaagcacc gcatcgcaat 8520
ccactcaacc agctccgccg cgagcaggag cgctccacga cacgcgacgc ccaagctggc 8580
acgcacctcg ccgatggccc gataagcacg gccgtgcgac gtggcggccc gcctcccctc 8640
tggcacgcag ctcccctcca cgtagccgcg ccagggcgcc acgtacagcg gcgcgcgcgc 8700
tacaaatacg gtgccccgag ctccattccc cagcaccagc agagtcacac acactgagcg 8760
agctaaacca tggtatagcc gccctgatgc tccatcactt cctgattatt gacccacact 8820
ttgccgtaat gagtgaccgc atcgaaacgc agcacgatac gctggcctgc ccaacctttc 8880
ggtataaaga cttcgcgctg ataccagacg ttgcccgcat aattacgaat atctgcatcg 8940
gcgaactgat cgttaaaact gcctggcaca gcaattgccc ggctttcttg taacgcgctt 9000
tcccaccaac gctgatcaat tccacagttt tcgcgatcca gactgaatgc ccacaggccg 9060
tcgagttttt tgatttcacg ggttggggtt tctacaggac gctattaatt gttgccggga 9120
agctagagta agtagttcgc cagttaatag tttgcgcaac gttgttgcca ttgctacagg 9180
catcgtggtg tcacgctcgt cgtttggtat ggcttcattc agctccggtt cccaacgatc 9240
aaggcgagtt acatgatccc ccatgttgtg caaaaaagcg gttagctcct tcggtcctcc 9300
gatcgttgtc agaagtaagt tggccgcagt gttatcactc atggttcact gtcagaccaa 9360
gtttactcat atatacttta gattgattta aaacttcatt tttaatttaa aaggatctag 9420
gtgaagatcc tttttgataa tctcatgacc aaaatccctt aacgtgagtt ttcgttccac 9480
tgagcgtcag accccgtaga aaagatcaaa ggatcttctt gagatccttt ttttctgcgc 9540
gtaatctgct gcttgcaaac aaaaaaacca ccgctaccag cggtggtttg tttgccggat 9600
caagagctac caactctttt tccgaaggta actggcttca gcagagcgca gataccaaat 9660
actgtccttc tagtgtagcc gtagttaggc caccacttca agaactctgt agcaccgcct 9720
acatacctcg ctctgctaat cctgttacca gtggctgctg ccagtggcga taagtcgtgt 9780
cttaccgggt tggactcaag acgatagtta ccggataagg cgcagcggtc gggctgaacg 9840

-continued

```
gggggttcgt gcacacagcc cagcttggag cgaacgacct acaccgaact gagataccta   9900
cagcgtgagc tatgagaaag cgccacgctt cccgaaggga gaaaggcgga caggtatccg   9960
gtaagcggca gggtcggaac aggagagcgc acgagggagc ttccaggggg aaacgcctgg  10020
tatctttata gtcctgtcgg gtttcgccac ctctgacttg agcgtcgatt tttgtgatgc  10080
tcgtcagggg ggcggagcct atggaaaaac gccagcaacg cggccttttt acggttcctg  10140
gccttttgct ggccttttgc tcacatgttc tttcctgcgt tatcccctga ttctgtggat  10200
aaccgtatta ccgcctttga gtgagctgat accgctcgcc gcagccgaac gaccgagcgc  10260
agcgagtcag tgagcgagga agcggaagag cgcccaatac gcaaaccgcc tctccccgcg  10320
cgttggccga ttcattaatg cagctggcac gacaggtttc ccgactggaa agcgggcagt  10380
gagcgcaacg caattaatgt gagttagctc actcattagg caccccaggc tttacacttt  10440
atgcttccgg ctcgtatgtt gtgtggaatt gtgagcggat aacaatttca cacaggaaac  10500
agctatgacc atgattacga attccgatct agtaacatag atgacaccgc gcgcgataat  10560
ttatcctagt ttgcgcgcta tattttgttt tctatcgcgt attaaatgta taattgcggg  10620
actctaatca taaaaaccca tctcataaat aacgtcatgc attacatgtt aattattaca  10680
tgcttaacgt aattcaacag aaattatatg ataatcatcg caagaccggc aacaggattc  10740
aatcttaaga aactttattg ccaaatgttt gaacgatctg caggtcgacg gatcagatct  10800
cggtgacggg caggaccgga cggggcggta ccggcaggct gaagtccagc tgccagaaac  10860
ccacgtcatg ccagttcccg tgcttgaagc cggccgcccg cagcatgccg cggggggcat  10920
atccgagcgc ctcgtgcatg cgcacgctcg ggtcgttggg cagcccgatg acagcgacca  10980
cgctcttgaa gccctgtgcc tccagggact tcagcaggtg ggtgtagagc gtggagccca  11040
gtcccgtccg ctggtggcgg ggggagacgt acacggtcga ctcggccgtc cagtcgtagg  11100
cgttgcgtgc cttccagggg cccgcgtagg cgatgccggc gacctcgccg tccacctcgg  11160
cgacgagcca gggatagcgc tcccgcagac ggacgaggtc gtccgtccac tcctgcggtt  11220
cctgcggctc ggtacggaag ttgaccgtgc ttgtctcgat gtagtggttg acgatggtgc  11280
agaccgccgg catgtccgcc tcggtggcac ggcggatgtc ggccgggcgt cgttctgggc  11340
tcatggatcc agctccgccg cgagcaggag cgctccacga cacgcgacgc ccaagctggc  11400
acgcacctcg ccgatggccc gataaggcag agcgaggtat gtaggcggtg ctacagagtt  11460
cttgaagtgg tggcctaact acggctacac tagaaggaca gtatttggta tctgcgctct  11520
gctgaagcca gttaccttcg gaaaaagagt tggtagctct tgatccggca aacaaaccac  11580
cgctggtagc ggtggttttt ttgtttgcaa gcagcagatt acgcgcagaa aaaaaggatc  11640
tcaagaagat cctttgatct tttctacggg gtctgacgct cagtggaacg aaaactcacg  11700
ttaagggatt ttggtcatga gattatcaaa aaggatcttc acctagatcc ttttaaatta  11760
aaaatgaagt tttaaatcaa tctaaagtat atatgagtaa acttggtctg acagttacca  11820
atgcttaatc agtgaggcac ctatctcagc gatctgtcta tttcgttcat ccatagttgc  11880
ctgactcccc gtcgtgtaga taactacgat acgggagggc ttaccatctg gccccagtgc  11940
tgcaatgata ccgcgagacc cacgctcacc ggctccagat ttatcagcaa taaaccagcc  12000
agccggaagg gccgagcgca gaagtggtcc tgcaacttta tccgcctcca tccagtctat  12060
taattgttgc cgggaagcta gagtaagtag ttcgccagtt aatagtttgc gcaacgttgt  12120
tgccattgct acaggcatcg tggtgtcacg ctcgtcgttt ggtatggctt cattcagctc  12180
cggttcccaa cgatcaaggc gagttacatg atcccccatg ttgtgcaaaa aagcggttag  12240
```

-continued ctccttcggt cctccgatcg ttgtcagaag taagttggcc gcagtgttat cactcatggt 12300
tatggcagca ctgcataatt ctcttactgt catgccatcc gtaagatgct tttctgtgac 12360
tggtgagtac tcaaccaagt cattctgaga atagtgtatg cggcgaccga gttgctcttg 12420
cccggcgtca atacgggata ataccgcgcc acatagcaga actttaaaag tgctcatcat 12480
tggaaaacgt tcttcggggc gaaaactctc aaggatctta ccgctgttga gatccagttc 12540
gatgtaaccc actcgtgcac ccaactgatc ttcagcatct tttactttca ccagcgtttc 12600
tgggtgagca aaaacaggaa ggcaaaatgc cgcaaaaaag ggaataaggg cgacacggaa 12660
atgttgaata ctcatactct tcctttttca atattattga agcatttatc agggttattg 12720
tctcatgagc ggatacatat ttgaatgtat ttagaaaaat aaacaaatag gggttccgcg 12780
cacatttccc cgaaaagtgc cacctgacgt ctaagaaacc attattatca tgacattaac 12840
ctataaaaat aggcgtatca cgaggccctt tcgtctcgcg cgtttcggtg atgacggtga 12900
aaacctctga cacatgcagc tcccggagac ggtcacagct tgtctgtaag cggatgccgg 12960
gagcagacaa gcccgtcagg gcgcgtcagc gggtgttggc gggtgtcggg gctggcttaa 13020
ctatgcggca tcagagcaga ttgtactgag agtgcaccat atgcggtgtg aaataccgca 13080
cagatgcgta aggagaaaat accgcatcag gcgccattcg ccattcaggc tgcgcaactg 13140
ttgggaaggg cgatcggtgc gggcctcttc gctattacgc cagctggcga aagggggatg 13200
tgctgcaagg cgattaagtt gggtaacgcc agggttttcc cagtcacgac gttgtaaaac 13260
gacggccagt gcaagcttgc atgcctgcag tgcagcgtga cccggtcgtg cccctctcta 13320
gagataatga gcattgcatg tctaagttat aaaaaattac cacatatttt ttttgtcaca 13380
cttgtttgaa gtgcagttta tctatcttta tacatatatt taaactttac tctacgaata 13440
atataatcta tagtactaca ataaatatcag tgttttagag aatcatataa atgaacagtt 13500
agacatggtc taaaggacaa ttgagtattt tgacaacagg actctacagt tttatctttt 13560
tagtgtgcat gtgttctcct ttttttttgc aaatagcttc acctatataa tacttcatcc 13620
attttattag tacatccatt tagggtttag ggttaatggt tttatagac taattttttt 13680 agtacatcta ttttattcta ttttagcctc taaattaaga aaactaaaac tctattttag 13740
tttttttatt taataattta gatataaaat agaataaaat aaagtgacta aaaattaaac 13800
aaataccctt taagaaatta aaaaaactaa ggaaacattt ttcttgtttc gagtagataa 13860
tgccagcctg ttaaacgccg tcgacgagtc taacggacac caaccagcga accagcagcg 13920
tcgcgtcggg ccaagcgaag cagacggcac ggcatctctg tcgctgcctc tggacccctc 13980
tcgagagttc cgctccaccg ttggacttgc tccgctgtcg gcatccagaa attgcgtggc 14040
ggagcggcag acgtgagccg gcacggcagg cggcctcctc ctcctctcac ggcaccggca 14100
gctacggggg attcctttcc caccgctcct tcgctttccc ttcctcgccc gccgtaataa 14160
atagacaccc cctccacacc ctctttcccc aacctcgtgt tgttcggagc gcacacacac 14220
acaaccagat ctcccccaaa tccacccgtc ggcgtacgcc gctcgtcctc cccccccccc 14280
cctctctacc ttctctagat cggcgttccg gtccatggtt agggcccggt agttctactt 14340
ctgttcatgt ttgtgttaga tccgtgtttg tgttagatcc gtgctgctag cgttcgtaca 14400
cggatgcgac ctgtacgtca gacacgttct gattgctaac ttgccagtgt ttctctttgg 14460
ggaatcctgg gatggctcta gccgttccgc agacgggatc gatttcatga ttttttttgt 14520
ttcgttgcat agggtttggt ttgccctttt cctttatttc aatatatgcc gtgcacttgt 14580

-continued

```
ttgtcgggtc atcttttcat gcttttttt gtcttggttg tgatgatgtg gtctggttgg  14640
gcggtcgttc tagatcggag tagaattccc cgatctagta acatagatga caccgcgcgc  14700
gataatttat cctagtttgc gcgctatatt ttgttttcta tcgcgtatta aatgtataat  14760
tgcgggactc taatcataaa aacccatctc ataaataacg tcatgcatta catgttaatt  14820
attacatgct taacgtaatt caacagaaat tatatgataa tcatcgcaag accggcaaca  14880
ggattcaatc ttaagaaact ttattgccaa atgtttgaac gatcggggaa attcgagctc  14940
ttagaactcc caccactttt ggaactccca ccacttttga aggtctggca gttgttcttc  15000
aatctccaac aaactgtttc cttcttcaag gtacgcaaaa ccgtcgcaaa acggaacatt  15060
catttcttga ccaaacataa cgtccggaga gttcgtaaac cgatcatccg attcttcacc  15120
gctgccacta ctactagttt tctcttgatg cttttcggct acatttctca gcacctccaa  15180
ttgattgagt agggcctgat tctctttctt tagagactcg gatttagacg caagcgtctc  15240
gtagttatgc tttagcgcgt tatactcttg ctcaatctgc ctcgactttg atcgcgcgcg  15300
tttgttctgg aaccatatcg ccacttgacg aggatgaagc ccgagtttat gtgccaactg  15360
gtgtttcatc cttaactcgg gtctcgactg tgtctcaaac atgtactcta ggaaacttat  15420
ttgtttgtcg gtaaatcgtc tccgcccctc gtttcggttc ttcctggtgg ttgttacttg  15480
ttgaagagac atggatccga gtcgacctgc agaagtaaca ccaaacaaca gggtgacact  15540
cgacaaaaga aacagtacca agcaaataaa tagcgtatga aggcagggct aaaaaaatcc  15600
acatatagct gctgcatatg ccatcatcca agtatatcaa gatcaaaata attataaaac  15660
atacttgttt attataatag ataggtactc aaggttagag catatgaata gatgctgcat  15720
atgccatcat gtatatgcat cagtaaaacc cacatcaaca tgtataccta tcctagatcg  15780
atatttccat ccatcttaaa ctcgtaacta tgaacgctgt cttgacacac acatacagtt  15840
ccaaaattaa taaatacacc aggtagtttg aaacagtatt ctactccgat ctagaacgaa  15900
tgaacgaccg cccaaccaca ccacatcatc acaaccaagc gaacaaaaag catctctgta  15960
tatgcatcag taaaacccgc atcaacatgt atacctatcc tagatcgata tttccatcca  16020
tcatcttcaa ttcgtaacta tgaatatgta tggcacacac atacagatcc aaaattaata  16080
aatccaccag gtagtttgaa acagaattcg taatcatggt catagctgtt tcctgtgtga  16140
aattgttatc cgctcacaat tccacacaac atacgagccg gaagcataaa gtgtaaagcc  16200
tggggtgcct aatgagtgag ctaactcaca ttaattgcgt tgcgctcact gcccgctttc  16260
cagtcgggaa acctgtcgtg ccagctgcat taatgaatcg gccaacgcgc ggggagaggc  16320
ggtttgcgta ttgggcgctc ttccgcttcc tcgctcactg actcgctgcg ctcggtcgtt  16380
cggctgcggc gagcggtatc agctcactca aaggcggtaa tacggttatc cacagaatca  16440
ggggataacg caggaaagaa catgtgagca aaaggccagc aaaaggccag gaaccgtaaa  16500
aaggccgcgt tgctggcgtt tttccatagg ctccgccccc ctgacgagca tcacaaaaat  16560
cgacgctcaa gtcagaggtg gcgaaacccg acaggactat aaagatacca ggcgtttccc  16620
cctggaagct ccctcgtgcg ctctcctgtt ccgaccctgc cgcttaccgg atacctgtcc  16680
gcctttctcc cttcgggaag cgtggcgctt tctcatagct cacgctgtag gtatctcagt  16740
tcggtgtagg tcgttcgctc caagctgggc tgtgtgcacg aaccccccgt tcagcccgac  16800
cgctgcgcct tatccggtaa ctatcgtctt gagtccaacc cggtaagaca cgacttatcg  16860
ccactggcag cagccactgg taacaggatt agcagagcga ggtatgtagg cggtgctaca  16920
gagttcttga agtggtggcc taactacggc tacactagaa ggacagtatt tggtatctgc  16980
```

gctctgctga agccagttac cttcggaaaa agagttggta gctcttgatc cggcaaacaa 17040
accaccgctg gtagcggtgg tttttttgtt tgcaagcagc agattacgcg cagaaaaaaa 17100
ggatctcaag aagatccttt gatcttttct acggggtctg acgctcagtg gaacgaaaac 17160
ttttctacgg ggtctgacgc tcagtggaac gaaaactcac gttaagggat tttggtcatg 17220
agattatcaa aaaggatctt cacctagatc cttttaaatt aaaaatgaag ttttaaatca 17280
atctaaagta tatatgagta aacttggtct gacagtttga ggcacctatc tcagcgatct 17340
gtctatttcg ttcatccata gttgcctgac tccccgtcgt gtagataact acgatacggg 17400
agggcttacc atctggcccc agtgctgcaa tgataccgcg agacccacgc tcaccggctc 17460
cagatttatc agcaataaac cagccagccg gaagggccga gcgcagaagt ggtcctgcaa 17520
ctttatccgc ctccatccag tctattaatt gttgccggga agctagagta agtagttcgc 17580
cagttaatag tttgcgcaac gttgttgcca ttgctacagg catcgtggtg tcacgctcgt 17640
cgtttggtat ggcttcattc agctccggtt cccaacgatc aaggcgagtt acatgatccc 17700
ccatgttgtg caaaaaagcg gttagctcct tcggtcctcc gatcgttgtc agaagtaagt 17760
tggccgcagt gttatcactc atggttatgg cagcactgca taattctctt actgtcatgc 17820
catccgtaag atgcttttct gtgactggtg agtactcaac caagtcattc tgagaatagt 17880
gtatgcggcg accgagttgc tcttgcccgg cgtcaatacg ggataatacc gcgccacata 17940
gcagaacttt aaaagtgctc atcattggaa aacgttcttc ggggcgaaaa ctctcaagga 18000
tcttaccgct gttgagatcc agttcgatgt aacccactcg tgcacccaac tgatcttcag 18060
catcttttac tttcaccagc gtttctgggt gagcaaaaac aggaaggcaa aatgccgcaa 18120
aaaagggaat aagggcgaca cggaaatgtt gaatactcat actcttcctt tttcaatatt 18180
attgaagcat ttatcagggt tattgtctca tgagcggata catatttgaa tgtatttaga 18240
aaaataaatg tatttagaaa aataaacaaa taggggttcc gcgcacattt ccccgaaaag 18300
tgccacctga cgtctaagaa accattatta tcatgacatt aacctataaa aataggcgta 18360
tcacgaggcc ctttcgtctc gcgcgtttcg gtgatgacgg tgaaaacctc tgacacatgc 18420
agctcccgga gacggtcaca gcttgtctgt aagcggatgc cgggagcaga caagcccgtc 18480
agggcgcgtc agcgggtgtt ggcgggtgtc ggggctggct taactatgcg gcatcagagc 18540
agattgtact gagagtgcac catatgcggt gtgaaatacc gcacagatgc gtaaggagaa 18600
aataccgcat caggcgccat tcgccattca ggctgcgcaa ctgttgggaa gggcgatcgg 18660
tgcgggcctc ttcgctatta cgccagctgg cgaaaggggg atgtgctgca aggcgattaa 18720
gttgggtaac gccagggttt tcccagtcac gacgttgtaa aacgacggcc agtgccaagc 18780
ttgcatgcct gcagtgcagc gtgacccggt cgtgcccctc tctagagata atgagcattg 18840
catgtctaag ttataaaaaa ttaccacata ttttttttgt cacacttgtt tgaagtgcag 18900
tttatctatc tttatacata tatttaaact ttactctacg aataatataa tctatagtac 18960
tacaataata tcagtgtttt agagaatcat ataaatgaac agttagacat ggtctaaagg 19020
acaattgagt attttgacaa caggactcta cagttttatc tttttagtgt gcatgtgttc 19080
tcctttttt ttgcaaatag cttcacctat ataatacttc atccatttta ttagtacatc 19140
catttagggt ttagggttaa tggtttttat agactaattt ttttagtaca tctattttat 19200
tctattttag cctctaaatt aagaaaacta aaactctatt ttagtttttt tatttaataa 19260
tttagatata aaatagaata aaataaagtg actaaaaatt aaacaaatac cctttaagaa 19320

-continued

```
attaaaaaaa ctaaggaaac atttttcttg tttcgagtag ataatgccag cctgttaaac  19380

gccgtcgacg agtctaacgg acaccaacca gcgaaccagc agcgtcgcgt cgggccaagc  19440

gaagcagacg gcacggcatc tctgtcgctg cctctggacc cctctcgaga gttccgctcc  19500

accgttggac ttgctccctt tattttattc tattttatat ctaaattatt aaataaaaaa  19560

actaaaatag agttttagtt ttcttaattt agaggcta                          19598
```

<210> SEQ ID NO 3
<211> LENGTH: 5470
<212> TYPE: DNA
<213> ORGANISM: Artificial Sequence
<220> FEATURE:
<223> OTHER INFORMATION: pIND4+HB4

<400> SEQUENCE: 3

```
aagcttgcat gcctgcagtg cagcgtgacc cggtcgtgcc cctctctaga gataatgagc     60

attgcatgtc taagttataa aaaattacca catatttttt ttgtcacact tgtttgaagt    120

gcagtttatc tatctttata catatattta aactttactc tacgaataat ataatctata    180

gtactacaat aatatcagtg ttttagagaa tcatataaat gaacagttag acatggtcta    240

aaggacaatt gagtattttg acaacaggac tctacagttt tatcttttta gtgtgcatgt    300

gttctccttt ttttttgcaa atagcttcac ctatataata cttcatccat tttattagta    360

catccattta gggtttaggg ttaatggttt ttatagacta atttttttag tacatctatt    420

ttattctatt ttagcctcta aattaagaaa actaaaactc tattttagtt tttttattta    480

ataatttaga tataaaatag aataaaataa agtgactaaa aattaaacaa ataccettta    540

agaaattaaa aaaactaagg aaacattttt cttgtttcga gtagataatg ccagcctgtt    600

aaacgccgtc gacgagtcta acggacacca accagcgaac cagcagcgtc gcgtcgggcc    660

aagcgaagca gacggcacgg catctctgtc gctgcctctg gacccctctc gagagttccg    720

ctccaccgtt ggacttgctc cgctgtcggc atccagaaat tgcgtggcgg agcggcagac    780

gtgagccggc acggcaggcg gcctcctcct cctctcacgg caccggcagc tacgggggat    840

tcctttccca ccgctccttc gctttccctt cctcgcccgc cgtaataaat agacaccccc    900

tccacaccct ctttccccaa cctcgtgttg ttcggagcgc acacacacac aaccagatct    960

cccccaaatc cacccgtcgg cacctccgct tcaaggtacg ccgctcgtcc tccccccccc   1020

cccctctcta ccttctctag atcggcgttc cggtccatgg ttagggcccg gtagttctac   1080

ttctgttcat gtttgtgtta gatccgtgtt tgtgttagat ccgtgctgct agcgttcgta   1140

cacggatgcg acctgtacgt cagacacgtt ctgattgcta acttgccagt gtttctcttt   1200

ggggaatcct gggatggctc tagccgttcc gcagacggga tcgatttcat gatttttttt   1260

gtttcgttgc atagggtttg gtttgccctt ttcctttatt tcaatatatg ccgtgcactt   1320

gtttgtcggg tcatcttttc atgctttttt ttgtcttggt tgtgatgatg tggtctggtt   1380

gggcggtcgt tctagatcgg agtagaattc tgtttcaaac tacctggtgg atttattaat   1440

tttggatctg tatgtgtgtg ccatacatat tcatagttac gaattgaaga tgatggatgg   1500

aaatatcgat ctaggatagg tatacatgtt gatgcgggtt ttactgatgc atatacagag   1560

atgctttttg ttcgcttggt tgtgatgatg tggtgtggtt gggcggtcgt tcattcgttc   1620

tagatcggag tagaatactg tttcaaacta cctggtgtat ttattaattt tggaactgta   1680

tgtgtgtgtc atacatcttc atagttacga gtttaagatg gatggaaata tcgatctagg   1740

ataggtatac atgttgatgt gggttttact gatgcatata catgatggca tatgcagcat   1800
```

-continued

```
ctattcatat gctctaacct tgagtaccta tctattataa taaacaagta tgttttataa   1860
ttattttgat cttgatatac ttggatgatg gcatatgcag cagctatatg tggatttttt   1920
tagccctgcc ttcatacgct atttatttgc ttggtactgt ttcttttgtc gatgctcacc   1980
ctgttgtttg gtgttacttc tgcaggtcga ctctagagga tccgatccac catgtctctt   2040
caacaagtaa caaccaccag gaagaaccga aacgaggggc ggagacgatt taccgacaaa   2100
caaataagtt tcctagagta catgtttgag acacagtcga gacccgagtt aaggatgaaa   2160
caccagttgg cacataaact cgggcttcat cctcgtcaag tggcgatatg gttccagaac   2220
aaacgcgcgc gatcaaagtc gaggcagatt gagcaagagt ataacgcgct aaagcataac   2280
tacgagacgc ttgcgtctaa atccgagtct ctaaagaaag agaatcaggc cctactcaat   2340
caattggagg tgctgagaaa tgtagccgaa aagcatcaag agaaaactag tagtagtggc   2400
agcggtgaag aatcggatga tcggtttacg aactctccgg acgttatgtt tggtcaagaa   2460
atgaatgttc cgttttgcga cggttttgcg taccttgaag aaggaaacag tttgttggag   2520
attgaagaac aactgccaga ccttcaaaag tggtgggagt tctaagagct cgaatttccc   2580
cgatcgttca aacatttggc aataaagttt cttaagattg aatcctgttg ccggtcttgc   2640
gatgattatc atataatttc tgttgaatta cgttaagcat gtaataatta acatgtaatg   2700
catgacgtta tttatgagat gggtttttat gattagagtc ccgcaattat acatttaata   2760
cgcgatagaa aacaaaatat agcgcgcaaa ctaggataaa ttatcgcgcg cggtgtcatc   2820
tatgttacta gatcggaatt cgtaatcatg gtcatagctg tttcctgtgt gaaattgtta   2880
tccgctcaca attccacaca acatacgagc cggaagcata aagtgtaaag cctggggtgc   2940
ctaatgagtg agctaactca cattaattgc gttgcgctca ctgcccgctt tccagtcggg   3000
aaacctgtcg tgccagctgc attaatgaat cggccaacgc gcggggagag gcggtttgcg   3060
tattgggcgc tcttccgctt cctcgctcac tgactcgctg cgctcggtcg ttcggctgcg   3120
gcgagcggta tcagctcact caaaggcggt aatacggtta tccacagaat caggggataa   3180
cgcaggaaag aacatgtgag caaaaggcca gcaaaaggcc aggaaccgta aaaaggccgc   3240
gttgctggcg tttttccata ggctccgccc ccctgacgag catcacaaaa atcgacgctc   3300
aagtcagagg tggcgaaacc cgacaggact ataaagatac caggcgtttc cccctggaag   3360
ctccctcgtg cgctctcctg ttccgaccct gccgcttacc ggatacctgt ccgcctttct   3420
cccttcggga agcgtggcgc tttctcatag ctcacgctgt aggtatctca gttcggtgta   3480
ggtcgttcgc tccaagctgg gctgtgtgca cgaacccccc gttcagcccg accgctgcgc   3540
cttatccggt aactatcgtc ttgagtccaa cccggtaaga cacgacttat cgccactggc   3600
agcagccact ggtaacagga ttagcagagc gaggtatgta ggcggtgcta cagagttctt   3660
gaagtggtgg cctaactacg gctacactag aaggacagta tttggtatct gcgctctgct   3720
gaagccagtt accttcggaa aaagagttgg tagctcttga tccggcaaac aaaccaccgc   3780
tggtagcggt ggtttttttg tttgcaagca gcagattacg cgcagaaaaa aaggatctca   3840
agaagatcct ttgatctttt ctacggggtc tgacgctcag tggaacgaaa actcacgtta   3900
agggattttg gtcatgagat tatcaaaaag gatcttcacc tagatccttt taaattaaaa   3960
atgaagtttt aaatcaatct aaagtatata tgagtaaact tggtctgaca gttaccaatg   4020
cttaatcagt gaggcaccta tctcagcgat ctgtctattt cgttcatcca tagttgcctg   4080
actccccgtc gtgtagataa ctacgatacg ggagggctta ccatctggcc ccagtgctgc   4140
```

aatgataccg cgagacccac gctcaccggc tccagattta tcagcaataa accagccagc 4200
cggaagggcc gagcgcagaa gtggtcctgc aactttatcc gcctccatcc agtctattaa 4260
ttgttgccgg gaagctagag taagtagttc gccagttaat agtttgcgca acgttgttgc 4320
cattgctaca ggcatcgtgg tgtcacgctc gtcgtttggt atggcttcat tcagctccgg 4380
ttcccaacga tcaaggcgag ttacatgatc ccccatgttg tgcaaaaaag cggttagctc 4440
cttcggtcct ccgatcgttg tcagaagtaa gttggccgca gtgttatcac tcatggttat 4500
ggcagcactg cataattctc ttactgtcat gccatccgta agatgctttt ctgtgactgg 4560
tgagtactca accaagtcat tctgagaata gtgtatgcgg cgaccgagtt gctcttgccc 4620
ggcgtcaata cgggataata ccgcgccaca tagcagaact ttaaaagtgc tcatcattgg 4680
aaaacgttct tcggggcgaa aactctcaag gatcttaccg ctgttgagat ccagttcgat 4740
gtaacccact cgtgcaccca actgatcttc agcatctttt actttcacca gcgtttctgg 4800
gtgagcaaaa acaggaaggc aaaatgccgc aaaaaaggga ataagggcga cacggaaatg 4860
ttgaatactc atactcttcc tttttcaata ttattgaagc atttatcagg gttattgtct 4920
catgagcgga tacatatttg aatgtattta gaaaaataaa caaatagggg ttccgcgcac 4980
atttccccga aaagtgccac ctgacgtcta agaaaccatt attatcatga cattaaccta 5040
taaaaatagg cgtatcacga ggccctttcg tctcgcgcgt ttcggtgatg acggtgaaaa 5100
cctctgacac atgcagctcc cggagacggt cacagcttgt ctgtaagcgg atgccgggag 5160
cagacaagcc cgtcagggcg cgtcagcggg tgttggcggg tgtcggggct ggcttaacta 5220
tgcggcatca gagcagattg tactgagagt gcaccatatg cggtgtgaaa taccgcacag 5280
atgcgtaagg agaaaatacc gcatcaggcg ccattcgcca ttcaggctgc gcaactgttg 5340
ggaagggcga tcggtgcggg cctcttcgct attacgccag ctggcgaaag ggggatgtgc 5400
tgcaaggcga ttaagttggg taacgccagg gttttcccag tcacgacgtt gtaaaacgac 5460
ggccagtgcc 5470

<210> SEQ ID NO 4
<211> LENGTH: 5496
<212> TYPE: DNA
<213> ORGANISM: Artificial Sequence
<220> FEATURE:
<223> OTHER INFORMATION: pIND4+BAR

<400> SEQUENCE: 4
aagcttgcat gcctgcagtg cagcgtgacc cggtcgtgcc cctctctaga gataatgagc 60
attgcatgtc taagttataa aaaattacca catatttttt ttgtcacact tgtttgaagt 120
gcagtttatc tatctttata catatattta aactttactc tacgaataat ataatctata 180
gtactacaat aatatcagtg ttttagagaa tcatataaat gaacagttag acatggtcta 240
aaggacaatt gagtattttg acaacaggac tctacagttt tatcttttta gtgtgcatgt 300
gttctccttt ttttttgcaa atagcttcac ctatataata cttcatccat tttattagta 360
catccattta gggtttaggg ttaatggttt ttatagacta atttttttag tacatctatt 420
ttattctatt ttagcctcta aattaagaaa actaaaactc tattttagtt tttttattta 480
ataatttaga tataaaatag aataaaataa agtgactaaa aattaaacaa ataccccttta 540 agaaattaaa aaaactaagg aaacattttt cttgtttcga gtagataatg ccagcctgtt 600
aaacgccgtc gacgagtcta acggacacca accagcgaac cagcagcgtc gcgtcgggcc 660
aagcgaagca gacggcacgg catctctgtc gctgcctctg gacccctctc gagagttccg 720

-continued

```
ctccaccgtt ggacttgctc cgctgtcggc atccagaaat tgcgtggcgg agcggcagac    780
gtgagccggc acggcaggcg gcctcctcct cctctcacgg caccggcagc tacgggggat    840
tcctttccca ccgctccttc gctttccctt cctcgcccgc cgtaataaat agacaccccc    900
tccacaccct ctttccccaa cctcgtgttg ttcggagcgc acacacacac aaccagatct    960
cccccaaatc cacccgtcgg cacctccgct tcaaggtacg ccgctcgtcc tccccccccc   1020
cccctctcta ccttctctag atcggcgttc cggtccatgg ttagggcccg gtagttctac   1080
ttctgttcat gtttgtgtta gatccgtgtt tgtgttagat ccgtgctgct agcgttcgta   1140
cacggatgcg acctgtacgt cagacacgtt ctgattgcta acttgccagt gtttctcttt   1200
ggggaatcct gggatggctc tagccgttcc gcagacggga tcgatttcat gatttttttt   1260
gtttcgttgc atagggtttg gtttgccctt ttcctttatt tcaatatatg ccgtgcactt   1320
gtttgtcggg tcatcttttc atgctttttt ttgtcttggt tgtgatgatg tggtctggtt   1380
gggcggtcgt tctagatcgg agtagaattc tgtttcaaac tacctggtgg atttattaat   1440
tttggatctg tatgtgtgtg ccatacatat tcatagttac gaattgaaga tgatggatgg   1500
aaatatcgat ctaggatagg tatacatgtt gatgcgggtt ttactgatgc atatacagag   1560
atgctttttg ttcgcttggt tgtgatgatg tggtgtggtt gggcggtcgt tcattcgttc   1620
tagatcggag tagaatactg tttcaaacta cctggtgtat ttattaattt tggaactgta   1680
tgtgtgtgtc atacatcttc atagttacga gtttaagatg gatggaaata tcgatctagg   1740
ataggtatac atgttgatgt gggttttact gatgcatata catgatggca tatgcagcat   1800
ctattcatat gctctaacct tgagtaccta tctattataa taaacaagta tgttttataa   1860
ttattttgat cttgatatac ttggatgatg gcatatgcag cagctatatg tggatttttt   1920
tagccctgcc ttcatacgct atttatttgc ttggtactgt ttcttttgtc gatgctcacc   1980
ctgttgtttg gtgttacttc tgcaggtcga ctctagagga tccatcgatt aggaagtaac   2040
catgagccca gaacgacgcc cggccgacat ccgccgtgcc accgaggcgg acatgccggc   2100
ggtctgcacc atcgtcaacc actacatcga gacaagcacg gtcaacttcc gtaccgagcc   2160
gcaggaaccg caggagtgga cggacgacct cgtccgtctg cgggagcgct atccctggct   2220
cgtcgccgag gtggacggcg aggtcgccgg catcgcctac gcgggcccct ggaaggcacg   2280
caacgcctac gactggacgg ccgagtcgac cgtgtacgtc tccccccgcc accagcggac   2340
gggactgggc tccacgctct acacccacct gctgaagtcc ctggaggcac agggcttcaa   2400
gagcgtggtc gctgtcatcg ggctgcccaa cgacccgagc gtgcgcatgc acgaggcgct   2460
cggatatgcc ccccgcggca tgctgcgggc ggccggcttc aagcacggga actggcatga   2520
cgtgggtttc tggcagctgg acttcagcct gccggtaccg ccccgtccgg tcctgcccgt   2580
caccgagatc tgatccgtcg acctgcagat cgttcaaaca tttggcaata aagtttctta   2640
agattgaatc ctgttgccgg tcttgcgatg attatcatat aatttctgtt gaattacgtt   2700
aagcatgtaa taattaacat gtaatgcatg acgttattta tgagatgggt ttttatgatt   2760
agagtcccgc aattatacat ttaatacgcg atagaaaaca aaatatagcg cgcaaactag   2820
gataaattat cgcgcgcggt gtcatctatg ttactagatc ggaattcgta atcatggtca   2880
tagctgtttc ctgtgtgaaa ttgttatccg ctcacaattc cacacaacat acgagccgga   2940
agcataaagt gtaaagcctg gggtgcctaa tgagtgagct aactcacatt aattgcgttg   3000
cgctcactgc ccgctttcca gtcgggaaac ctgtcgtgcc agctgcatta atgaatcggc   3060
```

-continued

```
caacgcgcgg ggagaggcgg tttgcgtatt gggcgctctt ccgcttcctc gctcactgac   3120

tcgctgcgct cggtcgttcg gctgcggcga gcggtatcag ctcactcaaa ggcggtaata   3180

cggttatcca cagaatcagg ggataacgca ggaaagaaca tgtgagcaaa aggccagcaa   3240

aaggccagga accgtaaaaa ggccgcgttg ctggcgtttt tccataggct ccgcccccct   3300

gacgagcatc acaaaaatcg acgctcaagt cagaggtggc gaaacccgac aggactataa   3360

agataccagg cgtttccccc tggaagctcc ctcgtgcgct ctcctgttcc gaccctgccg   3420

cttaccggat acctgtccgc ctttctccct tcgggaagcg tggcgctttc tcatagctca   3480

cgctgtaggt atctcagttc ggtgtaggtc gttcgctcca agctgggctg tgtgcacgaa   3540

ccccccgttc agcccgaccg ctgcgcctta tccggtaact atcgtcttga gtccaacccg   3600

gtaagacacg acttatcgcc actggcagca gccactggta acaggattag cagagcgagg   3660

tatgtaggcg gtgctacaga gttcttgaag tggtggccta actacggcta cactagaagg   3720

acagtatttg gtatctgcgc tctgctgaag ccagttacct tcggaaaaag agttggtagc   3780

tcttgatccg gcaaacaaac caccgctggt agcggtggtt tttttgtttg caagcagcag   3840

attacgcgca gaaaaaaagg atctcaagaa gatcctttga tcttttctac ggggtctgac   3900

gctcagtgga acgaaaactc acgttaaggg attttggtca tgagattatc aaaaaggatc   3960

ttcacctaga tccttttaaa ttaaaaatga agttttaaat caatctaaag tatatatgag   4020

taaacttggt ctgacagtta ccaatgctta atcagtgagg cacctatctc agcgatctgt   4080

ctatttcgtt catccatagt tgcctgactc cccgtcgtgt agataactac gatacgggag   4140

ggcttaccat ctggccccag tgctgcaatg ataccgcgag acccacgctc accggctcca   4200

gatttatcag caataaacca gccagccgga agggccgagc gcagaagtgg tcctgcaact   4260

ttatccgcct ccatccagtc tattaattgt tgccgggaag ctagagtaag tagttcgcca   4320

gttaatagtt tgcgcaacgt tgttgccatt gctacaggca tcgtggtgtc acgctcgtcg   4380

tttggtatgg cttcattcag ctccggttcc caacgatcaa ggcgagttac atgatccccc   4440

atgttgtgca aaaaagcggt tagctccttc ggtcctccga tcgttgtcag aagtaagttg   4500

gccgcagtgt tatcactcat ggttatggca gcactgcata attctcttac tgtcatgcca   4560

tccgtaagat gcttttctgt gactggtgag tactcaacca agtcattctg agaatagtgt   4620

atgcggcgac cgagttgctc ttgcccggcg tcaatacggg ataataccgc gccacatagc   4680

agaactttaa aagtgctcat cattggaaaa cgttcttcgg ggcgaaaact ctcaaggatc   4740

ttaccgctgt tgagatccag ttcgatgtaa cccactcgtg cacccaactg atcttcagca   4800

tcttttactt tcaccagcgt ttctgggtga gcaaaaacag gaaggcaaaa tgccgcaaaa   4860

aagggaataa gggcgacacg gaaatgttga atactcatac tcttcctttt tcaatattat   4920

tgaagcattt atcagggtta ttgtctcatg agcggataca tatttgaatg tatttagaaa   4980

aataaacaaa taggggttcc gcgcacattt ccccgaaaag tgccacctga cgtctaagaa   5040

accattatta tcatgacatt aacctataaa aataggcgta tcacgaggcc ctttcgtctc   5100

gcgcgtttcg gtgatgacgg tgaaaacctc tgacacatgc agctcccgga gacggtcaca   5160

gcttgtctgt aagcggatgc cgggagcaga caagcccgtc agggcgcgtc agcgggtgtt   5220

ggcgggtgtc ggggctggct taactatgcg gcatcagagc agattgtact gagagtgcac   5280

catatgcggt gtgaaatacc gcacagatgc gtaaggagaa aataccgcat caggcgccat   5340

tcgccattca ggctgcgcaa ctgttgggaa gggcgatcgg tgcgggcctc ttcgctatta   5400

cgccagctgg cgaaaggggg atgtgctgca aggcgattaa gttgggtaac gccagggttt   5460
```

tcccagtcac gacgttgtaa aacgacggcc agtgcc 5496

<210> SEQ ID NO 5
<211> LENGTH: 47611
<212> TYPE: DNA
<213> ORGANISM: Artificial Sequence
<220> FEATURE:
<223> OTHER INFORMATION: Long insert with flanking regions

<400> SEQUENCE: 5
taatggtgag tgtatgcgct tgcgtctgta ttgtgtttaa aaaactcatt ctaagaaact 60
cgtcatacag tgtccaccgt caaggagcca tctagtaggg tgtggatggg catgtgacag 120
gaaccttgtc gtgtgcacgt tgtatgtcgg tcttgttcaa tatgtcgtct gtttcctcgg 180
cttacatgct cttttacgtg tcgtgcaccc aactgatctt cagcatcttt tactttcacc 240
agcgtttctg ggtgagcaaa aacaggaagg caaaatgccg caaaaaaggg aataagggcg 300
acacggaaat gttgaatact catactcttc ctttttcaat attattgaag catttatcag 360
ggttattgtc tcatgagcgg atacatattt gaatgtattt agaaaaataa acaaataggg 420
gttccgcgca catttccccg aaaagtgcca cctgacgtct aagaaaccat tattatcatg 480
acattaacct ataaaaatag gcgtatcacg aggccctttc gtctcgcgcg tttcggtgat 540
gacggtgaaa acctctgaca catgcagctc ccggagacgg tcacagcttg tctgtaagcg 600
gatgccggga gcagacaagc ccgtcagggc gcgtcagcgg gtgttggcgg gtgtcggggc 660
tggcttaact atgcggcatc agagcagatt gtactgagag tgcaccatat gcggtgtgaa 720
ataccgcaca gatgcgtaag gagaaaatac cgcatcaggc gccattcgcc attcaggctg 780
cgcaactgtt gggaagggcg atcggtgcgg gcctcttcgc tattacgcca gctggcgaaa 840
gggggatgtg ctgcaaggcg attaagttgg gtaacgccag ggttttccca gtcacgacgt 900
tgtaaaacga cggccagtgc caagcttgca tgcctgcagt gcagcgtgac ccggtcgtgc 960
ccctctctag agataatgag cattgcatgt ctaagttata aaaaattacc acatattttt 1020
tttgtcacac ttgtttgaag tgcagtttat ctatctttat acatatattt aaactttact 1080
ctacgaataa tataatctat agtactacaa taatatcagt gttttagaga atcatataaa 1140
tgaacagtta gacatggtct aaaggacaat tgagtatttt gacaacagga ctctacagtt 1200
ttatcttttt agtgtgcatg tgttctcctt tttttttgca aatagcttca cctatataat 1260
acttcatcca ttttattagt acatccattt agggtttagg gttaatggtt tttatagact 1320 aatttttttta gtacatctat tttattctat tttagcctct aaattaagaa aactaaaact 1380
ctattttagt ttttttattt aataatttag atataaaata gaataaaata aagtgactaa 1440
aaattaaaca aataccottt aagaaattaa aaaaactaag gaaacatttt tcttgtttcg 1500
agtagataat gccagcctgt taaacgccgt cgacgagtct aacggacacc aaccagcgaa 1560
ccagcagcgt cgcgtcgggc caagcgaagc agacggcacg gcatctctgt cgctgcctct 1620
ggacccctct cgagagttcc gctccaccgt tggacttgct ccgctgtcgg catccagaaa 1680
ttgcgtggcg gagcggcaga cgtgagccgg cacggcaggc ggcctcctcc tcctctcacg 1740
gcaccggcag ctacggggga ttcctttccc accgctcctt cgctttccct tcctcgcccg 1800
ccgtaataaa tagacacccc ctccacaccc tctttcccca acctcgtgtt gttcggagcg 1860
cacacacaca caaccagatc tccccccaaat ccacccgtcg gcgtacgccg ctcgtcctcc 1920
cccccccccc ctctctacct tctctagatc ggcgttccgg tccatggtta gggcccggta 1980

-continued

```
gttctacttc tgttcatgtt tgtgttagat ccgtgtttgt gttagatccg tgctgctagc   2040
gttcgtacac ggatgcgacc tgtacgtcag acacgtaacg tccggagagt tcgtaaaccg   2100
atcatccgat tcttcaccgc tgccactact actagttttc tcttgatgct tttcggctac   2160
atttctcagc acctccaatt gattgagtag ggcctgattc tctttcttta gagactcgga   2220
tttagacgca agcgtctcgt agttatgctt tagcgcgtta tactcttgct caatctgcct   2280
cgactttgat cgcgcgcgtt tgttctggaa ccatatcgcc acttgacgag gatgaagccc   2340
gagtttatgt gccaactggt gtttcatcct taactcgggt ctcgactgtg tctcaaacat   2400
gtactctagg aaacttattt gtttgtcggt aaatcgtctc cgcccctcgt ttcggttctt   2460
cctggtggtt gttacttgtt gaagagacat ggatccgggt gtgatcctct atagtcgacc   2520
tgcagaagta acaccaaaca acagggtgag catcgacaaa agaaacagta ccaagcaaat   2580
aaatagcgta tgaaggcagg gctaaaaaaa tccacatata gctgctgcat atgccatcat   2640
ccaagtatat caagatcaaa ataattataa aacatacttg tttattataa tagataggta   2700
ctcaaggtta gagcatatga atagatgctg catatgccat catgtatatg catcagtaaa   2760
acccacatca acatgtatac ctatcctaga tcgatatttc catccatctt aaactcgtaa   2820
ctatgaagat gtatgacaca cacatacagt tccaaaatta ataaatacac caggtagttt   2880
gaaacagtat tctactccga tctagaacga atgaacgacc gcccaaccac accacatcat   2940
cacaaccaag cgaacaaaaa gcatctctgt atatgcatca gtaaaacccg catcaacatg   3000
tatacctatc ctagatcgat atttccatcc atcatcttca attcgtaact atgaatatgt   3060
atggcacaca catacagatc caaaattaat aaatccacca ggtagtttga aacagaattg   3120
gaattcgtaa tcatggtcat agctgtttcc tgtgtgaaat tgttatccgc tcacaattcc   3180
acacaacata cgagccggaa gcataaagtg taaagcctgg ggtgcctaat gagtgagcta   3240
actcacatta attgcgttgc gctcactgcc cgctttccag tcgggaaacc tgtcgtgcca   3300
gctgcattaa tgaatcggcc aacgcgcggg gagaggcggt ttgcgtattg ggcgctcttc   3360
cgcttcctcg ctcactgact cgctgcgctc ggtcgttcgg ctgcggcgag cggtatcagc   3420
tcactcaaag gcggtaatac ggttatccac agaatcaggg gataacgcag gaaagaacat   3480
gtgagcaaaa ggccagcaaa aggccaggaa ccgtaaaaag gccgcgttgc tggcgttttt   3540
ccataggctc cgcccccctg acgagcatca caaaaatcga cgctcaagtc agaggtggcg   3600
aaacccgaca ggactataaa gataccaggc gtttccccct ggaagctccc tcgtgcgctc   3660
tcctgttccg accctgccgc ttaccggata cctgtccgcc tttctccctt cgggaagcgt   3720
ggcgctttct catagctcac gctgtaggta tctcagttcg gtgtaggtcg ttcgctccaa   3780
gctgggctgt gtgcacgaac cccccgttca gcccgaccgc tgcgccttat ccggtaacta   3840
tcgtcttgag tccaacccgg taagacacga cttatcgcca ctggcagcag ccactggtaa   3900
caggattagc agagcgaggt atgtaggcgg tgctacagag ttcttgaagt ggtggcctaa   3960
ctacggctac actagaagga cagtatttgg tatctgcgct ctgctgaagc cagttacctt   4020
cggaaaaaga gttggtagct cttgatccgg caaacaaacc accgctggta gcggtggttt   4080
ttttgtttgc aagcagcaga ttacgcgcag aaaaaaagga tctcaagaag atcctttgat   4140
cttttctacg gggtctgacg ctcagtggaa cgaaaactca cgttaaggga ttttggtcat   4200
gagattatca aaaaggatct tcacctagat ccttttaaat taaaaatgaa gttttaaatc   4260
aatctaaagt atatatgagt aaacttggtc tgacagtttt caaatatgta tccgctcatg   4320
agacaataac cctgataaat gcttcaataa tattgaaaaa ggaagagtat gagtattcaa   4380
```

-continued

```
catttccgtg tcgcccttat tccctttttt gcggcatttt gccttcctgt ttttgctcac   4440
ccagaaacgc tggtgaaagt aaaagatgct gaagatcagt tgggtgcacg agtgggttac   4500
atcgaactgg atctcaacag cggtaagatc cttgagagtt ttcgccccga agaacgtttt   4560
ccaatgatga gcacttttaa agttctgcta tgtggcgcgg tattatcccg tattgacgcc   4620
gggcaagagc aactcggtcg ccgcatacac tattctcaga atgacttggt tgagtactca   4680
ccagtcacag aaaagcatct tacggatggc atgacagtaa gagaattatg cagtgctgcc   4740
ataaccatga gtgataacac tgcggccaac ttacttctga caacgatcgg aggaccgaag   4800
gagctaaccg cttttttgca caacatgggg gatcatgtaa ctcgccttga tcgttgggaa   4860
ccggagctga atgaagccat accaaacgac gagcgtgaca ccacgatgcc tgtagcaatg   4920
gcaacaacgt tgcgcaaact attaactggc gaactactta ctctagcttc ccggcaacaa   4980
ttaatagact ggatggaggc ggataaagtt gcaggaccac ttctgcgctc ggcccttccg   5040
gctggctggt ttattgctga taaatctgga gccggtgagc gtgggtctcg cggtatcatt   5100
gcagcactgg ggccagatgg taagccctcc cgtatcgtag ttatctacac gacggggagt   5160
caggcaacta tggatgaacg aaatagacag atcgctgaga taggtgcctc actgattaag   5220
cattggtaaa actgtcagac caagtttact catatatact ttagattgat ttaaaacttc   5280
atttttaatt taaaaggatc taggtgaaga tcctttttga taatctcatg accaaaatcc   5340
cttaacgtga gttttcgttc cactgagcgt cagaccccgt agaaaagatcg ttcaaacatt   5400
tggcaataaa gtttcttaag attgaatcct gttgccggtc ttgcgatgat tatcatataa   5460
tttctgttga attacgttaa gcatgtaata attaacatgt aatgcatgac gttatttatg   5520
agatgggttt ttatgattag agtcccgcaa ttatacattt aatacgcgat agaaaacaaa   5580
atatagcgcg caaactagga taaattatcg cgcgcggtgt catctatgtt actagatcgg   5640
atccatgagc ccagaacgac gcccggccga catccgccgt gccaccgagg cggacatgcc   5700
ggcggtctgc accatcgtca accactacat cgagacaagc acggtcaact tccgtaccga   5760
gccgcaggaa ccgcaggagt ggacggacga cctcgtccgt ctgcgggagc gctatccctg   5820
gctcgtcgcc gaggtggacg gcgaggtcgc cggcatcgcc tacgcgggcc cctggaaggc   5880
acgcaacgcc tacgactgga cggccgagtc gaccgtgtac gtctcccccc gccaccagcg   5940
gacgggactg ggctccacgc tctacaccca cctgctgaag tccctggagg cacagggctt   6000
caagagcgtg gtcgctgtca tcgggctgcc caacgacccg agcgtgcgca tgcacgaggc   6060
gctcggatat gccccccgcg gcatgctgcg ggcggccggc ttcaagcacg ggaactggca   6120
tgacgtgggt ttctggcagc tggacttcag cctgccggta ccgccccgtc cggtcctgcc   6180
cgtcaccgag atcgatcgtt caaacatttg gcaataaagt ttcttaagat tgaatcctgt   6240
tgccggtctt gcgatgatta tcatataatt tctgttgaat tacgttaagc atgtaataat   6300
taacatgtaa tgcatgacgt tatttatgag atgggttttt atgattagag tcccgcaatt   6360
atacatttaa tacgcgatag aaaacaaaat atagcgcgca aactaggata aattatcgcg   6420
cgcggtgtca tctatgttac tagatcggaa ttcgtaatca tggtcatagc tgtttcctgt   6480
gtgaaattgt tatccgctca caattccaca caacatacga gccggaagca taaagtgtaa   6540
agcctggggt gcctaatgag tgagctaact cacattaatt gcgttgcgct cactgcccgc   6600
tttccagtcg ggaaacctgt cgtgccagct gcattaatga atcggccaac gcgcggggag   6660
aggcggtttg cgtattgggc gctcttccgc ttcctcgctc actgactcgc tgcgctcggt   6720
```

-continued

```
cgttcggctg cggcgagcgg tatcagctca ctcaaaggcg gtaatacggt tatccacaga   6780
atcaggggat aacgcaggaa agaacatgtg agcaaaaggc cagcaaaagg ccaggaaccg   6840
taaaaaggcc gcgttgctgg cgtttttcca taggctccgc ccccctgacg agcatcacaa   6900
aaatcgacgc tcaagtcaga ggtggcgaaa cccgacagga ctataaagat accaggcgtt   6960
tccccctgga agctccctcg tgcgctctcc tgttccgacc ctgccgctta ccggatacct   7020
gtccgccttt ctcccttcgg gaagcgtggc gctttctcat agctcacgct gtaggtatct   7080
cagttcggtg taggtcgttc gctccaagct gggctgtgtg cacgaacccc ccgttcagcc   7140
cgaccgctgc gccttatccg gtaactatcg tcttgagtcc aacccggtaa gacacgactt   7200
atcgccactg gcagcagcca ctggtaacag gattagcaga gcgaggtatg taggcggtgc   7260
tacagagttc ttgaagtggt ggcctaacta cggctacact agaaggacag tatttggtat   7320
ctgcgctctg ctgaagccag ttaccttcgg aaaaagagtt ggtagctctt gatccggcaa   7380
acaaaccacc gctggtagcg gtggtttttt tgtttgcaag cagcagatta cgcgcagaaa   7440
aaaaggatct caagaagatc ctttgatctt ttctacgggg tctgacgctc agtggaacga   7500
aaactcacgt taagggattt tggtcatgag attatcaaaa aggatcttca cctagatcct   7560
tttaaattaa aaatgaagtt ttaaatcaat ctaaagtata tatgagtaaa cttggtctga   7620
cagttaccaa tgcttaatca gtgaggcacc tatctcagcg atctgtctat ttcgttcatc   7680
catagttgcc tgactccccg tcgtgtagat aactacgata cgggagggct taccatctgg   7740
ccccagtgct gcaatgatac cgcgagaccc acgctcaccg gctccagatt tatcagcaat   7800
aaaccagcca gccggaaggg ccgagcgcag aagtggtcct gcaactttat ccgcctccat   7860
ccagtctatt aattgttgcc gggaagctag agtaagtagt tcgccagtta atagtttgcg   7920
caacgttgtt gccattgcta caggcatcgt ggtgtcacgc tcgtcgtttg gtatggcttc   7980
attcagctcc ggttcccaac gatcaaggcg agttacatga tcccccatgt tgtgcaaaaa   8040
agcggttagc tccttcggtc ctccgatcgt tgtcagaagt aagttggccg cagtgttatc   8100
actcatggtt atggcagcac tgcataattc tcttactgtc atgccatccg taagatgctt   8160
ttctgtgact ggtgagtact caaccaagtc attctgagaa tagtgtatgc ggcgaccgag   8220
ttgctcttgc ccggcgtcaa tacgggataa taccgcgcca catagcagaa ctttaaaagt   8280
gctcatcatt ggaaaacgtt cttcggggcg aaaactctca aggatcttac cgctgttgag   8340
atccagttcg atgtaaccca ctcgtgcacc caactgatct tcagcatctt ttactttcac   8400
cagcgtttct gggtgagcaa aaacaggaag gcaaaatgcc gcaaaaaagg gaataagggc   8460
gacacggaaa tgttgaatac tcatactctt cctttttcaa tattattgaa gcatttatca   8520
gggttattgt ctcatgagcg gatacatatt tgaatgtatt tagaaaaata aacaaatagg   8580
ggttccgcgc acatttcccc gaaaagtgcc acctgacgtc taagaaacca ttattatcat   8640
gacattaacc tataaaaata ggcgtatcac gaggcccttt cgtctcgcgc gtttcggtga   8700
tgacggtgaa aacctctgac acatgcagct cccggagacg gtcacagctt gtctgtaagc   8760
ggatgccggg agcagacaag cccgtcaggg cgcgtcagcg ggtgttggcg ggtgtcgggg   8820
ctggcttaac tatgcggcat cagagcagat tgtactgaga gtgcaccata tgcggtgtga   8880
aataccgcac agatgcgtaa ggagaaaata ccgcatcagg cgccattcgc cattcaggct   8940
gcgcaactgt tgggaagggc gatcggtgcg ggcctcttcg ctattacgcc agctggcgaa   9000
agggggatgt gctgcaaggc gattaagttg ggtaacgcca gggttttccc agtcacgacg   9060
ttgtaaaacg acggccagtg caagcttgca tgcctgcagt gcagcgtgac ccggtcgtgc   9120
```

-continued

```
ccctctctag agataatgag cattgcatgt ctaagttata aaaaattacc acatattttt   9180
tttgtcacac ttgtttgaag tgcagtttat ctatctttat acatatattt aaactttact   9240
ctacgaataa tataatctat agtactacaa taatatcagt gttttagaga atcatataaa   9300
tgaacagtta gacatggtct aaaggacaat tgagtatttt gacaacagga ctctacagtt   9360
ttatcttttt agtgtgcatg tgttctcctt ttttttgca aatagcttca cctatataat   9420
acttcatcca ttttattagt acatccattt agggtttagg gttaatggtt tttatagact   9480
aatttttta gtacatctat tttattctat tttagcctct aaattaagaa aactaaaact   9540
ctattttagt ttttttattt aataatttag atataaaata gaataaaata aagtgactaa   9600
aaattaaaca aatacccttt aagaaattaa aaaaactaag gaaacatttt tcttgtttcg   9660
agtagataat gccagcctgt taaacgccgt cgacgagtct aacggacacc aaccagcgaa   9720
ccagcagcgt cgcgtcgggc caagcgaagc agacggcacg gcatctctgt cgctgcctct   9780
ggacccctct cgagagttcc gctccaccgt tggacttgct ccgctgtcgg catccagaaa   9840
ttgcgtggcg gagcggcaga cgtgagccgg cacggcaggc ggcctcctcc tcctctcacg   9900
gcaccggcag ctacggggga ttcctttccc accgctcctt cgctttccct tcctcgcccg   9960
ccgtaataaa tagacacccc ctccacaccc tctttcccca acctcgtgtt gttcggagcg  10020
cacacacaca caaccagatc tcccccaaat ccacccgtcg gcacctccgc ttcaaggtac  10080
gccgctcgtc ctcccccccc cccctctct accttctcta gatcggcgtt ccggtccatg  10140
gttagggccc ggtagttcta cttctgttca tgtttgtgtt agatccgtgt ttgtgttaga  10200
tccgtgctgc tagcgttcgt acacggatgc gacctgtacg tcagacacgt tctgattgct  10260
aacttgccag tgtttctctt tggggaatcc tgggatggct ctagccgttc cgcagacggg  10320
atcgatttca tgattttttt tgtttcgttg catagggttt ggtttgccct tttcctttat  10380
ttcaatatat gccgtgcact tgtttgtcgg gtcatctttt catgcttttt tttgtcttgg  10440
ttgtgatgat gtggtctggt tgggcggtcg ttctagatcg gagtagaatt ctgtttcaaa  10500
ctacctggtg gatttattaa ttttggatct gtatgtgtgt gccatacata ttcatagtta  10560
cgaattgaag atgatggatg gaaatatcga tctaggatag gtatacatgt tgatgcgggt  10620
tttactgatg catatacaga gatgcttttt gttcgcttgg ttgtgatgat gtggtgtggt  10680
tgggcggtcg ttcattcgtt ctagatcgga gtagaatact gtttcaaact acctggtgta  10740
tttattaatt ttggaactgt atgtgtgtgt catacatctt catagttacg agtttaagat  10800
ggatggaaat atcgatctag gataggtata catgttgatg tgggttttac tgatgcatat  10860
acatgatggc atatgcagca tctattcata tgctctaacc ttgagtacct atctattata  10920
ataaacaagt atgttttata attattttga tcttgatata cttggatgat ggcatatgca  10980
gcagctatat gtggattttt ttagccctgc cttcatacgc tatttatttg cttggtactg  11040
tttcttttgt cgatgctcac cctgttgttt ggtgttactt ctgcagggat ccatgagccc  11100
agaacgacgc ccggccgaca tccgccgtgc caccgaggcg gacatgccgg cggtctgcac  11160
catcgtcaac cactacatcg agacaagcac ggtcaacttc cgtaccgagc cgcaggaacc  11220
gcaggagtgg acggacgacc tcgtccgtct gcgggagcgc tatccctggc tcgtcgccga  11280
ggtggacggc gaggtcgccg gcatcgccta cgcgggcccc tggaaggcac gcaacgccta  11340
cgactggacg gccgagtcga ccgtgtacgt ctccccccgc caccagcgga cgggactggg  11400
ctccacgctc tacacccacc tgctgaagtc cctggaggca cagggcttca agagcgtggt  11460
```

-continued

```
cgctgtcatc gggctgccca acgacccgag cgtgcgcatg cacgaggcgc tcggatatgc  11520
cccccgcggc atgctgcggg cggccggctt caagcacggg aactggcatg acgtgggttt  11580
ctggcagctg gacttcagcc tgccggtacc gccccgtccg gtcctgcccg tcaccgagat  11640
cgatcgttca aacatttggc aataaagttt cttaagattg aatcctgttg ccggtcttgc  11700
gatgattatc atataatttc tgttgaatta cgttaagcat gtaataatta acatgtaatg  11760
catgacgtta tttatgagat gggtttttat gattagagtc ccgcaattat acatttaata  11820
cgcgatagaa aacaaaatat agcgcgcaaa ctaggataaa ttatcgcgcg cggtgtcatc  11880
tatgttacta gatctgctac aggcatcgtg gtgtcacgct cgtcgtttgg tatggcttca  11940
ttcagctccg gttcccaacg atcaaggcga gttacatgat cccccatgtt gtgcaaaaaa  12000
gcggttagct ccttcggtcc tccgatcgtt gtcagaagta agttggccgc agtgttatca  12060
ctcatggtta tggcagcact gcataattct cttactgtca tgccatccgt aagatgcttt  12120
tctgtgactg gtgagtactc aaccaagtca ttctgagaat agtgtatgcg gcgaccgagt  12180
tgctcttgcc cggcgtcaat acgggataat accgcgccac atagcagaac tttaaaagtg  12240
ctcatcattg gaaaacgttc ttcggggcga aaactctcaa ggatcttacc gctgttgaga  12300
tccagttcga tgtaacccac tcgtgcaccc aactgatctt cagcatcttt tactttcacc  12360
agcgtttctg ggtgagcaaa aacaggaagg caaaatgccg caaaaaaggg aataagggcg  12420
acacggaaat gttgaatact catactcttc ctttttcaat attattgaag catttatcag  12480
ggttattgtc tcatgagcgg atacatattt gaatgtattt agaaaaataa acaaataggg  12540
gttccgcgca catttccccg aaaagtgcca cctgacgtct aagaaaccat tattatcatg  12600
acattaacct ataaaaatag gcgtatcacg aggccctttc gtctcgcgcg tttcggtgat  12660
gacggtgaaa acctctgaca catgcagctc ccggagacgg tcacagcttg tctgtaagcg  12720
gatgccggga gcagacaagc ccgtcagggc gcgtcagcgg gtgttggcgg gtgtcggggc  12780
tggcttaact atgcggcatc agagcagatt gtactgagag tgcaccatat gcggtgtgaa  12840
ataccgcaca gatgcgtaag gagaaaatac cgcatcaggc gccattcgcc attcaggctg  12900
cgcaactgtt gggaagggcg atcggtgcgg gcctcttcgc tattacgcca gctggcgaaa  12960
gggggatgtg ctgcaaggcg attaagttgg gtaacgccag ggttttccca gtcacgacgt  13020
tgtaaaacga cggccagtgc caagcttgca tgcctgcagt gcagcgtgac ccggtcgtgc  13080
ccctctctag agataatgag cattgcatgt ctaagttata aaaaattacc acatattttt  13140
tttgtcacac ttgtttgaag tgcagtttat ctatctttat acatatattt aaactttact  13200
ctacgaataa tataatctat agtactacaa taatatcagt gttttagaga atcatataaa  13260
tgaacagtta gacatggtct aaaggacaat tgagtatttt gacaacagga ctctacagtt  13320
ttatcttttt agtgtgcatg tgttctcctt ttttttttgca aatagcttca cctatataat  13380
acttcatcca ttttattagt acatccattt agggtttagg gttaatggtt tttatagact  13440
aattttttta gtacatctat tttattctat tttagcctct aaattaagaa aactaaaact  13500
ctattttagt ttttttattt aataatttag atataaaata gaataaaata aagtgactaa  13560
aaattaaaca aatacccttt aagaaattaa aaaaactaag gaaacatttt tcttgtttcg  13620
agtagataat gccagcctgt taaacgccgt ttgttgaata gaatacaaac cctagaaaaa  13680
caaggcacat ctcggcgccg ccaatagaag gcagaaaccc tagccgtcat ttttcttgaa  13740
gaatatagag cgacgtcgat aggaagatac ttaaatgttg aatccaagca cctagaataa  13800
tgagttagat tagaagaaaa ctatcaactt cgaaatcaag aagaaatgtt ttattctgtt  13860
```

```
gcataaaact ttcgcgtgga gaagctctgt tcagagcccg ggtagccact gggcacgtct  13920
cctagatact ggactcatcg gacgctctcc tcgagccatt aatatggtcc gtcctgtaga  13980
aaccccaacc cgtgaaatca aaaaactcga cggcctgtgg gcattcagtc tggatcgcga  14040
aaactgtgga attgatcagc gttggtggga aagcgcgtta caagaaagcc gggcaattgc  14100
tctcctgttc cgaccctgcc gcttaccgga tacctgtccg cctttctccc ttcgggaagc  14160
gtggcgcttt ctcatagctc acgctgtagg tatctcagtt cggtgtaggt cgttcgctcc  14220
aagctcggca tccggtcagt ggcagtgaag ggcgaacagt tcctgattaa ccacaaaccg  14280
ttctacttta ctggctttgg tcgtcatgaa gatgcggact tgcgtggcaa aggattcgat  14340
aacgtgctga tggtgcacga ccacgcattg atggactgga ttggggccaa ctcctaccgt  14400
acctcgcatt acccttacgc tgaagagatg ctcgactggg cagatgaaca tggcatcgtg  14460
gtgattgatg aaactgctgc tgtcggcttt aacctctctt taggcattgg tttcgaagcg  14520
ggcaacaagc cgaaagaact gtacagcgaa gaggcagtca acggggaaac tcagcaagcg  14580
cacttacagg cgattaaaga gctgatagcg cgtgacaaaa accacccaag cgtggtgatg  14640
tggagtattg ccaacgaacc ggatacccgt ccgcaaggtg cacgggaata tttcgcgcca  14700
ctggcggaag caacgcgtaa actcgacccg acgcgtccga tcacctgcgt caatgtaatg  14760
ttctgcgacg ctcacaccga taccatcagc gatctctttg atgtgctgtg cctgaaccgt  14820
tattacggat ggtatgtcca aagcggcgat ttggaaacgg cagagaaggt actggaaaaa  14880
gaacttctgg cctggcagga gaaactgcat cagccgatta tcatcaccga atacggcgtg  14940
gatacgttag ccgggctgca ctcaatgtac accgacatgt ggagtgaaga gtatcagtgt  15000
gcatggctgg atatgtatca ccgcgtcttt gatcgcgtca gcgccgtcgt cggtgaacag  15060
gtatggaatt tcgccgattt tgcgacctcg caaggcatat tgcgcgttgg cggtaacaag  15120
aaagggatct tcactcgcga ccgcaaaccg aagtcggcgg ctcgctcagt gtgtgtgact  15180
ctgctggtgc tggggaatgg agctcggggc accgtatttg tagcgcgcgc gccgctgtac  15240
gtggcgccct ggcgcggcta cgtggagggg agctgcgtgc cagaggggag gcgggccgcc  15300
acgtcgcacg gccgtgctta tcgggccatc ggcgaggtgc gtgccagctt gggcgtcgcg  15360
tgtcgtggag cgctcctgct cgcggcggag ctggttgagt ggattgcgat gcggtgcttg  15420
gtacagagct cgatggacaa ctcgaggaga gcgtccgatg agtccagtat ctaggagacg  15480
tgcccagtgg ctacccgggc tctgaacaga gcttctccac gcgaaagttt tatgcaacag  15540
aataaaacat ttcttcttga tttcgaagtt gatagttttc ttctaatcta actcattatt  15600
ctaggtgctt ggattcaaca tttaagtatc ttcctatcga cgtcgctcta tattcttcaa  15660
gaaaaatgac ggctagggtt tctgccttct attggtcatt acgcgcagaa aaaaaggatc  15720
tcaagaagat cctttgatct tttctacggg gtctgacgct cagtggaacg aaaactcacg  15780
ttaagggatt ttggtcatga gattatcaaa aaggatcttc acctagatcc ttttaaatta  15840
aaaatgaagt tttaaatcaa tctaaagtat atatgagtaa acttggtctg acagttttac  15900
caatgcttaa tcagtgaggc acctatctca gcgatctgtc tatttcgttc atccatagtt  15960
gcctgactcc ccgtcgtgta gataactacg atacgggagg gcttaccatc tggccccagt  16020
gctgcaatga taccgcgaga cccacgctca ccggctccag atttatcagc aataaaccag  16080
ccagccggaa gggccgagcg cagaagtggt cctgcaactt tatccgcctc catccagtct  16140
attaattgtt gccgggaagc tagagtaagt agttcgccag ttaatagttt gcgcaacgtt  16200
```

gttgccattg ctacaggcat cgtggtgtca cgctcgtcgt ttggtatggc ttcattcagc 16260
tccggttccc aacgatcaag gcgagttaca tgatccccca tgttgtgcaa aaaagcggtt 16320
agctccttcg gtcctccgat cgttgtcaga agtaagttgg ccgcagtgtt atcactcatg 16380
gttatggcag cactgcataa ttctcttact gtcatgccat ccgtaagatg cttttctgtg 16440
actggtgagt actcaaccaa gtcattctga gaatagtgta tgcggcgacc gagttgctct 16500
tgcccggcgt caatacggga taataccgcg ccacatagca gaactttaaa agtgctcatc 16560
attggaaaac gttcttcggg gcgaaaactc tcaaggatct taccgctgtt gagatccagt 16620
tcgatgtaac ccactcgtgc acccaactga tcttcagcat cttttacttt caccagcgtt 16680
tctgggtgag caaaaacagg aaggcaaaat gccgcaaaaa agggaataag ggcgacacgg 16740
aaatgttgaa tactcatact cttccttttt caatattatt gaagcattta tcagggttat 16800
tgtctcatga gcggatacat atttgaatgt atttagaaaa ataaacaaat aggggttccg 16860
cgcacatttc cccgaaaagt gccacctgac gtctaagaaa ccattattat catgacatta 16920
acctataaaa ataggcgtat cacgaggccc tttcgtctcg cgcgtttcgg tgatgacggt 16980
gaaaacctct gacacatgca gctcccggag acggtcacag cttgtctgta agcggatgcc 17040
gggagcagac aagcccgtca gggcgcgtca gcgggtgttg gcgggtgtcg gggctggctt 17100
aactatgcgg catcagagca gattgtactg agagtgcacc atatgcggtg tgaaataccg 17160
cacagatgcg taaggagaaa ataccgcatc aggcgccatt cgccattcag gctgcgcaac 17220
tgttgggaag ggcgatcggt gcgggcctct tcgctattac gccagctggc gaaaggggga 17280
tgtgctgcaa ggcgattaag ttgggtaacg ccagggtttt cccagtcacg acgttgtaaa 17340
acgacggcca gtgccaagct tgcatgcctg cagtgcagcg tgacccggtc gtgcccctct 17400
ctagagataa tgagcattgc atgtctaagt tataaaaaat taccacatat ttttttgtc 17460 acacttgttt gaagtgcagt ttatctatct ttatacatat atttaaactt tactctacga 17520
ataatataat ctatagtact acaatgtacg ccgctcgtcc tcccccccc cccctctcta 17580 ccttctctag atcggcgttc cggtccatgg ttagggcccg gtagttctac ttctgttcat 17640
gtttgtgtta gatccgtgtt tgtgttagat ccgtgctgct agcgttcgta cacggatgcg 17700
acctgtacgt cagacacgtt ctgattgcta acttgccagt gtttctcttt ggggaatcct 17760
gggatggctc tagccgttcc gcagacggga tcgatttcat gatttttttt gtttcgttgc 17820
atagggtttg gtttgccctt ttcctttatt tcaatatatg ccgtgcactt gtttgtcggg 17880
tcatcttttc atgctttttt ttgtcttggt tgtgatgatg tggtctggtt gggcggtcgt 17940
tctagatcgg agtagaattc tgtttcaaac tacctggtgg atttattaat tttggatctg 18000
tatgtgtgtg ccatacatat tcatagttac gaattgaaga tgatggatgg aaatatcgat 18060
ctaggatagg tatacatgtt gatgcgggtt ttactgatgc atatacagag atgctttttg 18120
ttcgcttggt tgtgatgatg tggtgtggtt gggcggtcgt tcattcgttc tagatcggag 18180
tagaatactg tttcaaacta cctggtgtat ttattaattt tggaactgta tgtgtgtgtc 18240
atacatcttc atagttacga gtttaagatg gatggaaata tcgatctagg ataggtatac 18300
atgttgatgt gggttttact gatgcatata catgatggca tatgcagcat ctattcatat 18360
gctctaacct tgagtaccta tctattataa taaacaagta tgttttataa ttattttgat 18420
cttgatatac ttggatgatg gcatatgcag cagctatatg tggatttttt tagccctgcc 18480
ttcatacgct atttatttgc ttggtactgt ttcttttgtc gatgctcacc ctgttgtttg 18540
gtgttacttc tgcagtcgac tcgtagagga tccatcccga ttaggaaagt agagcatgag 18600

```
cccagaacga cgcccggccg acatccgccg tgccaccgag gcggacatgc cggcggtctg  18660
caccatcgtc aaccactaca tcgagacaag cacggtcaac ttccgtaccg agccgcagga  18720
accgcaggag tggacggacg acctcgtccg tctgcgggag cgctatccct ggctcgtcgc  18780
cgaggtggac ggcgaggtcg ccggcatcgc ctacgcgggc ccctggaagg cacgcaacgc  18840
ctacgactgg acggccgagt cgaccgtgta cgtctccccc cgccaccagc ggacgggact  18900
gggctccacg ctctacaccc acctgctgaa gtccctggag gcacagggct tcaagagcgt  18960
ggtcgctgtc atcgggctgc ccaacgaccc gagcgtgcgc atgcacgagg cgctcggata  19020
tgccccccgc ggcatgctgc gggcggccgg cttcaagcac gggaactggc atgacgtggg  19080
tttctggcag ctggacttca gcctgccggt accgccccgt ccggtcctgc ccgtcaccga  19140
gatcatatga atagatgctg catatgccat catgtatatg catcagtaaa acccacatca  19200
acatgtatac ctatcctaga tcgatatttc catccatctt aaactcgtaa ctatgaagat  19260
gtatgacaca cacatacagt tccaaaattt ataaatacac caggtagttt gaaacagtat  19320
tctactccga tctagaacga atgaacgacc gcccaaccac accacatcat cacaaccaag  19380
cgaacaaaaa gcatctctgt atatgcatca gtaaaacccg catcaacatg tatacctatc  19440
ctagatcgat atttccatcc atcatcttca attcgtaact atgaatatgt atggcacaca  19500
catacagatc caaaattaat aaatccacca ggtagtttga aacagaattc tactccgatc  19560
tagaacgacc gcccaaccag accacatcat cacaaccaag acaaaaaaaa gcatgaaaag  19620
atgacccgac aaacaagtgc acggcatata ttgaaataaa ggaaaagggc aaaccaaacc  19680
ctatgcaacg aaacaaaaaa aatcatgaaa tcgatcccgt ctgcggaacg gctagagcca  19740
tcccaggatt ccccaaagag aaacactggc aagttagcaa tcagaacgtg tctgacgtac  19800
aggtcgcatc cgtgtacgaa cgctagcagc acggatctaa cacaaacacg gatctaacac  19860
aaacatgaac agaagtagaa ctaccgggcc ctaaccatgg accggaacgc cgatctagag  19920
aaggtagaga gggggggggg gggaggacga gcggcgtacg ccgacgggtg gatttggggg  19980
agatctggtt gtgtgtgtgt gcgctccgaa caacacgagg ttggggaaag agggtgtgga  20040
gggggtgtct atttattacg gcgggcgagg aagggaaagc gaaggagcgg tgggaaagga  20100
atcccccgta gctgccggtg ccgtgagagg aggaggaggc cgcctgccgt gccggctcac  20160
gtctgccgct ccgccacgca atttctggat gccgacagcg gagcaagtcc aacggtggag  20220
cggaactctc gagaggggtc cagaggcagc gacagagatg ccgtgccgtc tgcttcgctt  20280
ggcccgacgc gacgctgctg gttcgctggt tggtgtccgt tagactcgtc gacggcgttt  20340
aacaggctgg cattatctac tcgaaacaag aaaaatgttt ccttagtttt tttaatttct  20400
taaagggtat ttgtttaatt tttagtcact ttattttatt ctattttata tctaaattat  20460
taaataaaaa aactaaaata gagttttagt tttcttaatt tagaggctaa aatagaataa  20520
aatagatgta ctaaaaaaat tagtctataa aaaccattaa ccctaaaccc taaatggatg  20580
tactaataaa atggatgaag tattatatag gtgaagctat ttgcaaaaaa aaaggagaac  20640
acatgcacac taaaaagata aaactgtaga gtcctgttgt caaaatactc aattgtcctt  20700
tagaccatgt ctaactgttc atttatatga ttctctaaaa cactgatatt attgtagtac  20760
tatagattat attattcgta gagtaaagtt taaatatatg tataaagata gataaactgc  20820
acttcaaaca agtgtgacaa aaaaaatatg tggtaatttt ttataactta gacatgcaat  20880
gctcattatc tctagagagg ggcacgaccg ggtcacgctg cactgcaggc atgcaagctt  20940
```

```
gcactggccg tcgttttaca acgtcgtgac tgggaaaacc ctggcgttac ccaacttaat  21000
cgccttgcag cacatccccc tttcgccagc tggcgtaata gcgaagaggc ccgcaccgat  21060
cgcccttccc aacagttgcg cagcctgaat ggcgaatggc gcctgatgcg gtattttctc  21120
cttacgcatc tgtgcggtat ttcacaccgc atatggtgca ctctcagtac aatctgctct  21180
gatgccgcat agttaagcca gccccgacac ccgccaacac ccgctgacgc gccctgacgg  21240
gcttgtctgc tcccggcatc cgcttacaga caagctgtga ccgtctccgg gagctgcatg  21300
tgtcagaggt tttcaccgtc atcaccgaaa cgcgcgagac gaaagggcct cgtgatacgc  21360
ctatttttat aggttaatgt catgataata atggtttctt agacgtcagg tggcactttt  21420
cggggaaatg tgcgcggaac ccctatttgt ttatttttct aaatacattc aaatatgtat  21480
ccgctcatga gacaataacc ctgataaatg cttcaataat attgaaaaag gaagagtatg  21540
agtattcaac atttccgtgt cgcccttatt cccttttttg cggcattttg ccttcctgtt  21600
tttgctcacc cagaaacgct ggtgaaagta aaagatgctg aagatcagtt gggtgcacga  21660
gtgggttaca tcgaactgga tctcaacagc ggtaagatcc ttgagagttt tcgccccgaa  21720
gaacgttttc caatgatgag cacttttaaa gttctgctat gtggcgcggt attatcccgt  21780
attgacgccg ggcaagagca actcggtcgc cgcatacact attctcagaa tgacttggtt  21840
gagtactcac cagtcacaga aaagcatctt acggatggca tgacagtaag agaattatgc  21900
agtgctgcca taaccatgag tgataacact gcggccaact tacttctgac aacgatcgga  21960
ggaccgaagg agctaaccgc ttttttgcac aacatggggg atcatgtaac tcgccttgat  22020
cgttgggaac cggagctgaa tgaagccata ccaaacgacg agcgtgacac cacgatgcct  22080
gtagcaatgg caacaacgtt gcgcaaacta ttaactggcg aactacttac tctagcttcc  22140
cggcaacaat taatagactg gatggaggcg gataaagttg caggaccact tctgcgctcg  22200
gcccttccgg ctggctggtt tattgctgat aaatctggag ccggtgagcg tgggtctcgc  22260
ggtatcattg cagcactggg gccagatggt aagccctccc gtatcgtagt tatctacacg  22320
acggggagtc aggcaactat ggatgaacga aatagacaga tcgctgagat aggtgcctca  22380
ctgattaagc attggtaact gtcagaccaa gtttactcat atatacttta gattgattta  22440
aaacttcatt tttaatttaa aaggatctag gtgaagatcc tttttgataa tctcatgacc  22500
aaaatccctt aacgtgagtt ttcgttccac tgagcgtcag accccgtaga aaagatcaaa  22560
ggatcttctt gagatccttt ttttctgcgc gtaatctgct gcttgcaaac aaaaaaacca  22620
ccgctaccag cggtggtttg tttgccggat caagagctac caactctttt tccgaaggta  22680
actggcttca gcagagcgca gataccaaat actgtccttc tagtgtagcc gtagttaggc  22740
caccacttca agaactctgt agcaccgcct acatacctcg ctctgctaat cctgttacca  22800
gtggctgctg ccagtggcga taagtcgtgt cttaccgggt tggactcaag acgatagtta  22860
ccggataagg cgcagcggtc gggctgaacg gggggttcgt gcacacagcc cagcttggag  22920
cgaacgacct acaccgaact gagataccta cagcgtgagc tatgagaaag cgccacgctt  22980
cccgaaggga gaaaggcgga caggtatccg gtaagcggca gggtcggaac aggagagcgc  23040
acgagggagc ttccaggggg aaacgcctgg tatctttata gtcctgtcgg gtttcgccac  23100
ctctgacttg agcgtcgatt tttgtgatgc tcgtcagggg ggcggagcct atggaaaaac  23160
gccagcaacg cggccttttt acggttcctg gccttttgct ggccttttgc tcacatgttc  23220
tttcctgcgt tatcccctga ttctgtggat aaccgtatta ccgcctttga gtgagctgat  23280
accgctcgcc gcagccgaac gaccgagcgc agcgagtcag tgagcgagga agcggaagag  23340
```

-continued

```
cgcccaatac gcaaaccgcc tctccccgcg cgttggccga ttcatttatg cagctggcac  23400
gacaggtttc ccgactggaa agcgggcagt gagcgcaacg caatttatgt gagttagctc  23460
actcattagg caccccaggc tttacacttt atgcttccgg ctcgtatgtt aagcttgcat  23520
gcctgcagtg cagcgtgacc cggtcgtgcc cctctctaga gataatgagc attgcatgtc  23580
taagttataa aaaattacca catatttttt ttgtcacact tgtttgaagt gcagtttatc  23640
tatctttata catatattta aactttactc tacgaataat ataatctata gtactacaat  23700
aatatcagtg ttttagagaa tcatataaat gaacagttag acatggtcta aaggacaatt  23760
gagtattttg acaacaggac tctacagttt tatcttttta gtgtgcatgt gttctccttt  23820
tttttgcaa atagcttcac ctatataata cttcatccat tttattagta catccattta  23880
gggtttaggg ttaatggttt ttatagacta atttttttag tacatctatt ttattctatt  23940
ttagcctcta aattaagaaa actaaaactc tattttagtt tttttattta ataatttaga  24000
tataaaatag aataaaataa agtgactaaa aattaaacaa atacccttta agaaattaaa  24060
aaaactaagg aaacattttt cttgtttcga gtagataatg ccagcctgtt aaacgccgtc  24120
gacgagtcta acggacacca accagcgaac cagcagcgtc gcgtcgggcc aagcgaagca  24180
gacggcacgg catctctgtc gctgcctctg gacccctctc gagagttccg ctccaccgtt  24240
ggacttgctc cgctgtcggc atccagaaat tgcgtggcgg agcggcagac gtgagccggc  24300
acggcaggcg gcctcctcct cctctcacgg caccggcagc tacgggggat tcctttccca  24360
ccgctccttc gctttccctt cctcgcccgc cgtaataaat agacacccga actgtatgtg  24420
tgtgtcatac atcttcatag ttacgagttt aagatggatg gaaatatcga tctaggatag  24480
gtatacatgt tgatgtgggt tttactgatg catatacatg atggcatatg cagcatctat  24540
tcatatgctc taaccttgag tacctatcta ttataataaa caagtatgtt ttataattat  24600
tttgatcttg atatacttgg atgatggcat atgcagcagc tatatgtgga tttttttagc  24660
cctgccttca tacgctattt atttgcttgg tactgtttct tttgtcgatg ctcaccctgt  24720
tgtttggtgt tacttctgca gggatccatg tctcttcaac aagtaacaac caccaggaag  24780
aaccgaaacg aggggcggag acgatttacc gacaaacaaa taagtttcct agagtacatg  24840
tttgagacac agtcgagacc cgagttaagg atgaaacacc agttggcaca taaactcggg  24900
cttcatcctc gtcaagtggc gatatggttc cagaacaaac gcgcgcgatc aaagtcgagg  24960
cagattgagc aagagtataa cgcgctaaag cataactacg agacgcttgc gtctaaatcc  25020
gagtctctaa agaaagagaa tcaggcccta ctcaatcaat tggaggtgct gagaaatgta  25080
gccgaaaagc atcaagagaa aactagtagt agtggcagcg gtgaagaatc ggatgatcgg  25140
tttacgaact ctccggacgt tatgtttggt caagaaatga atgttccgtt ttgcgacggt  25200
tttgcgtacc ttgaagaagg aaacagtttg ttggagattg aagaacaact gccagacctt  25260
caaaagtggt gggagttcga tcgttcaaac atttggcaat aaagtttctt aagattgaat  25320
cctgttgccg gtcttgcgat gattatcata taatttctgt tgaattacgt taagcatgta  25380
ataattaaca tgtaatgcat gacgttattt atgagatggg tttttatgat tagagtcccg  25440
caattataca tttaatacgc gatagaaaac aaaatatagc gcgcaaacta ggataaatta  25500
tcgcgcgcgg tgtcatctat gttactagat cggaattcgt aatcatggtc atagctgttt  25560
cctgtgtgaa attgttatcc gctcacaatt ccacacaaca tacgagccgg aagcataaag  25620
tgtaaagcct ggggtgccta atgagtgagc taactcacat taattgcgtt gcgctcactg  25680
```

-continued

```
cccgctttcc agtcgggaaa cctgtcgtgc cagctgcatt aatgaatcgg ccaacgcgcg  25740
gggagaggcg gtttgcgtat tgggcgctct tccgcttcct cgctcactga ctcgctgcgc  25800
tcggtcgttc ggctgcggcg agcggtatca gctcactcaa aggcggtaat acggttatcc  25860
acagaatcag gggataacgc aggaaagaac atgtgagcaa aaggccagca aaaggccagg  25920
aaccgtaaaa aggccgcgtt gctggcgttt ttccataggc tccgcccccc tgacgagcat  25980
cacaaaaatc gacgctcaag tcagaggtgg cgaaacccga caggactata aagataccag  26040
gcgtttcccc ctggaagctc cctcgtgcgc tctcctgttc cgaccctgcc gcttaccgga  26100
tacctgtccg cctttctccc ttcgggaagc gtggcgcttt ctcatagctc acgctgtagg  26160
tatctcagtt cggtgtaggt cgttcgctcc aagctgggct gtgtgcacga accccccgtt  26220
cagcccgacc gctgcgcctt atccggtaac tatcgtcttg agtccaaccc ggtaagacac  26280
gacttatcgc cactggcagc agccactggt aacaggatta gcagagcgag gtatgtaggc  26340
ggtgctacag agttcttgaa gtggtggcct aactacggct acactagaag gacagtattt  26400
ggtatctgcg ctctgctgaa gccagttacc ttcggaaaaa gagttggtag ctcttgatcc  26460
ggcaaacaaa ccaccgctgg tagcggtggt ttttttgttt gcaagcagca gattacgcgc  26520
agaaaaaaag gatctcaaga agatcctttg atcttttcta cggggtctga cgctcagtgg  26580
aacgaaaact cacgttaagg gattttggtc atgagattat caaaaaggat cttcacctag  26640
atccttttaa attaaaaatg aagttttaaa tcaatctaaa gtatatatga gtaaacttgg  26700
tctgacagtt gatcgttggg aaccggagct gaatgaagcc ataccaaacg acgagcgtga  26760
caccacgatg cctgtagcaa tggcaacaac gttgcgcaaa ctattaactg gcgaactact  26820
tactctagct tcccggcaac aattaataga ctggatggag gcggataaag ttgcaggacc  26880
acttctgcgc tcggcccttc cggctggctg gtttattgct gataaatctg gagccggtga  26940
gcgtgggtct cgcggtatca ttgcagcact ggggccagat ggtaagccct cccgtatcgt  27000
agttatctac acgacgggga gtcaggcaac tatggatgaa cgaaatagac agatcgctga  27060
gatagaactg tcagaccaag tttactcata tatactttag attgatttaa aacttcattt  27120
ttaatttaaa aggatctagg tgaagatcct ttttgataat ctcatgacca aaatccctta  27180
acgtgagttt tcgttccact gagcgtcaga ccccgtagaa aagatcaaag gatcttcttg  27240
agatcctttt tttctgcgcg taatctgctg cttgcaaaca aaaaaaccac cgctaccagc  27300
ggtggtttgt ttgccggatc aagagctacc aactcttttt ccgaaggtaa ctggcttcag  27360
cagagcgcag ataccaaata ctgtccttct agtgtagccg tagttaggcc accacttcaa  27420
gaactctgta gcaccgccta catacctcgc tctgctaatc ctgttaccag tggctgctgc  27480
cagtggcgat aagtcgtgtc ttaccgggtt ggactcaaga cgatagttac cggataaggc  27540
gcagcggtcg ggctgaacgg ggggttcgtg cacacagccc agcttggagc gaacgaccta  27600
caccgaactg agatacctac agcgtgagct atgagaaagc gccacgcttc ccgaagggag  27660
aaaggcggac aggtatccgg taagcggcag ggtcggaaca ggagagcgca cgagggagct  27720
tccaggggga aacgcctggt atctttatag tcctgtcggg tttcgccacc tctgacttga  27780
gcgtcgattt ttgtgatgct cgtcaggggg gcggagccta tggaaaaacg ccagcaacgc  27840
gacgctgggc cgccttttta cggttcctgg ccttttgctg gccttttgct cacatgttct  27900
ttcctgcgtt atcccctgat tctgtggata accgtattac cgcctttgag tgagctgata  27960
gtgtcacgca gatcctatga aatttggtcg atgattgtct tttatggatc cgttcagacc  28020
aagtcttcgt gtgtctatgt tatcgtgcct ttaaattgaa tcctttcgat ttatgcttct  28080
```

-continued

```
ttttgtcagc ggtggttgat cttctgatgt gctggttaca aagggtctta gcataacaat  28140
tttccaattg tctactacaa caagttttgt ctaacttcga tgaagcctag gtgatgacga  28200
tttcaacttg cttcggtgct tgtaactgtt attagatggt ctacggatct aaatgtaact  28260
tctattattt gttgtgtttt ttgtattatt atgatggatg atgaatagat taaaagatcc  28320
cgcaaataaa accttaaatg ataaatgtca cacgtcacgt gcatggcact ccggccctaa  28380
tgccttttgt agctattcta gtaacgcaag gatagcaaat ttccgtgaca cgacgcaagt  28440
ttttgttaaa aataaattaa agcaagaaaa ttgtcatact tgctaacgaa aattgccatc  28500
cttgcctatt catcatccat cataataata caaaaaacac aacaaataat agaagttaca  28560
tttagatccg tagaccatct aataacagtt acaagcaccg aagcaagttg gtgccgtctg  28620
cttcgcttgg cccgacgcga cgctgctggt tcgctggttg gtgtccgtta gactcgtcga  28680
cggcgtttaa caggctggca ttatctactc gaaacaagaa aaatgtttcc ttagtttttt  28740
taatttctta aagggtattt gtttaatttt tagtcacttt attttattct attttatatc  28800
taaattatta aataaaaaaa ctaaaataga gttttagttt tcttaattta gaggctaaaa  28860
tagaataaaa tagatgtact aaaaactcaa ttgtccttta gaccatgtct aactgttcat  28920
ttatatgatt ctctaaggca ctggccgtcg ttttacaacg tcgtgactgg gaaaaccctg  28980
gcgttaccca acttaatcgc cttgcagcac atcccccttt cgccagctgg cgtaatagcg  29040
aagaggcccg caccgatcgc ccttcccaac agttgcgcag cctgaatggc gaatggcgcc  29100
tgatgcggta ttttctcctt acgcatctgt gcggtatttc acaccgcata tggtgcactc  29160
tcagtacaat ctgctctgat gccgcatagt taagccagcc ccgacacccg ccaacacccg  29220
ctgacgcgcc ctgacgggct tgtctgctcc cggcatccgc ttacagacaa gctgtgaccg  29280
tctccgggag ctgcatgtgt cagaggtttt caccgtcatc accgaaacgc gcgagacgaa  29340
agggcctcgt gatacgccta tttttatagg ttaatgtcat gataataatg gtttcttaga  29400
cgtcaggtgg cacttttcgg ggaaatgtgc gcggaacccc tatttgttta tttttctaaa  29460
tacattacca atgcttaatc agtgaggcac ctatctcagc gatctgtcta tttcgttcat  29520
ccatagttgc ctgactcccc gtcgtgtaga taactacgat acgggagggc ttaccatctg  29580
gccccagtgc tgcaatgata ccgcgagacc cacgctcacc ggctccagat ttatcagcaa  29640
taaaccagcc agccggaagg gccgagcgca gaagtggtcc tgcaacttta tccgcctcca  29700
tccagtctat taattgttgc cgggaagcta gagtaagtag ttcgccagtt aatagtttgc  29760
gcaacgttgt tgccattgct acaggcatcg tggtgtcacg ctcgtcgttt ggtatggctt  29820
cattcagctc cggttcccaa cgatcaaggc gagttacatg atcccccatg ttgtgcaaaa  29880
aagcggttag ctccttcggt cctccgaata ccgcgccaca tagcagaact ttaaaagtgc  29940
tcatcattgg aaaacgttct tcggggcgaa aactctcaag gatcttaccg ctgttgagat  30000
ccagttcgat gtaacccact cgtgcaccca actgatcttc agcatctttt actttcacca  30060
gcgtttctgg gtgagcaaaa acaggaaggc aaaatgccgc aaaaaaggga ataagggcga  30120
cacggaaatg ttgaatactc atactcttcc tttttcaata ttattgaagc atttatcagg  30180
gttattgtct catgagcgga tacatatttg aagatctcgg tgacgggcag gaccggacgg  30240
ggcggtaccg gcaggctgaa gtccagctgc cagaaaccca cgtcatgcca gttcccgtgc  30300
ttgaagccgg ccgcccgcag catgccgcgg ggggcatatc cgagcgcctc gtgcatgcgc  30360
acgctcgggt cgttgggcag cccgatgaca gcgaccacgc tcttgaagcc ctgtgcctcc  30420
```

-continued

```
agggacttca gcaggtgggt gtagagcgtg gagcccagtc ccgtccgctg gtggcggggg  30480
gagacgtaca cggtcgactc ggccgtccag tcgtaggcgt tgcgtgcctt ccaggggccc  30540
gcgtaggcga tgccggcgac ctcgccgtat ggatgaagta ttatataggt gaagctattt  30600
gcaaaaaaaa aggagaacac atgcacacta aaaagataaa actgtagagt cctgttgtca  30660
aaatactcaa ttgtccttta gaccatgtct aactgttcat ttatatgatt ctctaaaaca  30720
ctgatattat tgtagtacta tagattatat tattcgtaga gtaaagttta aatatatgta  30780
taaagataga taaactgcac ttcaaacaag tgtgacaaaa aaaatatgtg gtaatttttt  30840
ataacttaga catgcaatgc tcattatctc tagagagggg cacgaccggg tcacgctgca  30900
ctgcaggcat gcaagcttct gcagaagtaa caccaaacaa cagggtgagc atcgacaaaa  30960
gaaacagtac caagcaaata aatagcgtat gaaggcaggg ctaaaaaaat ccacatatag  31020
ctgctgcata tgccatcatc caagtatatc aagatcaaaa taattataaa acatacttgt  31080
ttattataat agataggtac tcaaggttag agcatatgaa tagatgctgc atatgccatc  31140
atgtatatgc atcagtaaaa cccacatcaa catgtatacc tatcctagat cgatatttcc  31200
atccatctta aactcgtaac tatgaagatg tatgacacac acatacagtt ccaaaattaa  31260
taaatacacc aggtagtttg aaacagtatt ctactccgat ctagaacgaa tgaacgaccg  31320
cccaaccaca ccacatcatc acaaccaagc gaacaaaaag catctctgta tatgcatcag  31380
taaaacccgc atcaacatgt atacctatcc tagatcgata tttccatcca tcatcttcaa  31440
ttcgtaacta tgaatatgta tggcacacac atacagatcc aaaattaata aatccaccag  31500
gtagtttgaa acagaattct actccgatct agaacgaccg cccaaccaga ccacatcatc  31560
acaaccaaga caaaaaaaag catgaaaaga tgacccgaca aacaagtgca cggcatatat  31620
tgaaataaag gaaaagggca aaccaaaccc tatgcaacga aacaaaaaaa atcatgaaat  31680
cgatcccgtc tgcggaacgg ctagagccat cccaggattc cccaaagaga aacactggca  31740
agttagcaat cagaacgtgt ctgacgtaca ggtcgcatcc gtgtacgaac gctagcagca  31800
cggatctaac acaaacacgg atctaacaca aacatgaaca gaagtagaac taccgggccc  31860
taaccatgga ccggaacgcc gatctagaga aggtagagag gggggggggg ggaggacgag  31920
cggcgtacct tgaagcggag gtgccgacgg gtggatttgg gggagatctg gttgtgtgtg  31980
tgtgcgctcc gaacaacacg aggttgggga aagagggtgt ggagggggtg tctatttatt  32040
acggcgggcg aggaagggaa agcgaaggag cggtgggaaa ggaatccccc gtagctgccg  32100
gtgccgtgag aggaggagga ggccgcctgc cgtgccggct cacgtctgcc gctccgccac  32160
gcaatttctg gatgccgaca gcggagcaag tccaacggtg gagcggaact ctcgagaggg  32220
gtccagaggc agcgacagag atgccgtgcc gtctgcttcg cttggcccga cgcgacgctg  32280
ctggttcgct ggttggtgtc cgttagactc gtcgacggcg tttaacaggc tggcattatc  32340
tactcgaaac aagaaaaatg tttccttagt ttttttaatt tcttaaaggg tatttgttta  32400
atttttagtc actttatttt attctatttt atatctaaat tattaaataa aaaaactaaa  32460
atagagtttt agttttctta atttagaggc taaaatagaa taaaatagat gtactaaaaa  32520
aattagtcta taaaaaccat taaccctaaa ccctaaatgg atgtactaat aaaatggatg  32580
aagtattata taggtgaagc tatttgcaaa aaaaaaggag aacacatgca cactaaaaag  32640
ataaaactgt agagtcctgt tgtcaaaata ctcaattgtc ctttagacca tgtctaactg  32700
ttcatttata tgattctcta aaacactgat attattgtag tactatagat tatattattc  32760
gtagagtaaa gtttaaatat atgtataaag atagataaac tgcacttcaa acaagtgtga  32820
```

```
caaaaaaaat atgtggtaat tttttataac ttagacatgc aatgctcatt atctctagag  32880
aggggcacga ccgggtcacg ctgcactgca ggcatgcaag cttgcactgg ccgtcgtttt  32940
acaacgtcgt gactgggaaa accctggcgt tacccaactt aatcgccttg cagcacatcc  33000
ccctttcgcc agctggcgta atagcgaaga ggcccgcacc gatcgccctt cccaacagtt  33060
gcgcagcctg aatggcgaat ggcgcctgat gcggtatttt ctccttacgc atctgtgcgg  33120
tatttcacac cgcatatggt gcactctcag tacaatctgc tctgatgccg catagttaag  33180
ccagccccga cacccgccaa cacccgctga cgcgccctga cgggcttgtc tgctcccggc  33240
atccgcttac agacaagctg tgaccgtctc cgggagctgc atgtgtcaga ggttttcacc  33300
gtcatcaccg aaacgcgcga gacgaaaggg cctcgtgata cgcctatttt tataggttaa  33360
tgtcatgata ataatggttt cttagacgtc aggtggcact tttcggggaa atgtgcgcgg  33420
aacccctatt tgtttatttt tctaaataca ttcaaatatg tatccgctca tgagacaata  33480
accctgataa atgcttcaat aatattgaaa aaggaagagt atgagtattc aacatttccg  33540
tgtcgccctt attccctttt ttgcggcatt ttgccttcct gtttttgctc acccagaaac  33600
gctggtgaaa gtaaaagatg ctgaagatca gttgggtgca cgagtgggtt acatcgaact  33660
ggatctcaac agcggtaaga tccttgagag ttttcgcccc gaagaacgtt ttccaatgat  33720
gagcactttt aaagttctgc tatgtggcgc ggtattatcc cgtattgacg ccgggcaaga  33780
gcaactcggt cgccgcatac actattctca gaatgacttg gttgagtact caccagtcac  33840
agaaaagcat cttacggatg gcatgacagt aagagaatta tgcagtgctg ccataaccat  33900
gagtgataac actgcggcca acttacttct gacaacgatc ggaggaccga aggagctaac  33960
cgcttttttg cacaacatgg gggatcatgt aactcgcctt gatcgttggg aaccggagct  34020
gaatgaagcc ataccaaacg acgagcgtga caccacgatg cctgtagcaa tggcaacaac  34080
gttgcgcaaa ctattaactg gcgaactact tactctagct tcccggcaac aattaataga  34140
ctggatggag gcggataaag ttgcaggacc acttctgcgc tcggcccttc cggctggctg  34200
gtttattgct gataaatctg gagccggtga gcgtgggtct cgcggtatca ttgcagcact  34260
ggggccagat ggtaagccct cccgtatcgt agttatctac acgacgggga gtcaggcaac  34320
tatggatgaa cgaaatagac agatcgctga gataggtgcc tcactgatta agcattggta  34380
actgtcagac caagtttact catatatact ttagattgat ttaaaacttc atttttaatt  34440
taaaaggatc taggtgaaga tcctttttga taatctcatg accaaaatcc cttaacgtga  34500
gttttcgttc cactgagcgt cagaccccgt agaaaagatc aaaggatctt cttgagatcc  34560
tttttttctg cgcgtaatct gctgcttgca aacaaaaaaa ccaccgctac cagcggtggt  34620
ttgtttgccg gatcaagagc taccaactct ttttccgaag gtaactggct tcagcagagc  34680
gcagatacca aatactgtcc ttctagtgta gccgtagtta ggccaccact tcaagaactc  34740
tgtagcaccg cctacatacc tcgctctgct aatcctgtta ccagtggctg ctgccagtgg  34800
cgataagtcg tgtcttaccg ggttggactc aagacgatag ttaccggata aggcgcagcg  34860
gtcgggctga acggggggtt cgtgcacaca gcccagcttg gagcgaacga cctacaccga  34920
actgagatac ctacagcgtg agctatgaga aagcgccacg cttcccgaag ggagaaaggc  34980
ggacaggtat ccggtaagcg gcagggtcgg aacaggagag cgcacgaggg agcttccagg  35040
gggaaacgcc tggtatcttt atagtcctgt cgggtttcgc cacctctgac ttgagcgtcg  35100
atttttgtga tgctcgtcag gggggcggag cctatggaaa aacgccagca acgcggcctt  35160
```

-continued

```
tttacggttc ctggcctttt gctggccttt tgctcacatg ttctttcctg cgttatcccc  35220
tgattctgtg gataaccgta ttaccgcctt tgagtgagct gataccgctc gccgcagccg  35280
aacgaccgag cgcagcgagt cagtgagcga ggaagcggaa gagcgcccaa tacgcaaacc  35340
gcctctcccc gcgcgttggc cgattcatta atgcagctgg cacgacaggt ttcccgactg  35400
gaaagcgggc agtgagcgca acgcaattaa tgtgagttag ctcactcatt aggcacccca  35460
ggctttacac tttatgcttc cggctcgtat gttgtgtgga attgtgagcg gataacaatt  35520
tcacacagga aacagctatg accatgatta cgaattccga tcgttcaaac atttggcaat  35580
aaagtttctt aagattgaat cctgttgccg gtcttgcgat gattatcata taatttctgt  35640
tgaattacgt taagcatgta ataattaaca tgtaatgcat gacgttattt atgagatggg  35700
tttttatgat tagagtcccg caattataca tttaatacgc gatagaaaac aaaatatagc  35760
gcgcaaacta ggataaatta tcgcgcgcgg tgtcatctat gttactagat cgatctcggt  35820
gacgggcagg accggacggg gcggtaccgg caggctgaag tccagctgcc agaaacccac  35880
gtcatgccag ttcccgtgct tgaagccggc cgcccgcagc atgccgcggg gggcatatcc  35940
gagcgcctcg tgcatgcgca cgctcgggtc gttgggcagc ccgatgacag cgaccacgct  36000
cttgaagccc tgtgcctcca gggacttcag caggtgggtg tagagcgtgg agcccagtcc  36060
cgtccgctgg tggcgggggg agacgtacac ggtcgactcg gccgtccagt cgtaggcgtt  36120
gcgtgccttc caggggcccg cgtaggcgat gccggcgacc tcgccgtcca cctcggcgac  36180
gagccaggga tagcgctccc gcagacggac gaggtcgtcc gtccactcct gcggttcctg  36240
cggctcggta cggaagttga ccgtgcttgt ctcgatgtag tggttgacga tggtgcagac  36300
cgccggcatg tccgcctcgg tggcacggcg gatgtcggcc gggcgtcgtt ctgggctcat  36360
ggatccaagc ttgcatgcct gcagtgcagc gtgacccggt cgtgcccctc tctagagata  36420
atgagcattg catgtctaag ttataaaaaa ttaccacata tttttttgt cacacttgtt  36480
tgaagtgcag tttatctatc tttatacata tatttaaact ttactctacg aataatataa  36540
tctatagtac tacaataata tcagtgtttt agagaatcat ataaatgaac agttagacat  36600
ggtctaaagg acaattgagt attttgacaa caggactcta cagttttatc tttttagtgt  36660
gcatgtgttc tcctttttt ttgcaaatag cttcacctat ataatacttc atccatttta  36720
ttagtacatc catttagggt ttagggttaa tggtttttat agactaattt ttttagtaca  36780
tctattttat tctattttag cctctaaatt aagaaaacta aaactctatt ttagtttttt  36840
tatttaataa tttagatata aaatagaata aaataaagtg actaaaaatt aaacaaatac  36900
cctttaagaa attaaaaaaa ctaaggaaac atttttcttg tttcgagtag ataatgccag  36960
cctgttaaac gccgtcgacg agtctaacgg acaccaacca gcgaaccagc agcgtcgcgt  37020
cgggccaagc gaagcagacg gcacggcatc tctgtcgctg cctctggacc cctctcgaga  37080
gttccgctcc accgttggac ttgctccgct gtcggcatcc agaaattgcg tggcggagcg  37140
gcagacgtga gccggcacgg caggcggcct cctcctcctc tcacggcacc ggcagctacg  37200
ggggattcct ttcccaccgc tccttcgctt tcccttcctc gcccgccgta ataaatagac  37260
acccctcca caccctcttt ccccaacctc gtgttgttcg gagcgcacac acacacaacc  37320
agatctcccc caaatccacc cgtcggcacc tccgcttcaa ggtacgccgc tcgtcctccc  37380
cccccccccc tctctacctt ctctagatcg gcgttccggt ccatggttag ggcccggtag  37440
ttctacttct gttcatgttt gtgttagatc cgtgtttgtg ttagatccgt gctgctagcg  37500
ttcgtacacg gatgcgacct gtacgtcaga cacgttctga ttgctaactt gccagtgttt  37560
```

ctctttgggg aatcctggga tggctctagc cgttccgcag acgggatcga tttcatgatt 37620
ttttttgttt cgttgcatag ggtttggttt gcccttttcc tttatttcaa tatatgccgt 37680
gcacttgttt gtcgggtcat cttttcatgc ttttttttgt cttggttgtg atgatgtggt 37740
ctggttgggc ggtcgttcta gatcggagta gaattctgtt tcaaactacc tggtggattt 37800
attaatttg gatctgtatg tgtgtgccat acatattcat agttacgaat tgaagatgat 37860
ggatggaaat atcgatctag gataggtata catgttgatg cgggttttac tgatgcatat 37920
acagagatgc tttttgttcg cttggttgtg atgatgtggt gtggttgggc ggtcgttcat 37980
tcgttctaga tcggagtaga atactgtttc aaactacctg gtgtatttat taattttgga 38040
actgtatgtg tgtgtcatac atcttcatag ttacgagttt aagatggatg gaaatatcga 38100
tctaggatag gtatacatgt tgatgtgggt tttactgatg catatacatg atggcatatg 38160
cagcatctat tcatatgctc taaccttgag tacctatcta ttataataaa caagtatgtt 38220
ttataattat tttgatcttg atatacttgg atgatggcat atgcagcagc tatatgtgga 38280
tttttttagc cctgccttca tacgctattt atttgcttgg tactgtttct tttgtcgatg 38340
ctcaccctgt tgtttggtgt tacttctgca gggatccatg agcccagaac gacgcccggc 38400
cgacatccgc cgtgccaccg aggcggacat gccggcggtc tgcaccatcg tcaaccacta 38460
catcgagaca agcacggtca acttccgtac cgagccgcag gaaccgcagg agtggacgga 38520
cgacctcgtc cgtctgcggg agcgctatcc ctggctcgtc gccgaggtgg acggcgaggt 38580
cgccggcatc gcctacgcgg gcccctggaa ggcacgcaac gcctacgact ggacggccga 38640
gtcgaccgtg tacgtctccc cccgccacca gcggacggga ctgggctcca cgctctacac 38700
ccacctgctg aagtccctgg aggcacaggg cttcaagagc gtggtcgctg tcatcgggct 38760
gcccaacgac ccgagcgtgc gcatgcacga ggcgctcgga tatgcccccc gcggcatgct 38820
gcgggcggcc ggcttcaagc acgggaactg gcatgacgtg ggtttctggc agctggactt 38880
cagcctgccg gtaccgcccc gtccggtcct gcccgtcacc gagatctgat ccgtcgacct 38940
gcagatcgtt caaacatttg gcaataaagt ttcttaagat tgaatcctgt tgccggtctt 39000
gcgatgatta tcatataatt tctgttgaat tacgttaagc atgtaataat taacatgtaa 39060
tgcatgacgt tatttatgag atgggttttt atgattagag tcccgcaatt atacatttaa 39120
tacgcgatag aaaacaaaat atagcgcgca aactaggata aattatcgcg cgcggtgtca 39180
tctatgttac tagatcggaa ttcgtaatca tggtcatagc tgtttcctgt gtgaaattgt 39240
tatccgctca caattccaca caacatacga gccggaagca taaagtgtaa agcctggggt 39300
gcctaatgag tgagctaact cacattaatt gcgttgcgct cactgcccgc tttccagtcg 39360
ggaaacctgt cgtgccagct gcattaatga atcggccaac gcgcggggag aggcggtttg 39420
cgtattgggc gctcttccgc ttcctcgctc actgactcgc tgcgctcggt cgttcggctg 39480
cggcgagcgg tatcagctca ctcaaaggcg gtaatacggt tatccacaga atcaggggat 39540
aacgcaggaa agaacatgtg agcaaaaggc cagcaaaagg ccaggaaccg taaaaaggcc 39600
gcgttgctgg cgtttttcca taggctccgc ccccctgacg agcatcacaa aaatcgacgc 39660
tcaagtcaga ggtggcgaaa cccgacagga ctataaagat accaggcgtt tccccctgga 39720
agctccctcg tgcgctctcc tgttccgacc ctgccgctta ccggatacct gtccgccttt 39780
ctcccttcgg gaagcgtggc gctttctcat agctcacgct gtaggtatct cagttcggtg 39840
taggtcgttc gctccaagct gggctgtgtg cacgaacccc ccgttcagcc cgaccgctgc 39900

-continued gccttatccg gtaactatcg tcttgagtcc aacccggtaa gacacgactt atcgccactg 39960
gcagcagcca ctggtaacag gattagcaga gcgaggtatg taggcggtgc tacagagttc 40020
ttgaagtggt ggcctaacta cggctacact agaaggacag tatttggtat ctgcgctctg 40080
ctgaagccag ttaccttcgg aaaaagagtt ggtagctctt gatccggcaa acaaaccacc 40140
gctggtagcg gtggtttttt tgtttgcaag cagcagatta cgcgcagaaa aaaaggatct 40200
caagaagatc ctttgatctt ttctacgggg tctgacgctc agtggaacga aaactcacgt 40260
taagggattt tggtcatgag attatcaaaa aggatcttca cctagatcct tttaaattaa 40320
aaatgaagtt ttaaatcaat ctaaagtata tatgagtaaa cttggtctga cagttaccaa 40380
tgcttaatca gtgaggcacc tatctcagcg atctgtctat ttcgttcatc catagttgcc 40440
tgactccccg tcgtgtagat aactacgata cgggagggct taccatctgg ccccagtgct 40500
gcaatgatac cgcgagaccc acgctcaccg gctccagatt tatcagcaat aaaccagcca 40560
gccggaaggg ccgagcgcag aagtggtcct gcaactttat ccgcctccat ccagtctatt 40620
aattgttgcc gggaagctag agtaagtagt tcgccagtta atagtttgcg caacgttgtt 40680
gccattgcta caggcatcgt ggtgtcacgc tcgtcgtttg gtatggcttc attcagctcc 40740
ggttcccaac gatcaaggcg agttacatga tcccccatgt tgtgcaaaaa agcggttagc 40800
tccttcggtc ctccgatcgt tgtcagaagt aagttggccg cagtgttatc actcatggtt 40860
atggcagcac tgcataattc tcttactgtc atgccatccg taagatgctt ttctgtgact 40920
ggtgagtact caaccaagtc attctgagaa tagtgtatgc ggcgaccgag ttgctcttgc 40980
ccggcgtcaa tacgggataa taccgcgcca catagcagaa ctttaaaagt gctcatcatt 41040
ggaaaacgtt cttcggggcg aaaactctca aggatcttac cgctgttgag atccagttcg 41100
atgtaaccca ctcgtgcacc caactgatct tcagcatctt ttactttcac cagcgtttct 41160
gggtgagcaa aaacaggaag gcaaaatgcc gcaaaaaagg gaataagggc gacacggaaa 41220
tgttgaatac tcatactctt cctttttcaa tattattgaa gcatttatca gggttattgt 41280
ctcatgagcg gatacatatt tgaatgtatt tagaaaaata aacaaatagg ggttccgcgc 41340
acatttcccc gaaaagtgcc acctgacgtc taagaaacca ttattatcat gacattaacc 41400
tataaaaata ggcgtatcac gaggcccttt cgtctcgcgc gtttcggtga tgacggtgaa 41460
aacctctgac acatgcagct cccggagacg gtcacagctt gtctgtaagc ggatgccggg 41520
agcagacaag cccgtcaggg cgcgtcagcg ggtgttggcg ggtgtcgggg ctggcttaac 41580
tatgcggcat cagagcagat tgtactgaga gtgcaccata tgcggtgtga aataccgcac 41640
agatgcgtaa ggagaaaata ccgcatcagg cgccattcgc cattcaggct gcgcaactgt 41700
tgggaagggc gatcggtgcg ggcctcttcg ctattacgcc agctggcgaa agggggatgt 41760
gctgcaaggc gattaagttg ggtaacgcca gggttttccc agtcacgacg ttgtaaaacg 41820
acggccagtg caagcttgca tgcctgcagt gcagcgtgac ccggtcgtgc ccctctctag 41880
agataatgag cattgcatgt ctaagttata aaaaattacc acatattttt tttgtcacac 41940
ttgtttgaag tgcagtttat ctatctttat acatatattt aaactttact ctacgaataa 42000
tataatctat agtactacaa taatatcagt gttttagaga atcatataaa tgaacagtta 42060
gacatggtct aaaggacaat tgagtatttt gacaacagga ctctacagtt ttatcttttt 42120
agtgtgcatg tgttctcctt tttttttgca aatagcttca cctatataat acttcatcca 42180
ttttattagt acatccattt agggtttagg gttaatggtt tttatagact aattttttta 42240
gtacatctat tttattctat tttagcctct aaattaagaa aactaaaact ctattttagt 42300

-continued

```
tttttattt aataatttag atataaaata gaataaaata aagtgactaa aaattaaaca  42360
aatacccttt aagaaattaa aaaaactaag gaaacatttt tcttgtttcg agtagataat  42420
gccagcctgt taaacgccgt cgacgagtct aacggacacc aaccagcgaa ccagcagcgt  42480
cgcgtcgggc caagcgaagc agacggcacg gcatctctgt cgctgcctct ggacccctct  42540
cgagagttcc gctccaccgt tggacttgct ccgctgtcgg catccagaaa ttgcgtggcg  42600
gagcggcaga cgtgagccgg cacggcaggc ggcctcctcc tcctctcacg gcaccggcag  42660
ctacggggga ttcctttccc accgctcctt cgctttccct tcctcgcccg ccgtaataaa  42720
tagacacccc ctccacaccc tctttcccca acctcgtgtt gttcggagcg cacacacaca  42780
caaccagatc tcccccaaat ccacccgtcg gcacctccgc ttcaaggtac gccgctcgtc  42840
ctcccccccc cccccctctct accttctcta gatcggcgtt ccggtccatg gttagggccc  42900
ggtagttcta cttctgttca tgtttgtgtt agatccgtgt ttgtgttaga tccgtgctgc  42960
tagcgttcgt acacggatgc gacctgtacg tcagacacgt tctgattgct aacttgccag  43020
tgtttctctt tggggaatcc tgggatggct ctagccgttc cgcagacggg atcgatttca  43080
tgattttttt tgtttcgttg catagggttt ggtttgccct tttcctttat ttcaatatat  43140
gccgtgcact tgtttgtcgg gtcatctttt catgcttttt tttgtcttgg ttgtgatgat  43200
gtggtctggt tgggcggtcg ttctagatcg gagtagaatt ctgtttcaaa ctacctggtg  43260
gatttattaa ttttggatct gtatgtgtgt gccatacata ttcatagtta cgaattgaag  43320
atgatggatg gaaatatcga tctaggatag gtatacatgt tgatgcgggt tttactgatg  43380
catatacaga gatgcttttt gttcgcttgg ttgtgatgat gtggtgtggt tgggcggtcg  43440
ttcattcgtt ctagatcgga gtagaatact gtttcaaact acctggtgta tttattaatt  43500
ttggaactgt atgtgtgtgt catacatctt catagttacg agtttaagat ggatggaaat  43560
atcgatctag gataggtata catgttgatg tgggttttac tgatgcatat acatgatggc  43620
atatgcagca tctattcata tgctctaacc ttgagtacct atctattata ataaacaagt  43680
atgttttata attattttga tcttgatata cttggatgat ggcatatgca gcagctatat  43740
gtggattttt ttagccctgc cttcatacgc tatttatttg cttggtactg tttcttttgt  43800
cgatgctcac cctgttgttt ggtgttactt ctgcaggtcg actctagagg atccatcgat  43860
taggaagtaa ccatgagccc agaacgacgc ccggccgaca tccgccgtgc caccgaggcg  43920
gacatgccgg cggtctgcac catcgtcaac cactacatcg agacaagcac ggtcaacttc  43980
cgtaccgagc cgcaggaacc gcaggagtgg acggacgacc tcgtccgtct gcgggagcgc  44040
tatccctggc tcgtcgccga ggtggacggc gaggtcgccg gcatcgccta cgcgggcccc  44100
tggaaggcac gcaacgccta cgactggacg gccgagtcga ccgtgtacgt ctcccccccgc  44160
caccagcgga cgggactggg ctccacgctc tacacccacc tgctgaagtc cctggaggca  44220
cagggcttca agagcgtggt cgctgtcatc gggctgccca acgacccgag cgtgcgcatg  44280
cacgaggcgc tcggatatgc cccccgcggc atgctgcggg cggccggctt caagcacggg  44340
aactggcatg acgtgggttt ctggcagctg gacttcagcc tgccggtacc gccccgtccg  44400
gtcctgcccg tcaccgagat ctgatccgtc gacctgcaga tcgttcaaac atttggcaat  44460
aaagtttctt aagattgaat cctgttgccg gtcttgcgat gattatcata taatttctgt  44520
tgaattacgt taagcatgta ataattaaca tgtaatgcat gacgttattt atgagatggg  44580
tttttatgat tagagtcccg caattataca tttaatacgc gatagaaaac aaaatatagc  44640
```

-continued

```
gcgcaaacta ggataaatta tcgcgcgcgg tgtcatctat gttactagat cggaattcgt  44700
aatcatggtc atagctgttt cctgtgtgaa attgttatcc gctcacaatt ccacacaaca  44760
tacgagccgg aagcataaag tgtaaagcct ggggtgccta atgagtgagc taactcacat  44820
taattgcgtt gcgctcactg cccgctttcc agtcgggaaa cctgtcgtgc cagctgcatt  44880
aatgaatcgg ccaacgcgcg gggagaggcg gtttgcgtat tgggcgctct tccgcttcct  44940
cgctcactga ctcgctgcgc tcggtcgttc ggctgcggcg agcggtatca gctcactcaa  45000
aggcggtaat acggttatcc acagaatcag gggataacgc aggaaagaac atgtgagcaa  45060
aaggccagca aaaggccagg aaccgtaaaa aggccgcgtt gctggcgttt ttccataggc  45120
tccgcccccc tgacgagcat cacaaaaatc gacgctcaag tcagaggtgg cgaaacccga  45180
caggactata aagataccag gcgtttcccc ctggaagctc cctcgtgcgc tctcctgttc  45240
cgaccctgcc gcttaccgga tacctgtccg cctttctccc ttcgggaagc gtggcgcttt  45300
ctcatagctc acgctgtagg tatctcagtt cggtgtaggt cgttcgctcc aagctgggct  45360
gtgtgcacga accccccgtt cagcccgacc gctgcgcctt atccggtaac tatcgtcttg  45420
agtccaaccc ggtaagacac gacttatcgc cactggcagc agccactggt aacaggatta  45480
gcagagcgag gtatgtaggc ggtgctacag agttcttgaa gtggtggcct aactacggct  45540
acactagaag gacagtattt ggtatctgcg ctctgctgaa gccagttacc ttcggaaaaa  45600
gagttggtag ctcttgatcc ggcaaacaaa ccaccgctgg tagcggtggt ttttttgttt  45660
gcaagcagca gattacgcgc agaaaaaaag gatctcaaga agatcctttg atcttttcta  45720
cggggtctga cgctcagtgg aacgaaaact cacgttaagg gattttggtc atgagattat  45780
caaaaaggat cttcacctag atccttttaa attaaaaatg aagttttaaa tcaatctaaa  45840
gtatatatga gtaaacttgg tctgacagtt accaatgctt aatcagtgag gcacctatct  45900
cagcgatctg tctatttcgt tcatccatag ttgcctgact ccccgtcgtg tagataacta  45960
cgatacggga gggcttacca tctggcccca gtgctgcaat gataccgcga gacccacgct  46020
caccggctcc agatttatca gcaataaacc agccagccgg aagggccgag cgcagaagtg  46080
gtcctgcaac tttatccgcc tccatccagt ctattaattg ttgccgggaa gctagagtaa  46140
gtagttcgcc agttaatagt ttgcgcaacg ttgttgccat tgctacaggc atcgtggtgt  46200
cacgctcgtc gtttggtatg gcttcattca gctccggttc ccaacgatca aggcgagtta  46260
catgatcccc catgttgtgc aaaaaagcgg ttagctcctt cggtcctccg atcgttgtca  46320
gaagtaagtt ggccgcagtg ttatcactca tggttatggc agcactgcat aattctctta  46380
ctgtcatgcc atccgtaaga tgcttttctg tgactggtga gtactcaacc aagtcattct  46440
gagaatagtg tatgcggcga ccgagttgct cttgcccggc gtcaatacgg gataataccg  46500
cgccacatag cagaacttta aaagtgctca tcattggaaa acgttcttcg gggcgaaaac  46560
tctcaaggat cttaccgctg ttgagatcca gttcgatgta acccactcgt gcacccaact  46620
gatcttcagc atcttttact ttcaccagcg tttctgggtg agcaaaaaca ggaaggcaaa  46680
atgccgcaaa aaagggaata agggcgacac ggaaatgttg aatactcata ctcttccttt  46740
ttcaatatta ttgaagcatt tatcagggtt attgtctcat gagcggatac atatttgaat  46800
gtatttagaa aaataaacaa ataggggttc cgcgcacatt tccccgaaaa gtgccacctg  46860
acgtctaaga aaccattatt atcatgacat taacctataa aaataggcgt atcacgaggc  46920
cctttcgtct cgcgcgtttc ggtgatgacg gtgaaaacct ctgacacatg cagctcccgg  46980
agacggtcac agcttgtctg taagcggatg ccgggagcag acaagcccgt cagggcgcgt  47040
```

```
cagcgggtgt tggcgggtgt cggggctggc ttaactatgc ggcatcagag cagattgtac  47100

tgagagtgca ccatatgcgg tgtgaaatac cgcacagatg cgtaaggaga aaataccgca  47160

tcaggcgcca ttcgccattc aggctgcgca actgttggga agggcgatcg gtgcgggcct  47220

cttcgctatt acgccagctg gcgaaagggg gatgtgctgc aaggcgatta agttgggtaa  47280

cgccagggtt ttcccagtca cgacgttgta aaacgacggc cagtgcgtcg actctagagg  47340

tccctcgacc atggctgtaa ggtcgccgaa tacaagggca tgggtggcga ggcctaagag  47400

gagtataatt tcttagacat ttgtcaatta taaacttctt ggtaaaagag catgtaagcc  47460

gaggaaacag acgacatatt gaacaagacc gacatacaac gtgcacacga caaggttcct  47520

gtcacatgcc catccacacc ctactagatg gctccttgac ggtggacact gtatgacgag  47580

tttcttagaa tgagtttttt aaacacaata c                                 47611
```

<210> SEQ ID NO 6
<211> LENGTH: 20418
<212> TYPE: DNA
<213> ORGANISM: Artificial Sequence
<220> FEATURE:
<223> OTHER INFORMATION: Short insert with flanking regions

<400> SEQUENCE: 6

```
gagcgcgctt tcctatttag gatccaaatt ggcactgata ctaaactgct tagacgaatc     60

gcctggagta aaatcaacaa gctcggtttc agcagccgac ttaaacttca tcgccgggtc    120

atgctcggtg gttggcttct ttagagacgt catatccgcc aggtcaacat tattttgata    180

aaaattcatc tcctctgccg cacaaacaga ctcagcataa gccgcatcgc cttcttcaca    240

ttctagggct acctttcgac tcccattgag ggagtcccgg attagggggt gtttggaaca    300

ccacgatgcc tgtagcaatg gcaacaacgt tgcgcaaact attaactggc gaactactta    360

ctctagcttc ccggtaacaa ttaatagact ggatggaggc ggataaagtt gtaggaccac    420

ttctgcgctc ggcccttccg gctggctggt ttattgctga taaatctgga gccggactct    480

aggcttcccg ggcaacaaat taattagact ggatggaggg ataaagtttg cagaccactt    540

tctgcgctcg gcccttccgc tgggctgttc tatgcccgct gaaatcacca gtctctctct    600

acaaatctat ctctctctat aataatgtgt gagtagttcc cagataaggg aattagggtt    660

cttatagggt ttcgctcatg tgttgagcat ataagaaacc cttagtatgt atttgtattt    720

gggctggctt aactatgcgg catcagagca gattgtactg agagtgcacc atatgcggtg    780

tgaaataccg cacagatgcg taaggagaaa ataccgcatc aggcgccatt cgccattcag    840

gctgcgcaac tgttgggaag ggcgatcggt gcgggcctct tcgctattac gccagctggc    900

gaaaggggga tgtgctgcaa ggcgattaag ttgggtaacg ccagggtttt cccagtcacg    960

acgttgtaaa acgacggcca gtgcaagctt gcatgcctgc agtgcagcgt gacccggtcg   1020

tgcccctctc tagagataat gagcattgca tgtctaagtt ataaaaaatt accacatatt   1080

ttttttgtca cacttgtttg aagtgcagtt tatctatctt tatacatata tttaaacttt   1140

actctacgaa taatataatc tatagtacta caataatatc agtgttttag agaatcatat   1200

aaatgaacag ttagacatgg tctaaaggac aattgagtat tttgacaaca ggactctaca   1260

gttttatctt tttagtgtgc atgtgttctc cttttttttt gcaaatagct tcacctatat   1320

aatacttcat ccattttatt agtacatcca tttagggttt agggttaatg gtttttatag   1380

actaattttt ttagtacatc tattttattc tattttagcc tctaaattaa gaaaactaaa   1440
```

-continued

```
actctatttt agttttttta tttaataatt tagatataaa atagaataaa ataaagtgac   1500
taaaaattaa acaaataccc tttaagaaat taaaaaaact aaggaaacat ttttcttgtt   1560
tcgagtagat aatgccagcc tgttaaacgc cgtcgacgag tctaacggac accaaccagc   1620
gaaccagcag cgtcgcgtcg ggccaagcga agcagacggc acggcatctc tgtcgctgcc   1680
tctggacccc tctcgagagt tccgctccac cgttggactt gctccgctgt cggcatccag   1740
aaattgcgtg gcggagcggc agacgtgagc cggcacggca ggcggcctcc tcctcctctc   1800
acggcaccgg cagctacggg ggattccttt cccaccgctc cttcgctttc ccttcctcgc   1860
ccgccgtaat aaatagacac cccctccaca ccctctttcc ccaacctcgt gttgttcgga   1920
gcgcacacac acacaaccag atctccccca aatccacccg tcggcgtacg ccgctcgtcc   1980
tccccccccc cccctctcta ccttctctag atcggcgttc cggtccatgg ttagggcccg   2040
gtagttctac ttctgttcat gtttgtgtta gatccgtgtt tgtgttagat ccgtgctgct   2100
agcgttcgta cacggatgcg acctgtacgt cagacacgtt ctgattgcta acttgccagt   2160
gtttctcttt ggggaatcct gggatggctc tagccgttcc gcagacggga tcgatttcat   2220
gatttttttt gtttcgttgc atagggtttg gtttgccctt ttcctttatt tcaatatatg   2280
ccgtgcactt gtttgtcggg tcatcttttc atgctttttt ttgtcttcct gtttttgctc   2340
acccagaaac gctggtgaaa gtaaaagatg ctgaagatca gttgggtgca cgagtgggtt   2400
acatcgaact ggatctcaac agcggtaaga tccttgagag ttttcgcccc gaagaacgtt   2460
ttccaatgat gagcactttt aaagttctgc tatgtggcgc ggtattatcc cgtattgacg   2520
ccgggcaaga gcaactcggt cgccgcatac actattctca gaatgacttg gttgagtact   2580
caccagtcac agaaaagcat cttacggatg gcatgacagt aagagaatta tgcagtgctg   2640
ccataaccat gagtgataac actgcggcca acttacttct gacaacgatc ggaggaccga   2700
aggagctaac cgcttttttg cacaacatgg gggatcatgt aactcgcctt gatcgttggg   2760
aaccggagct gaatgaagcc ataccaaacg acgagcgtga caccacgatg cctgtagcaa   2820
tggcaacaac gttgcgcaaa ctattaactg ttattgccgg gaaaagtgta cgtatcaccg   2880
tttgtgtgaa caacgaactg aactggcaga ctatcccctg cagaagtaac accaaacaac   2940
agggtgagca tcgacaaaag aaacagtacc aagcaaataa atagcgtatg aaggcagggc   3000
taaaaaaatc cacatatagc tgctgcatat gccatcatcc aagtatatca agatcaaaat   3060
aattataaaa catacttgtt tattataata gataggtact caaggttaga gcatatgaat   3120
agatgctgca tatgccatca tgtatatgca tcagtaaaac ccacatcaac atgtatacct   3180
atcctagatc gatatttcca tccatcttaa actcgtaact atgaagatgt atgacacaca   3240
catacagttc caaaattaat aaatacacca ggtagtttga aacagtattc tactccgatc   3300
tagaacgaat gaacgaccgc ccaaccacac cacatcatca caaccaagcg aacaaaaagc   3360
atctctgtat atgcatcagt aaaacccgca tcaacatgta tacctatcct agaagtacta   3420
tagattatat tattcgtaga gtaaagttta aatatatgta taaagataga taaactgcac   3480
ttcaaacaag tgtgacaaaa aaaatatgtg gtaatttttt ataacttaga catgcaatgc   3540
tcattatctc tagagagggg cacgaccggg tcacgctgca ctgcaggcat gcaagcttgg   3600
cactggccgt cgttttacaa cgtcgtgact gggaaaaccc tggcgttacc caacttaatc   3660
gccttgcagc acatccccct ttcgccagct ggcgtaatag cgaagaggcc cgcaccgatc   3720
gcccttccca acagttgcgc agcctgaatg gcgaatggcg cctgatgcgg tattttctcc   3780
ttacgcatct gtgcggtatt tcacaccgca tatggtgcac tctcagtaca atctgctctg   3840
```

```
atgccgcata gttaagccag ccccgacacc cgccaacacc cgctgacgcg ccctgacggg   3900
cttgtctgct cccggcatcc gcttacagac aagctgtgac cgtctccggg agctgcatgt   3960
gtcagaggtt ttcaccgtca tcaccgaaac gcgcgagacg aaagggcctc gtgatacgcc   4020
tatttttata ggttaatgtc atgataataa tggtttctta gacgtcaggt ggcacttttc   4080
ggggaaatgt gcgcggaacc cctatttgtt tatttttcta aatacattac caatgcttaa   4140
tcagtgaggc acctatctca gcgatctgtc tatttcgttc atccatagtt gcctgactcc   4200
ccgtcgtgta gataactacg atacgggagg gcttaccatc tggccccagt gctgcaatga   4260
taccgcgaga cccacgctca ccggctccag atttatcagc aataaaccag ccagccggaa   4320
gggccgagcg cagaagtggt cctgcaactt tatccgcctc catccagtct attaattgtt   4380
gccgggaagc tagagtaagt agttcgccag ttaatagttt gcgcaacgtt gttgccattg   4440
ctacaggcat cgtggtgtca cgctcgtcgt ttggtatggc ttcattcagc tccggttccc   4500
aacgatcaag gcgagttaca tgatccccca tgttgtgcaa aaaagcggtt agctccttcg   4560
gtcctccgat cgttgtcaga agtaagttgg ccgcagtgtt atcactcatg gttatggcag   4620
cactgcataa ttctcttact gtcatgccat ccgtaagatg cttttctgtg actggtgagt   4680
actcaaccaa gtcattctga gaatagtgta tgcggcgacc gagttgctct tgcccggcgt   4740
caatacggga taataccgcg ccacatagca gaactttaaa agtgctcatc attggaaaac   4800
gttcttcggg gcgaaaactc tcaaggatct taccgctgtt gagatccagt tcgatgtaac   4860
ccactcgtgc acccaactga tcttcagcat cttttacttt caccagcgtt tctgggtgag   4920
caaaaacagg aaggcaaaat gccgcaaaaa agggaataag ggcgacacgg aaatgttgaa   4980
tactcatact cttccttttt caatattatt gaagcattta tcagggttat tgtctcatga   5040
gcggatacat atttgaaaac tgtcagacca agtttactca tatatacttt agattgattt   5100
aaaacttcat ttttaattta aaaggatcta ggtgaagatc ctttttgata atctcatgac   5160
caaaatccct taacgtgagt tttcgttcca ctgagcgtca gaccccgtag aaaagatcaa   5220
aggatcttct tgagatcctt tttttctgcg cgtaagccaa tagaaggcag aaaccctagc   5280
cgtcattttt cttgaagaat atagagcgac gtcgatagga agatacttaa atgttgaatc   5340
caagcaccta gaataatgag ttagattaga agaaaactat caacttcgaa atcaagaaga   5400
aatgttttat tctgttgcat aaaactttcg cgtggagaag ctctgttcag agcccgggta   5460
gccactgggc acgtctccta gatactggac tcatcggacg ctctcctcga gttgtccatc   5520
gagctctgta ccaagcaccg catcgcaatc cactcaacca gctccgccgc gagcaggagc   5580
gctccacgac acgcgacgcc caagctggca cgcacctcgc cgatggcccg ataagcacgg   5640
ccgtgcgacg tggcggcccg cctcccctct ggcacgcagc tcccctccac gtagccgcgc   5700
cagggcgcca cgtacagcgg cgcgcgcgct acaaatacgg tgccccgagc tccattcccc   5760
agcaccagca gagtcacaca cactgagcga gctaaaccat caggaagtga tggagcatca   5820
gggcggctat acgccatttg aagccgatgt cacgccgtat gttattgccg ggaaaagtgt   5880
acgtatcacc gtttgtgccg gaatccatcg cagcgtaatg ctctacacca cgccgaacac   5940
ctgggtggac gatatcaccg tggtgacgca tgtcgcgcaa gactgtaacc acgcgtctgt   6000
tgactggcag gtggtggcca atggtgatgt cagcgttgaa ctgcgtgatg cggatcaaca   6060
ggtggttgca actggacaag gcactagcgg gactttgcaa gtggtgaatc cgcacctctg   6120
gcaaccgggt gaaggttatc tctatgaact gtgcgtcaca gccaaaagcc agacagagtg   6180
```

-continued

```
tgatatctac ccgcttcgcg tcggcatccg gtcagtggca gtgaagggcg aacagttcct   6240
gattaaccac aaaccgttct actttactgg ctttggtcgt catgaagatg cggacttgcg   6300
tggcaaagga ttcgataacg tgctgttacc aatgcttaat cagtgaggca cctatctcag   6360
cgatctgtct atttcgttca tccatagttg cctgactccc cgtcgtgtag ataactacga   6420
tacgggaggg cttaccatct ggccccagtg ctgcaatgat accgcgagac ccacgctcac   6480
cggctccaga tttatcagca ataaaccagc cagccggaag ggccgagcgc agaagtggtc   6540
ctgcaacttt atccgcctcc atccagtcta ttaattgttg ccgggaagct agagtaagta   6600
gttcgccagt taatagtttg cgcaacgttg ttgccattgc tacaggcatc gtggtgtcac   6660
gctcgtcgtt tggtatggct tcattcagct ccggttccca acgatcaagg cgagttacat   6720
gatcccccat gttgtgcaaa aaagcggtta gctccttcgg tcctccgatc gttgtcagaa   6780
gtaagttggc cgcagtgtta tcactcatgg ttatggcagc actgcataat tctcttactg   6840
tcatgccatc cgtaagatgc ttttctgtga ctggtgagta ctcaaccaag tcattctgag   6900
aatagtgtat gcggcgaccg agttgctctt gcccggcgtc aatacgggat aataccgcgc   6960
cacatagcag aactttaaaa gtgctcatca ttggaaaacg ttcttcgggg cgaaaactct   7020
caaggatctt accgctgttg agatccagtt cgatgtaacc cactcgtgca cccaactgat   7080
cttcagcatc ttttactttc accagcgttt ctgggtgagc aaaaacagga aggcaaaatg   7140
ccgcaaaaaa gggaataagg gcgacacgga aatgttgaat actcatactc ttcctttttc   7200
aatattattg aagcatttat cagggttatt gtctcatgag cggatacata tttgaatgta   7260
tttagaaaaa taaacaaata ggggttccgc gcacatttcc ccgaaaagtg ccacctgacg   7320
tctaagaaac cattattatc atgacattaa cctataaaaa taggcgtatc acgaggccct   7380
ttcgtctcgc gcgtttcggt gatgacggtg aaaacctctg acacatgcag ctcccggaga   7440
cggtcacagc ttgtctgtaa gcggatgccg ggagcagaca agcccgtcag ggcgcgtcag   7500
cgggtgttgg cgggtgtcgg ggctggctta actatgcggc atcagagcag attgtactga   7560
gagtgcacca tatgcggtgt gaaataccgc acagatgcgt aaggagaaaa taccgcatca   7620
ggcgccattc gccattcagg ctgcgcaact gttgggaagg gcgatcggtg cgggcctctt   7680
cgctattacg ccagctggcg aaagggggat gtgctgcaag gcgattaagt tgggtaacgc   7740
cagggttttc ccagtcacga cgttgtaaaa cgacggccag tgcaagcttg catgcctgca   7800
gtgcagcgtg acccggtcgt gcccctctct agagataatg agcattgcat gtctaagtta   7860
taaaaaatta ccacatattt tttttgtcac acttgtttga agtgcagttt atctatcttt   7920
atacatatat ttaaacttta ctctacgaat aatataatct atagtactac aataatatca   7980
gtgttttaga gaatcatata aatgaacagt tagacatggt ctaaaggaca attgagtatt   8040
ttgacaacag gactctacag ttttatcttt ttagtgtgca tgtgttctcc tttttttttg   8100
caaatagctt cacctatata atacttcatc cattttatta gtacatccat ttagggttta   8160
gggttaatgg tttttataga ctaatttttt tagtacatct attttattct attttagcct   8220
ctaaattaag aaaactaaaa ctctatttta gtttttttat ttaataattt agatataaaa   8280
tagaataaaa taaagtgact aaaaattaaa caaataccct ttaagaaatt aaaaaaacta   8340
aggaaacatt tttcttgttt cgagtagata atgccagcct gttaaacgcc gtcgacgagt   8400
ctaacggaca ccaaccagcg aaccagcagc gtcgcgtcgg gccaagcgaa gcagacggca   8460
cggcatctct gtctgaatag aatacaaacc ctagaaaaac aaggcacatc tcggcgccgc   8520
caatagaagg cagaaaccct agccgtcatt tttcttgaag aatatagagc gacgtcgata   8580
```

-continued

```
ggaagatact taaatgttga atccaagcac ctagaataat gagttagatt agaagaaaac   8640
tatcaacttc gaaatcaaga agaaatgttt tattctgttg cataaaactt tcgcgtggag   8700
aagctctgtt cagagcccgg gtagccactg ggcacgtctc ctagatactg gactcatcgg   8760
acgctctcct cgagttgtcc atcgagctct gtaccaagca ccgcatcgca atccactcaa   8820
ccagctccgc cgcgagcagg agcgctccac gacacgcgac gcccaagctg gcacgcacct   8880
cgccgatggc ccgataagca cggccgtgcg acgtggcggc ccgcctcccc tctggcacgc   8940
agctcccctc cacgtagccg cgccagggcg ccacgtacag cggcgcgcgc gctacaaata   9000
cggtgccccg agctccattc cccagcacca gcagagtcac acacactgag cgagctaaac   9060
catggtatag ccgccctgat gctccatcac ttcctgatta ttgacccaca ctttgccgta   9120
atgagtgacc gcatcgaaac gcagcacgat acgctggcct gcccaacctt tcggtataaa   9180
gacttcgcgc tgataccaga cgttgcccgc ataattacga atatctgcat cggcgaactg   9240
atcgttaaaa ctgcctggca cagcaattgc ccggctttct tgtaacgcgc tttcccacca   9300
acgctgatca attccacagt tttcgcgatc cagactgaat gcccacaggc cgtcgagttt   9360
tttgatttca cgggttgggg tttctacagg acgctattaa ttgttgccgg gaagctagag   9420
taagtagttc gccagttaat agtttgcgca acgttgttgc cattgctaca ggcatcgtgg   9480
tgtcacgctc gtcgtttggt atggcttcat tcagctccgg ttcccaacga tcaaggcgag   9540
ttacatgatc ccccatgttg tgcaaaaaag cggttagctc cttcggtcct ccgatcgttg   9600
tcagaagtaa gttggccgca gtgttatcac tcatggttca ctgtcagacc aagtttactc   9660
atatatactt tagattgatt taaaacttca tttttaattt aaaaggatct aggtgaagat   9720
cctttttgat aatctcatga ccaaaatccc ttaacgtgag ttttcgttcc actgagcgtc   9780
agaccccgta gaaaagatca aaggatcttc ttgagatcct ttttttctgc gcgtaatctg   9840
ctgcttgcaa acaaaaaaac caccgctacc agcggtggtt tgtttgccgg atcaagagct   9900
accaactctt tttccgaagg taactggctt cagcagagcg cagataccaa atactgtcct   9960
tctagtgtag ccgtagttag gccaccactt caagaactct gtagcaccgc ctacatacct  10020
cgctctgcta atcctgttac cagtggctgc tgccagtggc gataagtcgt gtcttaccgg  10080
gttggactca agacgatagt taccggataa ggcgcagcgg tcgggctgaa cggggggttc  10140
gtgcacacag cccagcttgg agcgaacgac ctacaccgaa ctgagatacc tacagcgtga  10200
gctatgagaa agcgccacgc ttcccgaagg gagaaaggcg gacaggtatc cggtaagcgg  10260
cagggtcgga acaggagagc gcacgaggga gcttccaggg ggaaacgcct ggtatcttta  10320
tagtcctgtc gggtttcgcc acctctgact tgagcgtcga tttttgtgat gctcgtcagg  10380
ggggcggagc ctatggaaaa acgccagcaa cgcggccttt ttacggttcc tggccttttg  10440
ctggcctttt gctcacatgt tctttcctgc gttatcccct gattctgtgg ataaccgtat  10500
taccgccttt gagtgagctg ataccgctcg ccgcagccga acgaccgagc gcagcgagtc  10560
agtgagcgag gaagcggaag agcgcccaat acgcaaaccg cctctccccg cgcgttggcc  10620
gattcattaa tgcagctggc acgacaggtt tcccgactgg aaagcgggca gtgagcgcaa  10680
cgcaattaat gtgagttagc tcactcatta ggcaccccag gctttacact ttatgcttcc  10740
ggctcgtatg ttgtgtggaa ttgtgagcgg ataacaattt cacacaggaa acagctatga  10800
ccatgattac gaattccgat ctagtaacat agatgacacc gcgcgcgata atttatccta  10860
gtttgcgcgc tatattttgt tttctatcgc gtattaaatg tataattgcg ggactctaat  10920
```

```
cataaaaacc catctcataa ataacgtcat gcattacatg ttaattatta catgcttaac  10980
gtaattcaac agaaattata tgataatcat cgcaagaccg gcaacaggat tcaatcttaa  11040
gaaactttat tgccaaatgt ttgaacgatc tgcaggtcga cggatcagat ctcggtgacg  11100
ggcaggaccg gacggggcgg taccggcagg ctgaagtcca gctgccagaa acccacgtca  11160
tgccagttcc cgtgcttgaa gccggccgcc cgcagcatgc cgcggggggc atatccgagc  11220
gcctcgtgca tgcgcacgct cgggtcgttg ggcagcccga tgacagcgac cacgctcttg  11280
aagccctgtg cctccaggga cttcagcagg tgggtgtaga gcgtggagcc cagtcccgtc  11340
cgctggtggc ggggggagac gtacacggtc gactcggccg tccagtcgta ggcgttgcgt  11400
gccttccagg ggcccgcgta ggcgatgccg gcgacctcgc cgtccacctc ggcgacgagc  11460
cagggatagc gctcccgcag acggacgagg tcgtccgtcc actcctgcgg ttcctgcggc  11520
tcggtacgga agttgaccgt gcttgtctcg atgtagtggt tgacgatggt gcagaccgcc  11580
ggcatgtccg cctcggtggc acggcggatg tcggccgggc gtcgttctgg gctcatggat  11640
ccagctccgc cgcgagcagg agcgctccac gacacgcgac gcccaagctg gcacgcacct  11700
cgccgatggc ccgataaggc agagcgaggt atgtaggcgg tgctacagag ttcttgaagt  11760
ggtggcctaa ctacggctac actagaagga cagtatttgg tatctgcgct ctgctgaagc  11820
cagttacctt cggaaaaaga gttggtagct cttgatccgg caaacaaacc accgctggta  11880
gcggtggttt ttttgtttgc aagcagcaga ttacgcgcag aaaaaaagga tctcaagaag  11940
atcctttgat cttttctacg gggtctgacg ctcagtggaa cgaaaactca cgttaaggga  12000
ttttggtcat gagattatca aaaaggatct tcacctagat ccttttaaat taaaaatgaa  12060
gttttaaatc aatctaaagt atatatgagt aaacttggtc tgacagttac caatgcttaa  12120
tcagtgaggc acctatctca gcgatctgtc tatttcgttc atccatagtt gcctgactcc  12180
ccgtcgtgta gataactacg atacgggagg gcttaccatc tggccccagt gctgcaatga  12240
taccgcgaga cccacgctca ccggctccag atttatcagc aataaaccag ccagccggaa  12300
gggccgagcg cagaagtggt cctgcaactt tatccgcctc catccagtct attaattgtt  12360
gccgggaagc tagagtaagt agttcgccag ttaatagttt gcgcaacgtt gttgccattg  12420
ctacaggcat cgtggtgtca cgctcgtcgt ttggtatggc ttcattcagc tccggttccc  12480
aacgatcaag gcgagttaca tgatccccca tgttgtgcaa aaaagcggtt agctccttcg  12540
gtcctccgat cgttgtcaga agtaagttgg ccgcagtgtt atcactcatg gttatggcag  12600
cactgcataa ttctcttact gtcatgccat ccgtaagatg cttttctgtg actggtgagt  12660
actcaaccaa gtcattctga gaatagtgta tgcggcgacc gagttgctct tgcccggcgt  12720
caatacggga taataccgcg ccacatagca gaactttaaa agtgctcatc attggaaaac  12780
gttcttcggg gcgaaaactc tcaaggatct taccgctgtt gagatccagt tcgatgtaac  12840
ccactcgtgc acccaactga tcttcagcat cttttacttt caccagcgtt tctgggtgag  12900
caaaaacagg aaggcaaaat gccgcaaaaa agggaataag ggcgacacgg aaatgttgaa  12960
tactcatact cttccttttt caatattatt gaagcattta tcagggttat tgtctcatga  13020
gcggatacat atttgaatgt atttagaaaa ataaacaaat aggggttccg cgcacatttc  13080
cccgaaaagt gccacctgac gtctaagaaa ccattattat catgacatta acctataaaa  13140
ataggcgtat cacgaggccc tttcgtctcg cgcgtttcgg tgatgacggt gaaaacctct  13200
gacacatgca gctcccggag acggtcacag cttgtctgta agcggatgcc gggagcagac  13260
aagcccgtca gggcgcgtca gcgggtgttg gcgggtgtcg gggctggctt aactatgcgg  13320
```

```
catcagagca gattgtactg agagtgcacc atatgcggtg tgaaataccg cacagatgcg  13380
taaggagaaa ataccgcatc aggcgccatt cgccattcag gctgcgcaac tgttgggaag  13440
ggcgatcggt gcgggcctct tcgctattac gccagctggc gaaaggggga tgtgctgcaa  13500
ggcgattaag ttgggtaacg ccagggtttt cccagtcacg acgttgtaaa acgacggcca  13560
gtgcaagctt gcatgcctgc agtgcagcgt gacccggtcg tgcccctctc tagagataat  13620
gagcattgca tgtctaagtt ataaaaaatt accacatatt ttttttgtca cacttgtttg  13680
aagtgcagtt tatctatctt tatacatata tttaaacttt actctacgaa taatataatc  13740
tatagtacta caataatatc agtgttttag agaatcatat aaatgaacag ttagacatgg  13800
tctaaaggac aattgagtat tttgacaaca ggactctaca gttttatctt tttagtgtgc  13860
atgtgttctc cttttttttt gcaaatagct tcacctatat aatacttcat ccattttatt  13920
agtacatcca tttagggttt agggttaatg gtttttatag actaattttt ttagtacatc  13980
tattttattc tattttagcc tctaaattaa gaaaactaaa actctatttt agttttttta  14040
tttaataatt tagatataaa atagaataaa ataaagtgac taaaaattaa acaaataccc  14100
tttaagaaat taaaaaaact aaggaaacat ttttcttgtt tcgagtagat aatgccagcc  14160
tgttaaacgc cgtcgacgag tctaacggac accaaccagc gaaccagcag cgtcgcgtcg  14220
ggccaagcga agcagacggc acggcatctc tgtcgctgcc tctggacccc tctcgagagt  14280
tccgctccac cgttggactt gctccgctgt cggcatccag aaattgcgtg gcggagcggc  14340
agacgtgagc cggcacggca ggcggcctcc tcctcctctc acggcaccgg cagctacggg  14400
ggattccttt cccaccgctc cttcgctttc ccttcctcgc ccgccgtaat aaatagacac  14460
cccctccaca ccctctttcc ccaacctcgt gttgttcgga gcgcacacac acacaaccag  14520
atctccccca aatccacccg tcggcgtacg ccgctcgtcc tccccccccc cccctctcta  14580
ccttctctag atcggcgttc cggtccatgg ttagggcccg gtagttctac ttctgttcat  14640
gtttgtgtta gatccgtgtt tgtgttagat ccgtgctgct agcgttcgta cacggatgcg  14700
acctgtacgt cagacacgtt ctgattgcta acttgccagt gtttctcttt ggggaatcct  14760
gggatggctc tagccgttcc gcagacggga tcgatttcat gatttttttt gtttcgttgc  14820
atagggtttg gtttgccctt ttcctttatt tcaatatatg ccgtgcactt gtttgtcggg  14880
tcatcttttc atgctttttt ttgtcttggt tgtgatgatg tggtctggtt gggcggtcgt  14940
tctagatcgg agtagaattc cccgatctag taacatagat gacaccgcgc gcgataattt  15000
atcctagttt gcgcgctata ttttgttttc tatcgcgtat taaatgtata attgcgggac  15060
tctaatcata aaaacccatc tcataaataa cgtcatgcat tacatgttaa ttattacatg  15120
cttaacgtaa ttcaacagaa attatatgat aatcatcgca agaccggcaa caggattcaa  15180
tcttaagaaa ctttattgcc aaatgtttga acgatcgggg aaattcgagc tcttagaact  15240
cccaccactt ttggaactcc caccactttt gaaggtctgg cagttgttct tcaatctcca  15300
acaaactgtt tccttcttca aggtacgcaa aaccgtcgca aaacggaaca ttcatttctt  15360
gaccaaacat aacgtccgga gagttcgtaa accgatcatc cgattcttca ccgctgccac  15420
tactactagt tttctcttga tgcttttcgg ctacatttct cagcacctcc aattgattga  15480
gtagggcctg attctctttc tttagagact cggatttaga cgcaagcgtc tcgtagttat  15540
gctttagcgc gttatactct tgctcaatct gcctcgactt tgatcgcgcg cgtttgttct  15600
ggaaccatat cgccacttga cgaggatgaa gcccgagttt atgtgccaac tggtgtttca  15660
```

-continued

```
tccttaactc gggtctcgac tgtgtctcaa acatgtactc taggaaactt atttgtttgt  15720
cggtaaatcg tctccgcccc tcgtttcggt tcttcctggt ggttgttact tgttgaagag  15780
acatggatcc gagtcgacct gcagaagtaa caccaaacaa cagggtgaca ctcgacaaaa  15840
gaaacagtac caagcaaata aatagcgtat gaaggcaggg ctaaaaaaat ccacatatag  15900
ctgctgcata tgccatcatc caagtatatc aagatcaaaa taattataaa acatacttgt  15960
ttattataat agataggtac tcaaggttag agcatatgaa tagatgctgc atatgccatc  16020
atgtatatgc atcagtaaaa cccacatcaa catgtatacc tatcctagat cgatatttcc  16080
atccatctta aactcgtaac tatgaacgct gtcttgacac acacatacag ttccaaaatt  16140
aataaataca ccaggtagtt tgaaacagta ttctactccg atctagaacg aatgaacgac  16200
cgcccaacca caccacatca tcacaaccaa gcgaacaaaa agcatctctg tatatgcatc  16260
agtaaaaccc gcatcaacat gtatacctat cctagatcga tatttccatc catcatcttc  16320
aattcgtaac tatgaatatg tatggcacac acatacagat ccaaaattaa taaatccacc  16380
aggtagtttg aaacagaatt cgtaatcatg gtcatagctg tttcctgtgt gaaattgtta  16440
tccgctcaca attccacaca acatacgagc cggaagcata aagtgtaaag cctggggtgc  16500
ctaatgagtg agctaactca cattaattgc gttgcgctca ctgcccgctt tccagtcggg  16560
aaacctgtcg tgccagctgc attaatgaat cggccaacgc gcggggagag gcggtttgcg  16620
tattgggcgc tcttccgctt cctcgctcac tgactcgctg cgctcggtcg ttcggctgcg  16680
gcgagcggta tcagctcact caaaggcggt aatacggtta tccacagaat caggggataa  16740
cgcaggaaag aacatgtgag caaaaggcca gcaaaaggcc aggaaccgta aaaaggccgc  16800
gttgctggcg tttttccata ggctccgccc ccctgacgag catcacaaaa atcgacgctc  16860
aagtcagagg tggcgaaacc cgacaggact ataaagatac caggcgtttc cccctggaag  16920
ctccctcgtg cgctctcctg ttccgaccct gccgcttacc ggatacctgt ccgcctttct  16980
cccttcggga agcgtggcgc tttctcatag ctcacgctgt aggtatctca gttcggtgta  17040
ggtcgttcgc tccaagctgg gctgtgtgca cgaacccccc gttcagcccg accgctgcgc  17100
cttatccggt aactatcgtc ttgagtccaa cccggtaaga cacgacttat cgccactggc  17160
agcagccact ggtaacagga ttagcagagc gaggtatgta ggcggtgcta cagagttctt  17220
gaagtggtgg cctaactacg gctacactag aaggacagta tttggtatct gcgctctgct  17280
gaagccagtt accttcggaa aaagagttgg tagctcttga tccggcaaac aaaccaccgc  17340
tggtagcggt ggtttttttg tttgcaagca gcagattacg cgcagaaaaa aaggatctca  17400
agaagatcct ttgatctttt ctacggggtc tgacgctcag tggaacgaaa actttctac   17460
ggggtctgac gctcagtgga acgaaaactc acgttaaggg attttggtca tgagattatc  17520
aaaaaggatc ttcacctaga tccttttaaa ttaaaaatga agttttaaat caatctaaag  17580
tatatatgag taaacttggt ctgacagttt gaggcaccta tctcagcgat ctgtctattt  17640
cgttcatcca tagttgcctg actccccgtc gtgtagataa ctacgatacg ggagggctta  17700
ccatctggcc ccagtgctgc aatgataccg cgagacccac gctcaccggc tccagattta  17760
tcagcaataa accagccagc cggaagggcc gagcgcagaa gtggtcctgc aactttatcc  17820
gcctccatcc agtctattaa ttgttgccgg gaagctagag taagtagttc gccagttaat  17880
agtttgcgca acgttgttgc cattgctaca ggcatcgtgg tgtcacgctc gtcgtttggt  17940
atggcttcat tcagctccgg ttcccaacga tcaaggcgag ttacatgatc ccccatgttg  18000
tgcaaaaaag cggttagctc cttcggtcct ccgatcgttg tcagaagtaa gttggccgca  18060
```

gtgttatcac tcatggttat ggcagcactg cataattctc ttactgtcat gccatccgta 18120
agatgctttt ctgtgactgg tgagtactca accaagtcat tctgagaata gtgtatgcgg 18180
cgaccgagtt gctcttgccc ggcgtcaata cgggataata ccgcgccaca tagcagaact 18240
ttaaaagtgc tcatcattgg aaaacgttct tcggggcgaa aactctcaag gatcttaccg 18300
ctgttgagat ccagttcgat gtaacccact cgtgcaccca actgatcttc agcatctttt 18360
actttcacca gcgtttctgg gtgagcaaaa acaggaaggc aaaatgccgc aaaaaaggga 18420
ataagggcga cacggaaatg ttgaatactc atactcttcc tttttcaata ttattgaagc 18480
atttatcagg gttattgtct catgagcgga tacatatttg aatgtattta gaaaaataaa 18540
tgtatttaga aaaataaaca aataggggtt ccgcgcacat ttccccgaaa agtgccacct 18600
gacgtctaag aaaccattat tatcatgaca ttaacctata aaaataggcg tatcacgagg 18660
ccctttcgtc tcgcgcgttt cggtgatgac ggtgaaaacc tctgacacat gcagctcccg 18720
gagacggtca cagcttgtct gtaagcggat gccgggagca gacaagcccg tcagggcgcg 18780
tcagcgggtg ttggcgggtg tcggggctgg cttaactatg cggcatcaga gcagattgta 18840
ctgagagtgc accatatgcg gtgtgaaata ccgcacagat gcgtaaggag aaaataccgc 18900
atcaggcgcc attcgccatt caggctgcgc aactgttggg aagggcgatc ggtgcgggcc 18960
tcttcgctat tacgccagct ggcgaaaggg ggatgtgctg caaggcgatt aagttgggta 19020
acgccagggt tttcccagtc acgacgttgt aaaacgacgg ccagtgccaa gcttgcatgc 19080
ctgcagtgca gcgtgacccg gtcgtgcccc tctctagaga taatgagcat tgcatgtcta 19140
agttataaaa aattaccaca tatttttttt gtcacacttg tttgaagtgc agtttatcta 19200
tctttataca tatatttaaa ctttactcta cgaataatat aatctatagt actacaataa 19260
tatcagtgtt ttagagaatc atataaatga acagttagac atggtctaaa ggacaattga 19320
gtattttgac aacaggactc tacagtttta tctttttagt gtgcatgtgt tctccttttt 19380
ttttgcaaat agcttcacct atataatact tcatccattt tattagtaca tccatttagg 19440
gtttagggtt aatggttttt atagactaat ttttttagta catctatttt attctatttt 19500
agcctctaaa ttaagaaaac taaaactcta ttttagtttt tttatttaat aatttagata 19560
taaaatagaa taaaataaag tgactaaaaa ttaaacaaat accctttaag aaattaaaaa 19620
aactaaggaa acatttttct tgtttcgagt agataatgcc agcctgttaa acgccgtcga 19680
cgagtctaac ggacaccaac cagcgaacca gcagcgtcgc gtcgggccaa gcgaagcaga 19740
cggcacggca tctctgtcgc tgcctctgga cccctctcga gagttccgct ccaccgttgg 19800
acttgctccc tttattttat tctattttat atctaaatta ttaaataaaa aaactaaaat 19860
agagttttag ttttcttaat ttagaggcta gtcccgaaca gtgtcctgga ggccgcacac 19920
gcttcggccc cgaccctcga ttcggagccc gctgcgttcg ttgaggaaga acgattggac 19980
gtcacctcag aggctgcgac attaaaggcg gtcgagtcga acgccgaccc cgcactccgc 20040
gctgcccatt actccgagga gccggattct tctccggcct ccgggccttc catgcccctg 20100
ccgaccgaat ccgattgggc acctgtaatg gagttcaccg ccgcggacat ctttcagtgt 20160
tcacctttca gtgacatcct gaattatctc aagtctctct ctttatcagg agagcccagg 20220
ccggattatg gtctgcgagg ttgggattcg gacgatgaag aaattcaaag cccacccacc 20280
acccacttaa tagccactgt cgacgattta accgacatgc tcgacttcgg ctccgaagac 20340
ttcgacggta tggacgacga aggaggagac gaaccggaac cagcacccac agggcactgg 20400
atatccacca cacacaat 20418

<210> SEQ ID NO 7
<211> LENGTH: 300
<212> TYPE: DNA
<213> ORGANISM: Artificial Sequence
<220> FEATURE:
<223> OTHER INFORMATION: 5? flanking region (long insert)

<400> SEQUENCE: 7
taatggtgag tgtatgcgct tgcgtctgta ttgtgtttaa aaaactcatt ctaagaaact 60
cgtcatacag tgtccaccgt caaggagcca tctagtaggg tgtggatggg catgtgacag 120
gaaccttgtc gtgtgcacgt tgtatgtcgg tcttgttcaa tatgtcgtct gtttcctcgg 180
cttacatgct cttttacgtg tcgtgcaccc aactgatctt cagcatcttt tactttcacc 240
agcgtttctg ggtgagcaaa aacaggaagg caaaatgccg caaaaaaggg aataagggcg 300

<210> SEQ ID NO 8
<211> LENGTH: 385
<212> TYPE: DNA
<213> ORGANISM: Artificial Sequence
<220> FEATURE:
<223> OTHER INFORMATION: 3? flanking region (long insert)

<400> SEQUENCE: 8
tattacgcca gctggcgaaa gggggatgtg ctgcaaggcg attaagttgg gtaacgccag 60
ggttttccca gtcacgacgt tgtaaaacga cggccagtgc gtcgactcta gaggtccctc 120
gaccatggct gtaaggtcgc cgaatacaag ggcatgggtg gcgaggccta agaggagtat 180
aatttcttag acatttgtca attataaact tcttggtaaa agagcatgta agccgaggaa 240
acagacgaca tattgaacaa gaccgacata caacgtgcac acgacaaggt tcctgtcaca 300
tgcccatcca caccctacta gatggctcct tgacggtgga cactgtatga cgagtttctt 360
agaatgagtt ttttaaacac aatac 385

<210> SEQ ID NO 9
<211> LENGTH: 392
<212> TYPE: DNA
<213> ORGANISM: Artificial Sequence
<220> FEATURE:
<223> OTHER INFORMATION: 5? flanking region (short insert)

<400> SEQUENCE: 9
gagcgcgctt tcctatttag gatccaaatt ggcactgata ctaaactgct tagacgaatc 60
gcctggagta aaatcaacaa gctcggtttc agcagccgac ttaaacttca tcgccgggtc 120
atgctcggtg gttggcttct ttagagacgt catatccgcc aggtcaacat tattttgata 180
aaaattcatc tcctctgccg cacaaacaga ctcagcataa gccgcatcgc cttcttcaca 240
ttctagggct acctttcgac tcccattgag ggagtcccgg attagggggt gtttggaaca 300
ccacgatgcc tgtagcaatg gcaacaacgt tgcgcaaact attaactggc gaactactta 360
ctctagcttc ccggtaacaa ttaatagact gg 392

<210> SEQ ID NO 10
<211> LENGTH: 628
<212> TYPE: DNA
<213> ORGANISM: Artificial Sequence
<220> FEATURE:
<223> OTHER INFORMATION: 3? flanking region (short insert)

<400> SEQUENCE: 10
ccaccgttgg acttgctccc tttattttat tctattttat atctaaatta ttaaataaaa 60
aaactaaaat agagttttag ttttcttaat ttagaggcta gtcccgaaca gtgtcctgga 120
ggccgcacac gcttcggccc cgaccctcga ttcggagccc gctgcgttcg ttgaggaaga 180
acgattggac gtcacctcag aggctgcgac attaaaggcg gtcgagtcga acgccgaccc 240
cgcactccgc gctgcccatt actccgagga gccggattct tctccggcct ccgggccttc 300 catgccccctg ccgaccgaat ccgattgggc acctgtaatg gagttcaccg ccgcggacat 360
ctttcagtgt tcacctttca gtgacatcct gaattatctc aagtctctct ctttatcagg 420
agagcccagg ccggattatg gtctgcgagg ttgggattcg gacgatgaag aaattcaaag 480
cccacccacc acccacttaa tagccactgt cgacgattta accgacatgc tcgacttcgg 540
ctccgaagac ttcgacggta tggacgacga aggaggagac gaaccggaac cagcacccac 600
agggcactgg atatccacca cacacaat 628

<210> SEQ ID NO 11
<211> LENGTH: 23
<212> TYPE: DNA
<213> ORGANISM: Artificial Sequence
<220> FEATURE:
<223> OTHER INFORMATION: HB4 Forward primer

<400> SEQUENCE: 11
gggcttcatc ctggtcaagt ggc 23

<210> SEQ ID NO 12
<211> LENGTH: 30
<212> TYPE: DNA
<213> ORGANISM: Artificial Sequence
<220> FEATURE:
<223> OTHER INFORMATION: HB4 Reverse primer

<400> SEQUENCE: 12
tcttgatgct tttctgctac atttctcagc 30

<210> SEQ ID NO 13
<211> LENGTH: 26
<212> TYPE: DNA
<213> ORGANISM: Artificial Sequence
<220> FEATURE:
<223> OTHER INFORMATION: Bar Forward primer

<400> SEQUENCE: 13
cacgcaacgc ctacgactgg acggcc 26

<210> SEQ ID NO 14
<211> LENGTH: 24
<212> TYPE: DNA
<213> ORGANISM: Artificial Sequence
<220> FEATURE:
<223> OTHER INFORMATION: Bar Reverse primer

<400> SEQUENCE: 14
gtaccggcag gctgaagtcc agct 24

WHEAT TRANSGENIC EVENT IND-ØØ412-7

FIELD OF THE INVENTION

The invention relates to the fields of plant production, plant breeding and agriculture. More specifically, it relates to wheat transgenic event IND-ØØ412-7, nucleotide sequences, plants, parts of plants, seeds, cells, agricultural products, and detection and production methods related to wheat transgenic event IND-ØØ412-7.

BACKGROUND OF THE INVENTION

Improving crop yields and their characteristics has become essential to satisfy food demand. Due to biotechnological developments combined with agriculture, new crops have been developed with the capacity to adapt to diverse environmental and/or ecological conditions.

While grown, plants are exposed to a variety of abiotic stresses: drought, salinity, low and high temperatures, excessive radiation, low nutrient availability, soil compaction that prevents root development, etc. (Duque et al., 2013; Sayed, 2003). All of them can affect at some point plant growth and development, as well as yield. It is reasonable to suppose that any of these environmental factors may occur during crop life cycles in the field. When this is the case, complex response mechanisms are triggered, which will be later on reflected in the measurements performed, as they result from the integration of such stress effects.

One of the most commonly used techniques to mitigate environmental negative effects on crops is based on transgenic events, i.e., the insertion of genes of interest in the genome of a target crop. However, production and selection of a commercially suitable transgenic event requires extensive investigation, analysis and characterization of a large number of individual transformation events. This makes it possible to select an event containing the desired trait, able to develop the phenotypic and agricultural characteristics required for such event to be suitable for commercial purposes, with no negative effect on other crop features.

This process requires the generation of transgenic events that will be molecularly and phenotypically characterized in order to identify and select the event expressing the heterologous gene of interest considering the desired phenotype to be obtained.

Event selection implies stages of laboratory development as well as tests carried out under controlled conditions either in the field and/or in greenhouses. It is necessary to analyze the response to events along the years, in multiple locations and under a variety of environmental conditions in order to select the event that meets the required phenotypic and genetic characteristics as well as the commercial features required.

The present invention features this type of commercially suitable event, which enables new advantageous traits in wheat.

There is a wide variety of genes that may be used to generate commercially suitable events. A gene whose expression is of special interest is the one that encodes transcription factor HAHB4.

HAHB4 (which stands for *Helianthus Annuus* Homeobox-4) is a sunflower transcription factor that belongs to the HD-Zip family. The HaHB4 gene expression is regulated at transcriptional level by external environmental factors, such as water availability and soil salinity, as well as the phytohormones related to these factors, abscisic acid and ethylene.

Patent AR81216B2 discloses gene HaHB4, inducible by water deficit and abscisic acid and encoding a sunflower transcription factor type HD-Zip. This patent also discloses gene isolation and characterization, and its introduction in the model plant *Arabidopsis thaliana*. However, it reports neither transgenic plants of commercial interest carrying the event of the present invention nor their advantageous properties regarding concomitant abiotic stresses that occur in agriculture conditions.

In patent AR81216B2 no mention is made either concerning the particular selection of an event expressing gene HaHB4 in order to preserve the main trait of interest, i.e., drought tolerance, with no impact on other agricultural features.

Furthermore, application AR090110A1 discloses modified gene HaHB4, particularly HaHB4.2, inducible by water deficit and abscisic acid and encoding a modified sunflower transcription factor type HD-Zip, particularly mod1HaHB4. This publication discloses generation and characterization of modified HaHB4.2 expression constructs and their introduction in model plant *Arabidopsis thaliana*. In broad terms, this publication also discloses generation and selection of soybean, wheat and corn transgenic events containing gene HaHB4.2.

DETAILED DESCRIPTION OF THE INVENTION

The present invention provides wheat plants resistant to abiotic stress containing event IND-ØØ412-7. These plants present advantages for their growth in unfavorable environmental conditions, thus allowing a higher yield.

More specifically, the present invention refers to the wheat event named IND-ØØ412-7, which has a representative seed registered in the American Type Culture Collection (ATCC) under access number PTA-126141 together with its progeny.

The present invention also includes wheat plants comprising event IND-ØØ412-7 represented by sequences SEQ ID No.: 1 and SEQ ID No.: 2.

The transgenic insert present in the event of the invention and in the seed registered comprises the selectable bar marker-gene and the gene HaHB4, which provides tolerance to abiotic stress. The bar gene derived from *Streptomyces hygroscopicus*, encodes PAT (Phosphinothricin Acetyl Transferase) protein. Gene HaHB4 derives from the sunflower plant, sp. *Helianthus annuus*, and encodes for a protein type HD-Zip I, which has a protein domain of homeodomain-type associated to a leucine zipper that provides abiotic stress-tolerance, mainly to drought. Regulation of genes of interest may be directed by different promoter sequences with different expression levels, sensitivity and tissue specificity. Experts in this field know that any promoter or nucleic acid terminator that directs or regulates the expression of a gene of interest may be used with no impact on the essence of the invention. Particularly, the event developed in the present invention contains the corn ubiquitin 1 gene promoter (prUBI-1) and the Tnos terminator for the bar gene that gives resistance to glufosinate ammonium herbicide. Furthermore, the event comprises once again the corn ubiquitin 1 gene promoter (prUBI-1) and the Tnos terminator to regulate the expression of the HaHB4 encoding region (FIG. 1 and FIG. 2).

Other aspects of the invention comprise the progeny of wheat plants, seeds and/or renewable parts of plants, seeds and progeny comprising wheat event IND-ØØ412-7, as well as food products for human or animal consumption derived from them. The invention also includes parts of plants comprising event IND-ØØ412-7, including, without limitation, pollen, ovules, flowers, shoots, roots, leaves, cell vegetative nuclei and other plant cells comprising event IND-ØØ412-7. The invention also refers to wheat plants comprising wheat event IND-ØØ412-7 featuring tolerance to multiple abiotic stresses, such as drought, salinity, low and high temperatures, radiation excess, low nutrient availability, soil compaction, etc., and different combinations of these factors.

The present invention partially refers to the cultivation of plants tolerant to abiotic stresses. In addition, it includes a novel event of wheat plant transformation comprising polynucleotides, as described herein, which are inserted in specific sites within the wheat genome, providing specific genetic and phenotypic features.

In some embodiments, this event/polynucleotide may be "stacked" with other traits including, for example, agronomic traits, and herbicide and/or insect tolerance. However, the present invention includes plants containing the individual event, as described herein.

Additional traits may be stacked within the plant genome or in the same locus as event IND-ØØ412-7, for example, by means of plant crossing, retransformation of the transgenic plant containing event IND-ØØ412-7 or addition of new traits through integration directed by homologous recombination.

In an embodiment, the present invention includes two wheat chromosomal sites located in chromosome 2. In some embodiments, the directed sites comprise heterologous nucleic acids. Wheat chromosomal sites are located between flanking sequences defined in FIG. 3 (SEQ ID Nos: 7, 8, 9 and 10).

In an embodiment, the present invention includes a method for producing wheat transgenic plants, comprising the insertion of a heterologous nucleic acid in one or several specific positions within chromosome 2.

In particular, the method comprises transforming a cell or cell culture with DNA sequences described in SEQ ID No.: 1 and SEQ ID No.: 2 and regenerate the cell in a stable way to originate a new whole plant.

Transformation of this plant cell may be performed through diverse techniques, whether physical, viral or chemical, including, among others, bio-ballistics, electroporation, bacterial transformation, or a combination of these techniques. All of them are well known by the expert in the field.

In particular, this invention uses a gene gun to boost DNA plasmid molecules with the sequences of interest (FIG. 2), more precisely, bombarded with plasmids pIND4-HB4 and pIND4-BAR (FIG. 1 and FIG. 2; SEQ ID No: 3 and SEQ ID No: 4).

Furthermore, the present invention provides tests for detecting the presence of this event in a wheat sample. The tests can be based on the DNA sequence of the recombinant constructs inserted within the wheat genome and on the genomic sequences flanking the insertion site. Kits and conditions useful to carry out the tests are also provided.

Therefore, the present invention partially refers to the cloning and analysis of DNA sequences belonging to all the inserts or to part of them and to the flanking regions (in transgenic wheat lines). These sequences are unique. Event-specific primers may be generated based on these inserts and on the flanking (and union) sequences. The PCR technique proved that these events can be identified through the analysis of amplicons generated by these sets of event-specific primers. Therefore, these and other related procedures may be used to identify wheat lines comprising the present invention event in an unequivocal manner.

The present invention also refers to PCR assay tests. These tests include, among others, quantitative real time (qPCR) or end-point PCR, to detect IND-ØØ412-7 event, amplicons and fragments thereof.

The invention also presents DNA molecules comprising a sufficient portion of the contiguous nucleotide sequence of SEQ ID No.: 5 and SEQ ID No.: 6 for it to operate as a DNA probe hybridizing under stringent conditions to DNA molecules comprising a nucleotide sequence selected from the group consisting of SEQ ID No.: 5 and SEQ ID No.: 6, and not hybridizing under stringent conditions to a DNA molecule not comprising a nucleotide sequence selected from the group consisting of SEQ ID No.: 5 and SEQ ID No.: 6.

In some instances, the probes used may be labeled with molecules that send out a detectable signal. An example of such molecules are fluorochromes. That is, oligonucleotides presenting fluorochromes at both ends and having a sequence complementary to part of the DNA fragment to be amplified. Among others, FAM, TET, HEX, JOE, CAL Fluor®, Quasar®, and Pulsar® dyes.

The invention also discloses a pair of DNA molecules consisting of a first DNA molecule and a second DNA molecule different from the first one, in which each of the first and second DNA molecules comprise a sufficient portion of contiguous nucleotides of SEQ ID No.: 5 and SEQ ID No.: 6 to operate as DNA probes if used together in an amplification reaction with DNA derived from event IND-ØØ412-7 to produce a diagnostic DNA amplicon for wheat transgenic event IND-ØØ412-7 in a sample.

The invention also describes a method for detecting the presence of DNA obtained from event IND-ØØ412-7 in a sample. The method comprises the comparison of the sample with the DNA molecules used as probe and primers, subjecting them to the same stringent hybridization conditions, and then detecting hybridization of the DNA probe to DNA in the amplified sample with the use of specific primers. This hybridization indicates the presence of DNA derived from the wheat transgenic event IND-ØØ412-7 in this sample.

The invention further presents a method for detecting the presence of a DNA molecule obtained from wheat transgenic event IND-ØØ412-7 in a sample, comparing the DNA preparation derived from this sample with a pair of oligonucleotides used as primers to produce an amplification reaction sufficient to produce a DNA amplicon comprising a sequence selected from the group that consists of SEQ ID No.: 5 and SEQ ID No.: 6, in order to detect the presence of the DNA amplicon in the reaction, where the presence of the DNA amplicon indicates the presence of a DNA molecule derived from IND-ØØ412-7 in the sample.

In addition, the invention presents a DNA detection kit comprising at least one DNA molecule with sufficient number of contiguous nucleotides of SEQ ID No.: 5 and SEQ ID No.: 6 for it to operate as a primer or specific DNA probe to detect the presence of DNA derived from wheat transgenic event IND-ØØ412-7, where DNA detection proves the presence of this event in a sample.

The invention also features a wheat plant, seed, cell, or a part of this plant comprising a nucleic acid molecule selected from the group consisting of SEQ ID No.: 5 and SEQ ID No.: 6. The invention further presents a wheat plant, seed, cell, or part of a plant tolerant to abiotic stresses. In addition, the invention features a wheat plant, seed, cell or part of a plant, whose genome produces an amplicon comprising a DNA molecule selected from the group consisting of SEQ ID No.: 5 and SEQ ID No.: 6 when tested with a DNA amplification method.

The invention further presents a wheat plant or seed, where the wheat plant or seed is generated from wheat transgenic event IND-ØØ412-7, or is a hybrid or heterozygous having at least one parent derived from wheat transgenic event IND-ØØ412-7.

The invention further presents a non-living plant material comprising a recombinant DNA molecule selected from the group consisting of SEQ ID No.: 5 and SEQ ID No.: 6.

In addition, the invention presents a commodity product resulting from wheat transgenic event IND-ØØ412-7 that comprises a nucleic acid molecule selected from the group consisting of SEQ ID No.: 5 and SEQ ID No.: 6, where detection of a nucleotide sequence in a sample derived from the commodity product defines that the commodity product derives from wheat transgenic event IND-ØØ412.7. The invention further presents a commodity product selected from the group consisting of whole or processed seeds, meal, flour, flakes, bioethanol, biogas, or other biomaterials, among others. The invention also features a method for producing a commodity product by obtaining a wheat plant or a part of it comprising wheat transgenic event IND-ØØ412-7 and for producing a wheat commodity product from the wheat plant or a part of it.

The invention presents a method for producing a wheat plant tolerant to abiotic stresses by crossing a plant with wheat transgenic event IND-ØØ412-7 comprising a nucleic acid molecule selected from the group consisting of SEQ ID No.: 5 and SEQ ID No.: 6 with a second wheat plant, in order to produce seeds, collect the seeds resulting from the cross, grow the seeds to produce multiple progeny plants, and select a progeny plant tolerant to abiotic stresses.

BRIEF DESCRIPTION OF THE DRAWINGS

FIG. 1: Schemes of plasmids pIND4-HB4 and pIND-Bar used in IND-ØØ412-7 obtaining. In the schemes are shown the CDSs of HaHB4 (left) and bar (right) with their regulatory elements and plasmid backbones. prUbi-1: maize Ubi-1 gene promoter region. prUbi-1 Exon: maize Ubi-1 gene first exon. prUbi-1 Intron: maize Ubi-1 gene first intron. HaHB4: CDS of HaHB4. Bar: CDS of bar. Tnos: terminator sequence of nos gene. pBR322 origin: ColE1 replication origin. bla: bla gene.

FIG. 2: Plasmid Sequences and Sequences of Interest.

FIG. 3: Resulting junction point sequences (JPs) supported by illumina and PacBio reads, and by PCR amplification products sequenced by Sanger. From the JPs, full obtained Wheat sequences are shown while only first 100 bp for the plasmid. Numbers represent absolute position on the Insert sequences.

FIG. 5: Southern blots of IND-ØØ412-7 plant DNA digested with HindIII, BamHI and AseI. Blots were hybridized with DIG-labeled probes for HaHB4 detection. DNA bands in IND-ØØ412-7 digests hybridizing to probes are pointed with white arrows. HB4 Soybean transgenic plant (IND-ØØ41Ø-5) was used as positive and hybridizing band is pointed with red arrow. DIG-labeled Marker VII and III ladder band sizes are indicated on the left and right, respectively, of the blots in kb.

FIG. 6: Southern blots of IND-ØØ412-7 plant DNA digested with HindIII, BamHI and AseI. Blots were hybridized with DIG-labeled probes for bar detection. DNA bands in IND-ØØ412-7 digests hybridizing to probes are pointed with white arrows. HB4 Soybean transgenic plant (IND-ØØ41Ø-5) was used as positive and hybridizing band is pointed with red arrow. DIG-labeled Marker VII and III ladder band sizes are indicated on the left and right, respectively, of the blots in kb.

FIG. 9: Quality scores of PacBio reads. The upper graph represents the quality scores of base calls as a function of the read position in percentage and the lower graph as a function of the read position in bp.

BRIEF DESCRIPTION OF THE SEQUENCES

Figure 4:
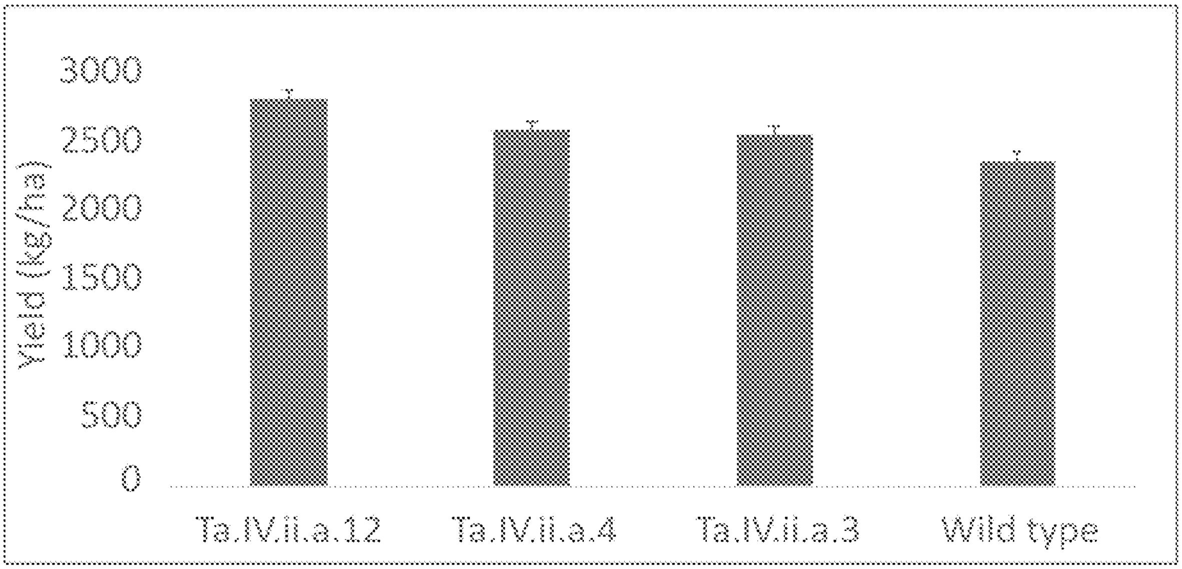
FIG. 4: Yield of transgenic lines (events) and the parental control (wild type) at six field trials conducted through 2009 to 2011. Thin bars represent the standard error of the mean (SEM).

SEQ ID No. 1: Long insert without flanking regions
SEQ ID No. 2: Short insert without flanking regions
SEQ ID No. 3: pIND4+HB4
SEQ ID No. 4: pIND4+BAR
SEQ ID No. 5: Long insert with flanking regions
SEQ ID No. 6: Short insert with flanking regions
SEQ ID No. 7: 5' flanking region (long insert)
SEQ ID No. 8: 3' flanking region (long insert)
SEQ ID No. 9: 5' flanking region (short insert)
SEQ ID No. 10: 3' flanking region (short insert)
SEQ ID No. 11: HB4 forward primer
SEQ ID No. 12: HB4 reverse primer
SEQ ID No. 13: Bar forward primer
SEQ ID No. 14: Bar reverse primer

DETAILED DESCRIPTION

The following definitions and methods are presented to better define the invention and to guide those trained in this technique to put it in practice. Unless otherwise stated, the terms used here are to be construed with the same meaning conventionally given to them by those trained in the relevant technique.

EXAMPLES

Example 1: Construction of Plasmids pIND4-HB4 and pIND4-Bar

The vectors used to obtain wheat IND-ØØ412-7 are based on a series of plasmids that use the corn ubiquitin promoter to direct the expression of genes in plants (Christensen and Quail, 1996). This promoter has proved to be very efficient in monocotyledons (Christensen et al., 1992). These plasmids use vector base pUC8 to perform the cloning and have been generated as a result of cloning the Pst1 fragment of the Ubi-1 corn ubiquitin gene of 1992pb. This fragment is the functional promoter and consists of: 899pb of the sequence of gene Ubi-1, a sequence of 83pb of the 5'-untranslated region from the first exon and the sequence of 1010pb of the first intron, ending in the reconstruction of the Pst1 site. The original intron, present in the 5'-untranslated region of gene Ubi-1 was retained in all these vectors since previous studies revealed that introns stimulate the expression of transgenes in cereal plants (Vasil et al., 1993).

Two plasmids based on this series, pIND4-HB4 y el pIND4-Bar, have been used in the genetic modification present in IND-ØØ412-7.

pIND4-HB4 (SEQ ID NO:3)

This plasmid has a polycloning site from which site BamHI was used to clone the encoding region of gene HaHB4. This restriction site is located after the sequences of the corn Ubi-1 gene promoter, the first exon and the first intron of the gene. This construct prUbi-1/Ubi1-Exon/Ubi-1Intron/HaHB4 was designed to obtain the constitutive expression of HAHB4. After the polycloning site and after the CDS of HaHB4, this vector has a sequence of the nopaline-synthase gene terminator of *A. tumefaciens* which includes the polyadenylation signal.

pIND4-Bar (SEQ ID NO: 4)

This plasmid has also been constructed by binding Ubi-1 regulatory regions to the encoding region of the bar gene of *S. hygroscopicus* in the BamHI site. This construct, prUbi-1/Ubi1-Exon/Ubi-1Intron/bar, allows selection of the transgenic plants expressing PAT and tolerate glufosinate ammonium herbicides, which become inactive due to this enzyme (Thompson et al., 1987). After the bar encoding region, this vector also contains the nopaline-synthase gene terminator of *A. tumefaciens*, which includes the polyadenylation signal.

Example 2: Transformation of Wheat Plants and Selection of Event IND-ØØ412-7

The co-transformation method used to obtain event IND-ØØ412-7 was based on the methods developed by Barcelo and Lazzeri (1995), Pastori et al. (2001), and Rasco-Gaunt et al. (2001). These methods are also used in several research centers.

Firstly, the wheat kernels were harvested and sterilized. The kernels were collected from the spikelets and were sterilized. Then, the embryos were isolated and their axes were removed to avoid early germination. The scutella were placed in the appropriate medium, in the middle of a Petri plate, with the undamaged region of the explant facing upwards for it to experience the impact of the microparticles.

For bombardment, the gold particles covered with DNA from both plasmids of interest, pIND4-HB4 y pIND4-Bar, were boosted inside the cells of the explants using gene gun PDS-1000/He (Biolistic® PDS-1000/He Particle Delivery System, BIO-RAD).

After bombardment, the explants treated were placed in the fresh culture medium under the hormonal conditions necessary for the generation of the embryogenic calli. The selection process started three weeks later, once the embryos were already developed. The selection agent used in this case was glufosinate ammonium.

The seedlings that survived selection rounds due to the PAT expression and developed a good root system were transferred and placed in a growth chamber. At this point, samples were taken to prove the presence of bar and HaHb4 using PCR. Once the plants were developed, they were transferred to bigger pots where they were grown until harvest.

Event Selection

Transgenic plants were generated following a biolistic protocol using the British variety Cadenza. The first multiplication ($T_1$ seed) was carried in a growth chamber between August and December of 2007. Approximately 20 individuals derived from each transgenic event were sampled for a segregation test by PCR determination (Table 1).

TABLE 1

Segregation test. Lines with p-values > 0.15 were carried to next generation.

| Line | PCR Positive | PCR Negative | n | $X^2$ (3:1) | p-value |
|---|---|---|---|---|---|
| Ta.IV.ii.a.1 | 2 | 14 | 16 | 33.33 | 0.00 |
| Ta.IV.ii.a.2 | 9 | 8 | 17 | 4.41 | 0.04 |
| Ta.IV.ii.a.3 | 14 | 6 | 20 | 0.27 | 0.61 |
| Ta.IV.ii.a.4 | 12 | 7 | 19 | 1.42 | 0.23 |
| Ta.IV.ii.a.5 | 8 | 10 | 18 | 8.96 | 0.00 |
| Ta.IV.ii.a.6 | 17 | 2 | 19 | 2.12 | 0.15 |
| Ta.IV.ii.a.7 | 3 | 15 | 18 | 32.67 | 0.00 |
| Ta.IV.ii.a.8 | 7 | 11 | 18 | 12.52 | 0.00 |
| Ta.IV.ii.a.9 | 5 | 15 | 20 | 26.67 | 0.00 |
| Ta.IV.ii.a.10 | 5 | 15 | 20 | 28.12 | 0.00 |
| Ta.IV.ii.a.11 | 15 | 5 | 20 | 0.00 | 1.00 |
| Ta.IV.ii.a.12 | 14 | 4 | 18 | 0.07 | 0.79 |

Lines derived from selfings of selected events (3:1 segregation in T1) were sowed in August of 2008 under a hail shelter. Growth and development of these lines were characterized throughout the growing season (Table 2).

TABLE 2

Phenology.

| Line | 12 | 20 | 27 | 34 | 42 | 49 | 57 | 63 | 70 | 77 | 84 | 91 | 98 | 105 | 111 | 119 | 126 | 131 |
|---|---|---|---|---|---|---|---|---|---|---|---|---|---|---|---|---|---|---|
| | Days after sowing | | | | | | | | | | | | | | | | | |
| | Zadocks scale value | | | | | | | | | | | | | | | | | |
| Wild Type | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Wild Type | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.1.2 | 1.1 | 1.3 | 1.4 | 2.1 | 2.2 | 2.3 | 2.5 | 2.6 | 2.6 | 3.1 | 3.7 | 4.7 | 5.9 | 7.3 | 8.3 | 8.7 | 8.9 | 9.2 |
| Ta.IV.ii.a.1.5 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.1.12 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.3.1 | 1.1 | 1.3 | 1.4 | 2.1 | 2.2 | 2.4 | 2.5 | 2.6 | 2.6 | 3.1 | 3.7 | 4.5 | 5.9 | 7.3 | 8.3 | 8.7 | 8.9 | 9.2 |
| Ta.IV.ii.a.3.2 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.3.6 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.3.7 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.3.10 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |

TABLE 2-continued

Phenology.

| Line | Days after sowing | | | | | | | | | | | | | | | | | |
|---|---|---|---|---|---|---|---|---|---|---|---|---|---|---|---|---|---|---|
| | 12 | 20 | 27 | 34 | 42 | 49 | 57 | 63 | 70 | 77 | 84 | 91 | 98 | 105 | 111 | 119 | 126 | 131 |
| Ta.IV.ii.a.3.11 | 1.1 | 1.3 | 1.4 | 2.2 | 2.3 | 2.4 | 2.5 | 2.6 | 2.6 | 3.2 | 3.7 | 4.5 | 5.5 | 5.9 | 7.3 | 7.7 | 8.5 | 8.9 |
| Ta.IV.ii.a.3.13 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.3.14 | 1.1 | 1.3 | 1.4 | 2.2 | 2.3 | 2.4 | 2.5 | 2.6 | 2.6 | 3.2 | 3.7 | 5.5 | 5.9 | 7.3 | 8.5 | 8.7 | 8.9 | 9.2 |
| Ta.IV.ii.a.3.17 | 1.1 | 1.3 | 1.4 | 2.2 | 2.3 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.3.18 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.1 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.2 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.3 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.5 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.7 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.14 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.15 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.16 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.17 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.4.18 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.1 | 1.1 | 1.3 | 1.4 | 2.1 | 2.3 | 2.4 | 2.5 | 2.6 | 2.6 | 3.2 | 3.7 | 5.5 | 5.9 | 7.3 | 8.5 | 8.7 | 8.9 | 9.2 |
| Ta.IV.ii.a.6.2 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.3 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.4 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.5 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.6 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.7 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.8 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.9 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.11 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.12 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.13 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.14 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.15 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.6.17 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.2 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.3 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.5 | 1.1 | 1.3 | 1.4 | 2.2 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.6 | 1.1 | 1.3 | 1.4 | 2.2 | 2.2 | 2.4 | 2.5 | 2.6 | 2.6 | 3.1 | 3.7 | 4.3 | 5.9 | 7.3 | 8.3 | 8.5 | 8.7 | 8.9 |
| Ta.IV.ii.a.11.7 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.8 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.9 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.10 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.13 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.15 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.11.17 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.12.1 | 1.1 | 1.3 | 1.4 | 2.1 | 2.2 | 2.4 | 2.5 | 2.6 | 2.6 | 3.2 | 3.7 | 5.5 | 5.9 | 7.3 | 8.5 | 8.7 | 8.9 | 9.2 |
| Ta.IV.ii.a.12.3 | 1.1 | 1.3 | 1.4 | 2.1 | 2.2 | 2.4 | 2.5 | 2.6 | 2.6 | 3.2 | 3.7 | 5.5 | 5.9 | 7.3 | 8.5 | 8.7 | 8.9 | 9.2 |
| Ta.IV.ii.a.12.4 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.12.5 | 1.1 | 1.3 | 1.4 | 2.1 | 2.2 | 2.4 | 2.5 | 2.6 | 2.6 | 3.2 | 3.7 | 5.5 | 5.9 | 7.3 | 8.5 | 8.7 | 8.9 | 9.2 |
| Ta.IV.ii.a.12.6 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.12.7 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.12.8 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.12.9 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.12.11 | 1.1 | 1.3 | 1.4 | 2.1 | 2.2 | 2.4 | 2.5 | 2.6 | 2.6 | 3.2 | 3.7 | 5.5 | 5.9 | 7.3 | 8.5 | 8.7 | 8.9 | 9.2 |
| Ta.IV.ii.a.12.13 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |
| Ta.IV.ii.a.12.14 | 1.1 | 1.3 | 1.4 | 2.1 | 2.2 | 2.4 | 2.5 | 2.6 | 2.6 | 3.1 | 3.7 | 5.5 | 5.9 | 7.3 | 8.5 | 8.7 | 8.9 | 9.2 |

During the vegetative stage, plants were sampled for PCR analysis to identify homozygous lines. With three selected homozygous lines, 6 field trials were conducted during 2009 and 2011 at Monte Buey (Córdoba, 2009), Gutenberg (Córdoba, 2010), Camet (Buenos Aires, 2011), Corral de Bustos (Córdoba, 2011), Daireaux (Buenos Aires, 2011), and Villa Saboya (Buenos Aires, 2011).

Trials included three homozygous lines (events) and the wild type (parental control). Yield data were analyzed using ANOVA with a completely randomized block design at a 95% confidence level using Infostat (Di Rienzo et al., 2010). In this analysis the data were pooled among sites, and sources of variation included genotypes, environments and the genotype by environment interaction. Means were compared a posteriori with a Fisher lest significant test ($\alpha$=0.05).

Analysis of variance show statistically significant differences for the effect of genotype (p=0.0003, FIG. 4). In addition, a statistically significant genotype by environment interaction was detected ($p<0.0001$). This interaction is explained by the crossover of line Ta.IV.ii.a.4 and the control yields at one site (FIG. 4). In the combined analysis all transgenic lines presented higher yield than the parental control. Among lines, Ta.IV.ii.a.12 presented the highest mean yield at all sites. This transgenic line was selected for further characterization and was renamed with the code: IND-ØØ412-7.

Example 3: Characterization of DNA Sequences in Wheat Event IND-ØØ412-7

Due to the complex nature of the wheat genome, a strategy to reduce the background genomic information in order to elucidate the insertion structure, sequence and its flanking sequences in the wheat genome was designed. The carrier chromosome was identified using DArT technology platform (Diversity Arrays Technology, Jaccoudy et al., 2001). Once the HaHB4 carrier chromosome was identified, it was isolated applying a chromosome sorting technique (Doležel et al., 1989; JanVra'na et al., 2000; Suchánková et al., 2006; Šimková et al., 2008). The sequencing strategy to identify the insertion region of IND-ØØ412-7 in the isolated chromosome consisted of a combined NGS approach using two complementary sequencing technologies: Illumina and Pacific Biosciencies. Illumina produced high-throughput short reads of 100 bp from both sides of a 500 bp-fragment sequencing library. On the other hand, PacBio produced low-throughput single molecule reads from a 15-20 kb-fragment library.

As the size of the insert increases, the likelihood of the polymerase passing over the sequence more than once decreases. For this reason, larger sequences possess a higher error rate than smaller ones. To solve this problem, special algorithms that correct these sequences using smaller sequences obtained by Illumina have been developed. Using this algorithm, PacBio RSII sequences are corrected and a precise and reliable assembly of the sample is obtained (Koren et al., 2012).

a) Southern Blot Analysis.

The copy number of genes of interest was determined in homozygous IND-ØØ412-7 plants by Southern blot analysis.

Leaf tissue from greenhouse- or field-grown homozygous IND-ØØ412-7 plants or Cadenza plants were used for DNA isolation. One gram of leaf tissue from either IND-ØØ412-7 or Cadenza was flash frozen using liquid nitrogen and ground into fine powder using a pre-chilled pestle and mortar. DNA was extracted with Qiagen DNeasy Maxi Prep Kit following manufacturer's protocol. After elution, the DNA was precipitated by adding 1/10 volume of 3M sodium acetate and 2-3 volumes of 100% ethanol. The pellet was washed with 70% ethanol and suspended in 80 μL of 1× TE buffer. The DNA was quantified using a QuBit fluorometer. The concentration of DNA for IND-ØØ412-7 was 1100 ng/μL and that of Cadenza was 900 ng/μL.

Genomic DNA from event IND-ØØ412-7 was digested with three enzymes: HindIII, BamH1 and AseI. For each 50 μL digestion reaction, 5 μg genomic DNA was mixed with either HindIII, BamHI or AseI enzymes at concentrations of 10 U/μg of DNA. The samples were digested overnight (~16 hours) at 37° C. For digests of the control plasmid, 100-200 picograms of plasmid DNA were used.

The restriction digests of IND-ØØ412-7 and Cadenza genomic DNA were loaded into a 0.7% agarose gel along with DIG labeled Molecular Weight Marker VII (Roche Cat No. 1669940910). The samples were run at 50 V overnight. The gel was incubated in denaturing buffer twice for 30 minutes each time. The denatured gel was washed in transfer buffer for 15 minutes prior to alkaline transfer (outlined below).

There is one HindIII site in the pIND-4 plasmid, located very close to 5' prUBI-1 extreme. No other HindIII site was present in the plasmids (FIG. 1). Assuming the occurrence of a single, intact inserts containing the sequence of interest in the genome of IND-ØØ412-7, the minimum fragment size of hybridization of the HaHB4 probe would be 2.842 kbp and that of the bar probe would be 2.860 kbp.

Additionally, there is one BamHI site in the pIND-4 plasmid, located very close to initiation codon of HaHB4 and bar CDSs. No other BamHI sites are present in the plasmids (FIG. 1). Again, assuming the occurrence of a single, intact inserts containing the sequence of interest in the genome of IND-ØØ412-7, the minimum fragment size of hybridization of the HaHB4 probe would be 825 bp and that of the bar probe would be 843 bp.

Finally, there are five AseI restriction sites in the plasmid (FIG. 1), two within of the sequence of interest, in the UBI-1 intron, and three in the vector, two close to the end of Tnos and the other inside of bla gene. Complete AseI digestion in the insert should release a DNA segment of 1.313 kbp long that contains the binding target for the HaHB4 probe. The bar probe will detect a DNA fragment of 1.331 kbp. This consideration is assuming a single intact insertion.

Molecular probes for HaHB4 and bar CDSs were synthesized following the procedure outlined in the Roche PCR DIG Probe Synthesis Kit (Cat. No. 11636090910) and using oligonucleotides mentioned in Table 3.

TABLE 3

List of primers used for the preparation of the probes used in Southern blot analyses.

| Probe | Size (bp) | Hybridization (° C) | Primer Type | Sequence |
|---|---|---|---|---|
| HB4 | 200 | 45 | Forward | GGGCTTCATCCTGGTCAAGTGGC |
| | | | Reverse | TCTTGATGCTTTTCTGCTACATTTCTCAGC |
| Bar | 282 | 55 | Forward | CACGCAACGCCTACGACTGGACGGCC |
| | | | Reverse | GTACCGGCAGGCTGAAGTCCAGCT |

Alkaline transfer of DNA from the agarose gel was performed using the Turboblotter-Rapid downward transfer system (Whatman). The DNA was transferred to a 12×21 cm Nylon membrane (Nytran™ Super Charge, Sigma-Aldrich Co., St. Louis, Mo.) for 4 hours. The membrane was washed in neutralizing buffer (0.2M sodium phosphate, pH 6.8). The DNA was permanently cross-linked to the membrane by Ultraviolet Cross linker (CL-1000) with 2 exposures of 1500 mJ.

The membrane was incubated in 50 mL of Roche DIG EasyHyb hybridization buffer (Cat. no. 11 603 558 001) at pre-calculated hybridization temperatures (45° C., 55° C. for bar gene and HaHB4 gene probes respectively) on an orbital shaker.

Aliquots of 35 μL and 45 μL bar and HaHB4 probes, were diluted by adding 65 and 55 μL, respectively, of 1× TE buffer. The probe solutions were incubated at 95° C. for 10 min and cooled to 4° C. for 2 min. They were added to 8.75 mL of DIG hybridization buffer and poured to the bottom of the hybridization bottle. The membranes were incubated at the described hybridization temperatures for 16 hours in a hybridization oven (VWR scientific products) with an orbital shaker.

After hybridization, the membranes were washed with washing buffer according to instructions provided with the Roche, DIG Luminescent Detection Kit. After 1 hour of blocking with 1× blocking reagent, the membranes were incubated for 30 min in a solution containing 50 mL of 1× blocking reagent and 5 μL of anti-digoxigenin-AP. The membrane was washed twice with washing buffer for 30 minutes each time and finally treated with detection buffer for 5 minutes. At this point the membrane was placed in a KPL Hybridization Bag (KPL Cat. No. 60-00-51). 5 mL of CSPD solution from the DIG Luminescent Detection Kit was applied evenly across the membrane. The membrane was incubated with CSPD solution for 5 minutes at room temperature. The hybridization bag with the membrane was heat sealed and incubated at 37° C. for 15 minutes. The hybridization bag was placed in a cassette with Kodak Biomax Light Film (Cat. No. 178 8207) in dark room and exposed for 20 minutes. The films were developed at dark using a Konika QX-60A X-ray film processor. Subsequent exposures were made at 1 hour or 2 hours as required.

The analysis of hybridization bands obtained with HaHB4 probe allowed to assume the presence of three copies of this CDS (FIG. 5).

On the other hand, the analysis of hybridization bands obtained with bar probe allowed us to assume the presence of seven copies of this CDS with BamHI (FIG. 6). However, when considering HindIII and AseI the number is lower, indicating possible internal DNA rearrangements (FIG. 6).

In brief, southern blots results showed a complex insertion pattern with possible internal DNA rearrangements, suggesting that a genomic sequencing approach should be necessary to resolve the insertion structure in IND-ØØ412-7 event.

b) Identification and Isolation of Chromosome Containing the Insertion Sequences in IND-ØØ412-7

DArT was used to identify that HaHB4 gene located in chromosome 2D of wheat genome. Each polymorphic DNA fragment (which corresponds to a point on the plate) is actually a molecular marker that may serve for the genotyping of a segregating population of a biparental cross (the presence or absence of the marker in the segregating material) and the detection of associations of these markers with characteristic of agronomic interest (region of the polymorphism). In the case of IND-ØØ412-7 event, this technology was used to genotype the F2 generation of the cross IND-ØØ412-7×Bag17, and to search for possible linkage of these markers with HaHB4 transgene. The presence or absence of HaHB4 was determined in each F2 individual and, after genotyping, associations were determined between DArT markers and HaHB4. This transgene presented association with one marker located in the 2D chromosome. The fact that only one marker presented association to HaHB4 may be because there is not saturated marker map available for this particular chromosome (Jia et al., 2013).

The HaHB4 CDS was most probable located in the long arm near the centromere associated to the marker Gpw3105.

Figure 7:
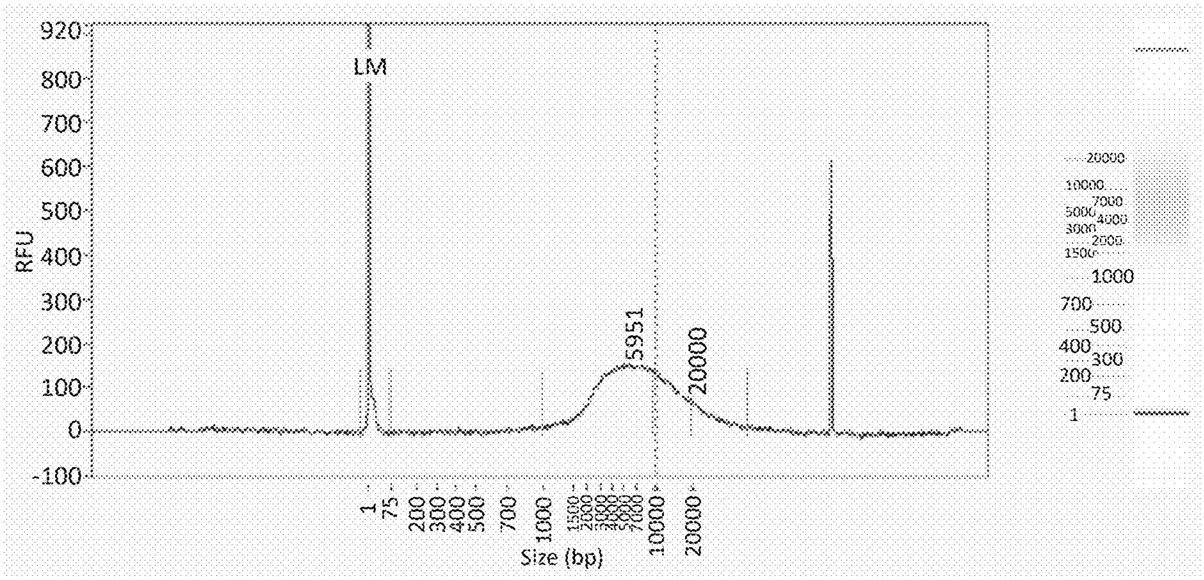
FIG. 7: Evaluation of integrity and size distribution of the DNA sample produced by chromosome 2D sorting. Average fragment size 5951 bp.

Using this information, 5 ug of chromosome 2D DNA that was suitable for Illumina library preparation were obtained. However, due to the nature of the DNA amplification process post-sorting, the DNA was partially suitable for PacBio libraries (FIG. 7).

Diversity panels were generated using DNA from the IND-ØØ412-7 and wild genotype Cadenza.

Genomic DNA was extracted from seedlings. About 5 ng DNA from each genotype was digested evaluated for 1 hour at 37° C. with 2 U of restriction enzymes (EcoRI, PstI and MspI) in a final volume of 8 μL. After digestion, 2 μL of ligation mixture were added and the sample was incubated for 3 hours at 37° C. The ligation mixture is comprised of 0.2 μL of T4 ligase (New England Biolabs), 0.2 μL of 50 mM ATP, 1.2 μL of MilliQ water (MQ) and 0.1 μL of suitable specific enzyme at a concentration of 50 pmol/μL (MspI) and 5 pmol/μL (EcoRI and PstI). After ligation, the mixture was diluted to a final volume of 500 μL using MQ water, and 2 μL was used as template in a PCR reaction. The reaction was conducted in a final volume of 50 μL, 2 U Red Taq polymerase (Sigma) and primers. After an initial incubation at 95° C. for 3 minutes, the reaction followed the following protocol: 30 cycles of 94° C. for 30 seconds, 60° C. for 45 seconds and 72° C. for 1 minute. A final extension was performed at 72° C. for 8 minutes.

The amplicons thus generated were ligated into the PCR2.1TOPO vector (Invitrogen) and subsequently transformed by heat shock cells of *E. coli* TOP10F '(Invitrogen) following manufacturer's instructions. The transformants were selected on media containing ampicillin and X-gal. Individual white colonies (containing the recombinant plasmid) were transferred to a tube by ringing containing 20 μL of 10% glycerol. From each sample in glycerol, 5 μL aliquot was taken and was transferred to a tube containing 45 μL of PCR master mix RedTaq tube (Sigma) and 15 pmol of each primer M13 forward and M13 reverse. The profile cycler used was 1 cycle at 95° C. for 5 minutes; 35 cycles of 94° C. for 30 seconds, 52° C. for 30 seconds and 72° C. for 1 minute. After amplification, PCR products were precipitated using 1 volume of isopropanol at room temperature and washed with 100 μL of 70% ethanol. The ethanol was removed and the products were dried at room temperature.

The products were re-suspended in MQ water, 3×SSC or 1×SSC+0.01% sarkosyl (Sigma) at a final concentration of ~20 ng/uL. The purified fragments were transferred to a 384-well plate (Genetix) and 6 replicates were set for passage in Polysine™ chips (Menzel Glazer) using the Affymetrix™ 417 System. After 1 day of fixation, the chips were processed according to the published procedure (2001) with the slight modification that sodium borohydride was used (Sigma) instead of using succinic anhydride and 1-methyl-2-pyrrolidone as blocking solution, prepared in PBS buffer pH 7.4 (137 mM NaCl, 2.7 mM KCl, 10 mM NaHPO, KHHPO 2 mM). The chips were immersed in boiling water for 30 seconds to denature the DNA and then immediately immersed in iced 100% ethanol for 10 seconds. The chips were dried at room temperature.

After PCR amplification, the products were purified using columns (Qiagen) or precipitated by addition of isopropanol to remove excess dNTPs. The Cy3 and Cy5 (Pharmacia) fluorescent dyes were incorporated using labeling kit Decarandom-prime DNA (Fermentas) according to the manufacturer's instructions.

The samples labeled with Cy3 and Cy5 (5 μL of each) dyes were mixed with 2 μL of a solution of 20 ug/uL DNA from herring sperm (Sigma) dissolved in Express Hybridization solution (Clontech) and denatured at 96° C. for 3 minutes. The denatured probes were mixed with 10 to 15 μL of hybridization solution, transferred directly to the surface of the microarray, and covered with a glass (24×24 mm, Mediglass). The chips were immediately placed in a humidification chamber at 65° C. overnight for hybridization. After hybridization, the chips were washed with 1×SSC with 0.1% SDS for 5 min, 1×SSC for 2 minutes, 0.2×SSC for 2 minutes and 20 seconds 0.02×SSC.

The chips were scanned using the Affymetrix 418™ scanner. The intensity of each signal was analyzed using the Scanalyse v.2.44 (Standford University) and GenePix Pro v.3 (Axon instruments) program.

c) Junction Sequence Analysis and Structure of the Insertion in IND-ØØ412-7 Using Illumina and PacBio Sequencing.

Results from Southern blot analysis suggested a complex pattern of transgenic insertion. Therefore, isolated chromosome 2D DNA library was sequenced using Illumina Hiseq platform. We produced more than 1.2 billion reads in 2×100 bp paired-end configuration representing more than 124 Gb of sequencing data. Sequencing coverage of the whole chromosome was estimated between 40 and 50× based on not redundant mappable reads on single copy genes located in chromosome 2D such as PpoD1b (He et al, 2009). Sample enrichment in chromosome 2D was verified by mapping reads to known single copy genes located outside the chromosome such LOXs (Feng et al., 2012). In these cases, coverage was estimated between 1 and 5×, thereby confirming a highly enriched DNA in chromosome 2D sequences.

Read mapping on plasmids used for transformation allowed us to verify the Southern blot results. It was concluded that we had obtained 3 complete or nearly complete copies of HaHB4 CDS based on 100× coverage and 8 complete or nearly complete copies of bar CDS based on 400× coverage.

Several other plasmid elements were identified with coverage up to 1200×.

Junction Sequence Analysis (JSA) protocol (Kovalic et al., 2012) using Illumina reads identified up to 4 different flanking sequences with wheat DNA and several chimeric junction sequences involving plasmid elements. In brief, Illumina data also showed a complex pattern of the insertion event involving internal plasmid rearrangements in IND-ØØ412-7.

Consequently, PacBio long sequencing reads to assist the scaffolding process of the Illumina reads assembly were generated. PacBio long reads would allow reading through complex internal structures and rearrangements.

Figure 8:
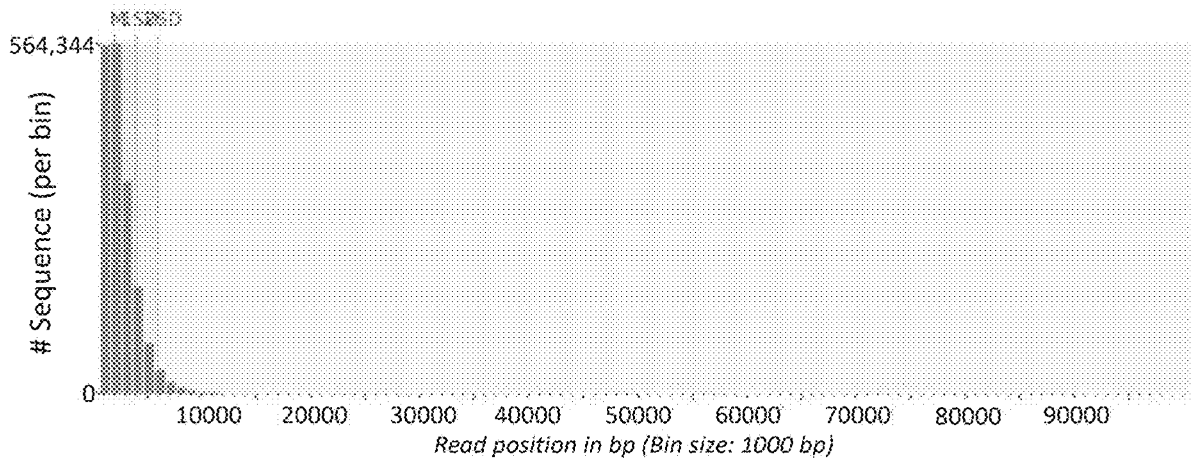
FIG. 8: PacBio read length distribution. Histogram representing absolute frequency (number of reads) in intervals of 1000 bp read length.

Due to the DNA sample quality obtained after chromosome sorting which allow us to generate a library of around 5 Kb average size, the P4-C2 chemistry of PacBio was used. This chemistry produces an average of 5.5 Kb long reads. 20 SMART cells to generate 1,806,197 reads totaling 3.5 Gb of sequencing data with an average read length of approximately 2 Kb and a maximum of 13 Kb were used. Based on a chromosome 2D size of 800 Mb, a coverage of 4.7× of the whole chromosome was estimated. PacBio statistics are shown in Table 4 and read length distribution and Q scores shown in FIG. 8 and FIG. 9.

TABLE 4

PacBio Statistics.

| | |
|---|---|
| Library average size | 5500 bp |
| # smart cells: | 20 |
| # Sequences | 1,806,197 |
| Total bases | 3.513.329.966 bp. (3, 5 Gb.) |
| Mean sequence length | 1.943,32 ± 1.605,46 |
| Minimum length | 50 bp |
| Maximum length | 32,913 |

Based on a combined analysis of sequencing data from Illumina and PacBio the flanking sequences of the insertion were firstly defined.

A set of four parameters as a cut-off to determine the true identity of a flanking sequence was established:

1. Supported by Illumina data,
2. Supported by PacBio data,
3. Supported by Illumina coverage as a single copy, and
4. Supported by PCR amplification from IND-ØØ412-7 DNA.

Four different flanking sequences passed all filters to meet the selected criteria named JPLa, JPLb, JPSa and JPSb.

A similar approach was used to determine all of the internal chimeric plasmid-plasmid junction sequences but considering the Illumina coverage for the individual plasmid elements involved. Internal junction sequences that passed all filters were extended using Illumina data and mapped on the long PacBio reads to produce a final assembly. The quality of the final assembly was checked back to the initial southern blot data and the results were confirmed.

Figure 10:
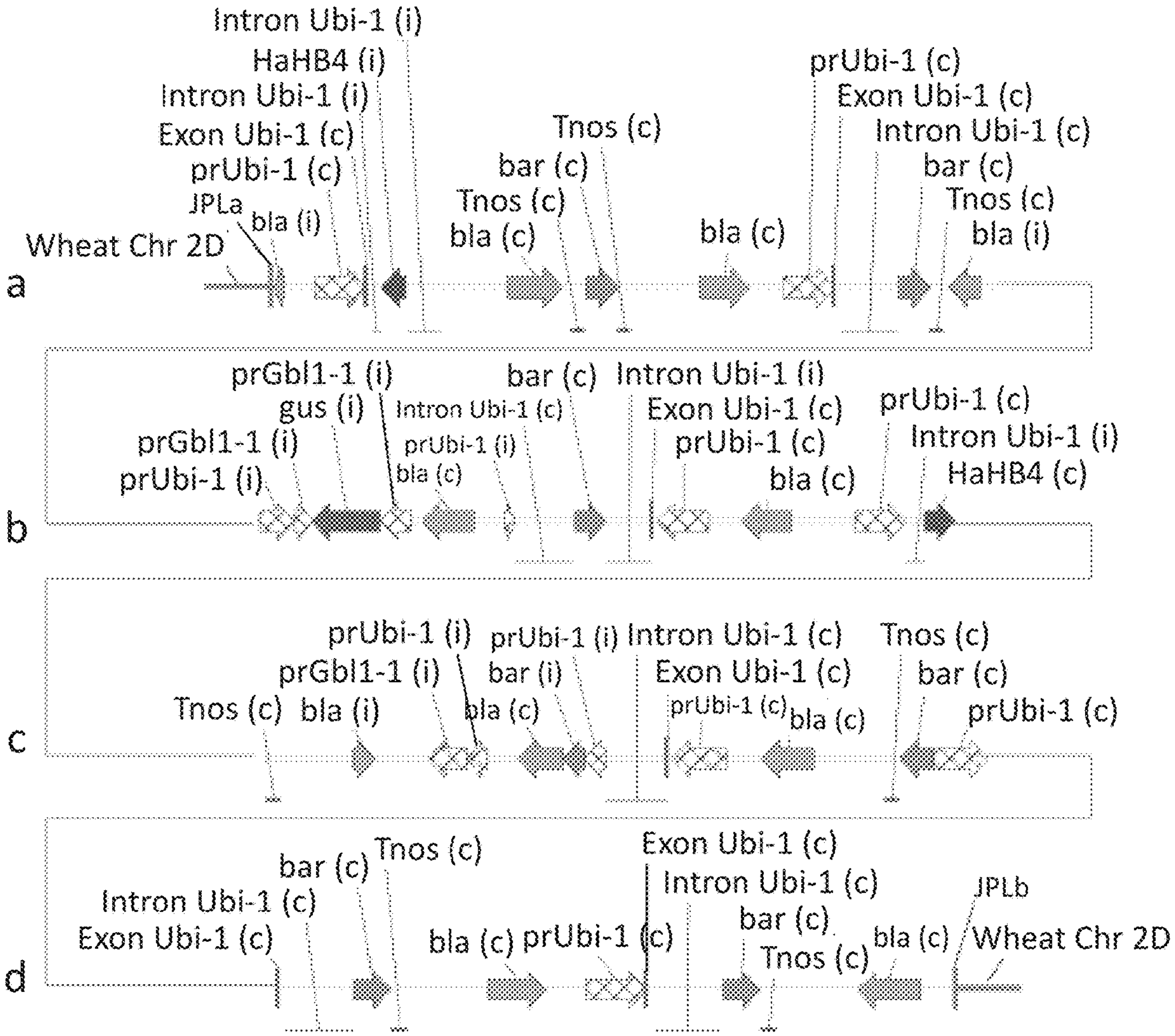
FIG. 10: DNA sequence schemes of IND-ØØ412-7 long insert containing HaHB4 (red) and bar (light blue) complete (c) and incomplete (i) coding regions. This insert is subdivided in four fragments for their better understanding. a) HaHB4 incomplete (i) coding region is located between two incomplete fragments of Ubi-1 intron. Besides there are two bar coding regions, complete (c) and incomplete (i). The bar (i) is between two Tnos region. Bar (c) is located between its regulatory elements in the correct positions. b) HaHB4 (c) coding region is located downstream of the proximal region of ubi-1 intron and the 5' promoter region and upstream its Tnos. Bar (i) is located between two intron ubi-1 regions. c) Bar (c) is located between an invert Ubi-1 promoter region and a Tnos region. Bar (i) is located between ubi-1 parcial promoter region and bla gene. d) Two bar (c) coding region are located between their complete regulatory elements.
Figure 11:
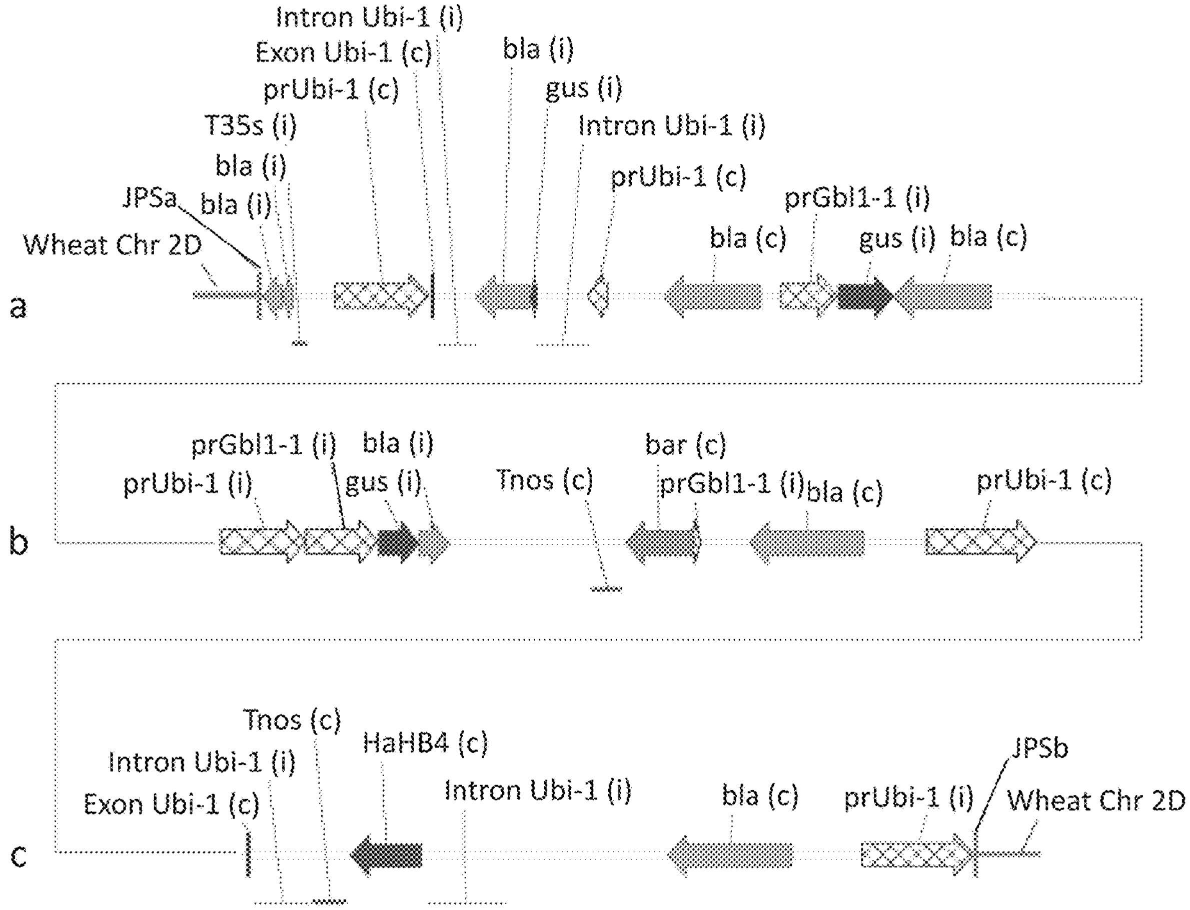
FIG. 11: DNA sequence schemes of IND-ØØ412-7 short insert containing HaHB4 and bar complete (c) coding region. This insert is subdivided in three fragments for their better understanding. b) Bar (c) is located between an invert and short sequence prGBL-1 region and a Tnos region. c) HaHB4 complete (c) coding region is located between incomplete fragment of Ubi-1 intron and Tnos.

In brief, two different insertions of the plasmids in highly repetitive regions of chromosome 2D in the wheat genome were described. One of the insertions is 47,611 bp long and the other is 20,418 bp long totaling 68,029 bp of insertions in IND-ØØ412-7 event (FIGS. 10 and 11). The insertions accounted for three copies of HaHb4 CDS, seven copies of bar CDS, 16 copies of bla gene and four copies of gus CDS. In the longer insertion, FIG. 10, it is possible to identify a complete HaHB4 coding region (red) downstream of probable functional regulatory elements (panel b). On the other hand, complete bar coding region (light blue) are observed in panels a, b, c and d. In panels (a) and (d) it is possible to identify that the regulatory elements of bar are complete and the right position. The complete copies of Bar CDSs potentially encode functional proteins. As a result, only one HaHB4 copy and one bar copy without complete regulatory elements were identified.

d) Detection, Structure and Copy Number of Vector Sequences not Related to the Genes of Interest.

From the analysis of the insertion events it was evident the presence of plasmid vector sequences and other coding regions unrelated to the genes and regulatory regions of interest introduced during the wheat transformation process.

Elements of plasmid backbone detected in the insertion of the IND-ØØ412-7 are bla gene conferring ampicillin resistance in bacteria, and bacterial origin of replication of pBR322 plasmid (FIGS. 10 and 11). Regarding bla, it is important to mention that it has no regulatory elements for expression in the wheat as well as none of the described bla copies have been positioned near eukaryotic regulatory elements.

All of the plasmid backbone sequences in IND-ØØ412-7 insertion have a confirmed origin in the vectors pIND4-HB4 and pIND4-Bar used for transformation as demonstrated by the identity of the nucleotide sequences using blast.

However, sequences corresponding to the gus gene (Jefferson et al., 1987) and the promoter of the wheat gbl1 gene (Jones, 2005) leading its expression were detected. These sequences originated in a third plasmid used to monitor the efficiency of transformation; nevertheless, these elements have been incorporated during the integration process. The gus CDS was found in four copies while the gbl1 promoter was found in five copies (FIGS. 10 and 11). This third plasmid would be also a derivative of the series used to incorporated HaHB4 and bar to wheat.

e) Localization of IND-ØØ412-7 Insertion in the Wheat Genome.

The insertions were located in the wheat chromosome 2D. These insertions were detected in no annotated sequences and it is highly unlikely that they were interrupting coding sequences for the reasons explained below.

All of the flanking wheat sequences corresponded to DNA segments with high similarity to retrotransposons indicating insertion events in highly repetitive DNA regions (Mayer et al, 2014).

Figure 12:
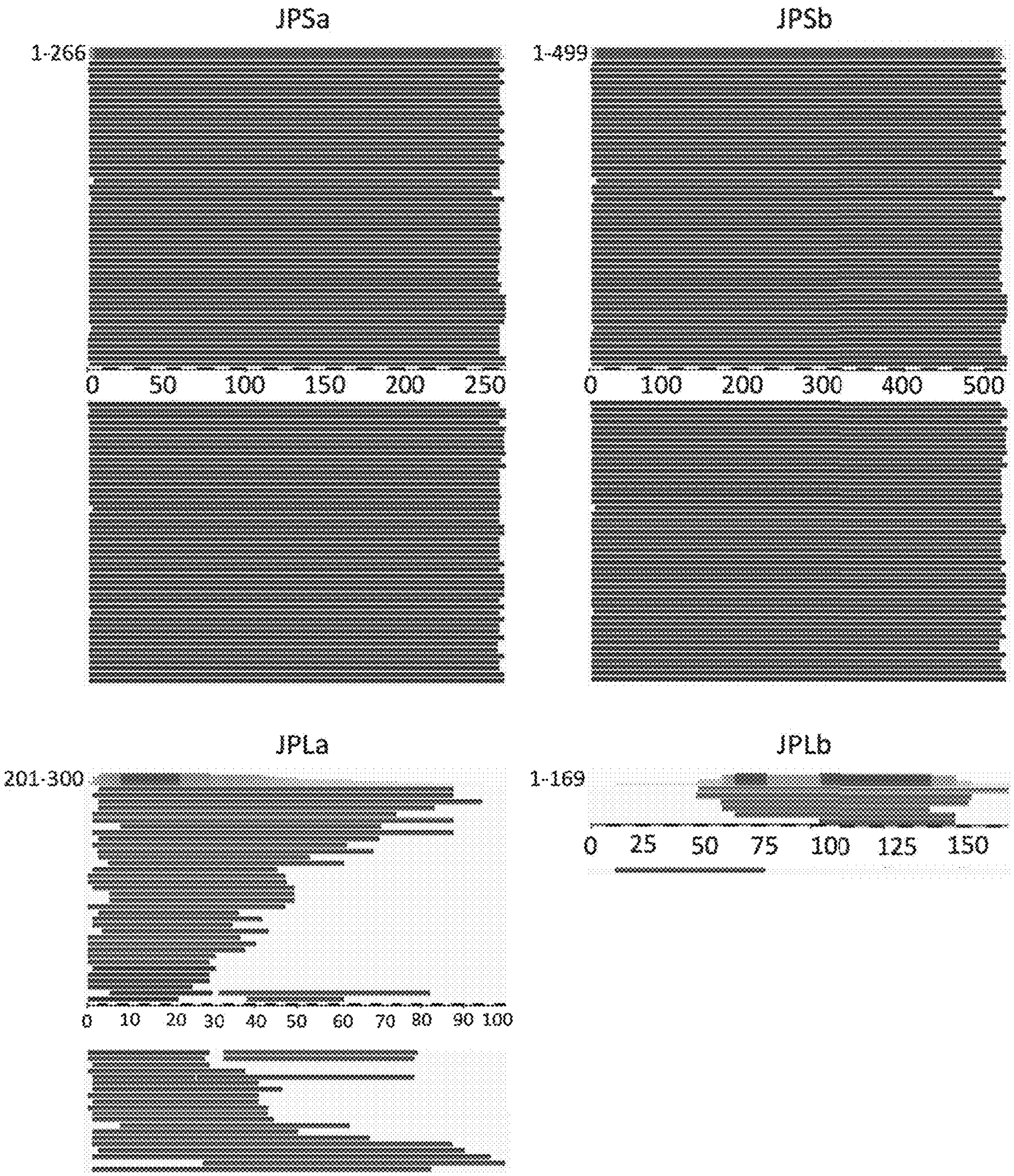
FIG. 12: Coverage amongst JPs blasted against *T. aestivum*.

To confirm this, JPs (Junction points) were blasted against IWGSC project database through EnsemblPlants website. Multiple hits against multiple *T. aestivum* chromosome sites were observed in each case. Although uneven in some cases, full sequence coverage was observed for each JP (FIG. 12). Because this IWGSC project is still in development, another blast was performed against all remaining sequenced cereals genomes present at EnsemblPlants database (*Triticum urartu, Aegilops tauschii* y *Hordeum vulgare*), resulting in the same multiple hit pattern against multiple chromosome sites. Sequences that are present in multiple chromosome sites and conserved in different organisms tend to be repetitive sequences.

JP sequences were also blasted against NCBI non-redundant database. Two of these sequences (JP Short, JPSa and JPSb) matched against known retrotransposon elements (Table 5). While the other two JP sequences (JP Long, JPLa and JPLb) had no significant hits against the NCBI database, they are highly conserved and repeated multiple times across multiple chromosomes in the wheat database, strongly suggesting unknown repeated DNA elements.

TABLE 5

| Best hit example of JP sequences blast against NCBI non-redundant database | | | | | | | | | | |
|---|---|---|---|---|---|---|---|---|---|---|
| Query | | | Subject | | | | Stats | | | |
| Name | Start | End | Name | Start | End | Notes | Score | E-val | % ID | L. |
| JPSa | 1 | 266 | FN564434 | 122244 | 122509 | Retrotransposon gypsy | 386 | 1E−92 | 89 | 266 |
| JPSb | 1 | 499 | AF326781 | 144816 | 145314 | Transposon gypsy-like retrotransposon Fatima | 582 | 7E−146 | 83 | 499 |
| JPLa | 201 | 300 | IWGSC_CSS_ 5AS scaff_1551050 | 364 | 463 | unknown repeat element | 500 | 4E−15 | 100 | 100 |
| JPLb | 1 | 169 | IWGSC_CSS_ 5DS scaff_2755707 | 2630 | 2797 | unknown repeat element | 507 | 2E−15 | 81 | 174 |

L.: Length

Stability and Integrity of the IND-ØØ412-7 Insertions Inserts Segregation Over Sexual Transfer.

Homozygous plants for the insertion IND-ØØ412-7 were crossed with a commercial variety, Baguette 17, to obtain the F1 generation. After the selfing of F1 plants, 349 F2 seeds were obtained. Plants grown from these seeds were used for segregation analysis. DNA was extracted from young leaves. Prior to DNA extraction, leaf tissue was frozen in liquid nitrogen and processed to a fine powder in a mortar with a pestle or in tubes in a "96 mill" for minipreps. The following techniques were used to extract plant DNA, depending on the amounts of DNA needed for experimental purposes:

CTAB Method:

Genomic DNA was extracted following a Hexadecyltrimethylammonium bromide (CTAB)-based method. Briefly, 600 μL of CTAB buffer (2% w/v CTAB, 100 mM TrisHCl, 20 mM EDTA, 1.4 M NaCl, and β-mercaptoethanol) and 5 μg RNase A were added to approximately 100 mg of ground leaf tissue and incubated at 55-60° C. for 15-20 minutes with intermittent mixing. 600 μL of chloroform was added to the samples and mixed by hand 2-3 minutes, then centrifuged at 10,000 rpm for 8 minutes. The upper aqueous phase was put into a clean microtube and the DNA was precipitated with 400 μL of isopropanol. The sample was centrifuged at 12,500 rpm for 10 minutes to pellet the precipitated DNA. The DNA pellets were washed with 300 μL of 70% ethanol by centrifuging the samples at 12,500 rpm for 5 minutes. The DNA pellets were air-dried, then resuspended in 100 μL of TE buffer (10 mM TrisHCl, 1 mM EDTA, pH 8.0). All extracted DNA was stored in a 4° C. refrigerator or in a −20° C. freezer.

To ensure the integrity of the samples, end point PCR of a wheat endogenous control was performed with a specific primer. Then, end point PCR was performed using different combinations of primers to determine the presence of HaHB4 and bar CDS. A Chi-square ($\chi 2$) analysis was used to evaluate the expected 3:1 segregation (presence or absence of CDSs of interest).

Table 6 summarizes the results obtained by PCR analysis.

TABLE 6

| Results of segregation analysis by means of PCR. | | | | |
|---|---|---|---|---|
| Total | HaHB4+bar+ | HaHB4+bar− | HaHB4−bar+ | HaHB4−bar− |
| 349 | 259 | 0 | 0 | 90 |

Total: number of individuals tested;
HaHB4+bar+: number of individuals positive to HaHB4 and bar CDSs;
bar−HaHB4+: number of individuals positive to HaHB4 CDS;
HaHB4−bar+: number of individuals positive to bar CDS;
HaHB4−bar−: number of individuals negative to HaHB4 and bar CDSs.

Table 7 shows the statistical analysis:

TABLE 7

| Statistical analysis of segregation results. | | | | | |
|---|---|---|---|---|---|
| Expected results (No. of plants) | | Observed results (No. of plants) | | | |
| + | − | + | − | $X^2$ | p-value |
| 261.75 | 87.25 | 259 | 90 | 0.11 | 0.74 |

The value of $\chi 2$ (degrees of freedom=1, $\alpha$=0.05) showed no statistically significant difference between the expected and observed results indicating a Mendelian segregation 3:1 for each of the CDSs analyzed (HaHB4 and bar).

The results obtained in the F2 generation indicate that both transgenes are stably inherited during sexual transfer. In the segregating population, both genes had a 3:1 segregation according to the Mendelian principles. Finally, even though both CDSs come from a process of co-transformation by bombardment, the two genes are linked, as each individual F2 analyzed presents the same results for both CDSs, bar and HaHB4.

The previous analysis was made with oligonucleotides that detect almost the entire CDSs.

After confirmation of the stability of the complete CDSs of bar and HaHB4, it was decided to proceed with the characterization the other genetic elements, or part of them, and flanking sequences. With the aim of detecting the presence/absence of HaHB4, bar and bla transgenes copies in IND-ØØ412-7, oligonucleotides that hybridize with all copies (complete and incomplete) were designed. Also, the four insert-to-plant junctions were detected to determine their segregation in the F2 generation. These studies were made in 92 individuals of the F2 population. The results are shown in Table 8.

TABLE 8

| Statistical analysis of segregation results. | | | | | |
|---|---|---|---|---|---|
| Expected results (No. of plants) | | Observed results (No. of plants) | | | |
| + | − | + | − | $X^2$ | p-value |
| 69 | 23 | 65 | 27 | 0.9275 | 0.336 |

The χ2 value (d.f.=1, α=0.05) in the F2 generation indicated no statistically significant difference between the observed and the expected 3:1 segregation ratio for the data analyzed.

All transgenic plants analyzed presented consistent results for the three elements of IND-ØØ412-7 detected (HaHB4, bar and bla) and for the four insert-to-plant junctions (JPSa, JPSb, JPLa and JPLb). These results support the conclusion that the IND-ØØ412-7 construct resides at a single locus within the wheat genome and is inherited according to Mendelian inheritance principles.

Example 4: Yield Increase as an Indicator of Abiotic Stress Tolerance

Fifteen field trials were conducted at multiple test sites and planting dates to evaluate yield and yield components of transgenic event IND-ØØ412-7 and the parental non-transgenic control line (cv Cadenza). Sites were located within the major wheat production areas of Argentina, ranged between latitude 32° S and 38° S. The area covers diverse environmental conditions of Argentinean wheat crop production. Trials included representative locations from pampa's wheat regions described by Kugler and Godoy (1974): IIN (7 trials), IIS (6 trials) and IV (two trials). At each site the planting date was adjusted according to farmers' usual practice, starting in May/June at northern sites and in July at southern sites. Planting and harvest dates are reported in Table 9.

TABLE 9

Selected locations for field trials and dates of planting and harvest.

| Site ID | Site location | Province | Wheat region | Planting date | Harvest date |
|---|---|---|---|---|---|
| A12-1 | Monte Buey | Córdoba | IIN | May 31, 2012 | Dec. 26, 2012 |
| A12-2 | Monte Buey | Córdoba | IIN | Jun. 19, 2012 | Dec. 26, 2012 |
| A13 | Monte Buey | Córdoba | IIN | Jun. 14, 2013 | Dec. 12, 2013 |
| D12 | Corral de Bustos | Córdoba | IIN | May 30, 2012 | Dec. 12, 2012 |
| D13 | Corral de Bustos | Córdoba | IIN | Jun. 17, 2013 | Dec. 17, 2013 |
| F12 | Villa Saboya | Buenos Aires | IIS | Jun. 7, 2012 | Dec. 22, 2012 |
| F13 | Villa Saboya | Buenos Aires | IIS | Jun. 26, 2013 | Dec. 12, 2013 |
| G12-1 | Carmen de Areco | Buenos Aires | IIS | Jun. 14, 2012 | Jan. 4, 2013 |
| G12-2 | Carmen de Areco | Buenos Aires | IIS | Jul. 6, 2012 | Jan. 4, 2013 |
| H12 | Daireaux | Buenos Aires | IIS | Jun. 12, 2012 | Dec. 28, 2012 |
| H13 | Daireaux | Buenos Aires | IIS | Jun. 27, 2013 | Dec. 19, 2013 |
| I12 | Balcarce | Buenos Aires | IV | Jul. 25, 2012 | Jan. 7, 2013 |
| I13 | Balcarce | Buenos Aires | IV | Jul. 26, 2013 | Jan. 13, 2014 |
| P12 | Landeta | Santa Fe | IIN | Jun. 3, 2012 | —[a] |
| P13 | Landeta | Santa Fe | IIN | Jun. 10, 2013 | Dec. 11, 2013 |

[a]Trial lost by flood at maturity

Weather conditions were registered during the growing season for each site. Annual rainfall registered across sites ranged from 424 mm to 1497 mm for trials H13 and G12 respectively (Table 10), indicating a wide weather variation across sites and years. During 2013 rainfall accumulated during the growing period (June-December) registered values under 500 mm for all sites. Trials planted in 2013 had higher probability of drought stress conditions than the trials planted in 2012. For 2012 rainfall values were above 500 mm for the same period at all sites (Table 10).

TABLE 10

Weather data (rainfall) for each site during 2012 and 2013 for the wheat field sites.

| | Site ID [a] | | | | | | | | | | | | |
|---|---|---|---|---|---|---|---|---|---|---|---|---|---|
| Month | A12 | A13 | D12 | D13 | F12 | F13 | G12 | H12 | H13 | I12 | I13 | P12 | P13 |
| January | 47 | 36 | 103 | 25 | 110 | 0 | 75.5 | 112 | 32 | 46 | 69 | 98 | 17 |
| February | 214 | 87 | 282 | 159 | 227 | 5 | 211 | 111 | 10 | 66 | 33 | 164 | 106 |
| March | 212 | 68 | 211 | 42.9 | 104 | 96 | 166 | 184 | 46 | 78 | 98 | 211 | 55 |
| April | 9 | 106 | 19 | 83 | 105 | 30 | 57 | 33 | 70 | 46 | 45 | 83 | 112 |
| May | 48 | 44 | 49 | 33 | 56 | 31 | 120 | 166 | 17.5 | 85 | 10 | 44 | 35 |
| June | 0 | 16 | 0 | 24.5 | 0 | 0 | 7 | 0 | 6 | 0 | 23 | 2 | 17 |
| July | 0 | 12 | 0 | 13.5 | 0 | 8 | 11 | 0 | 45 | 0 | 50 | 0 | 5 |
| August | 68 | 0 | 56 | 0 | 48 | 0 | 203 | 135 | 3 | 295 | 17 | 87 | 0 |
| September | 135 | 2.5 | 132 | 4.5 | 55 | 15 | 72.5 | 70 | 36 | 42 | 141 | 115 | 16 |
| October | 321 | 162 | 291 | 126 | 245 | 58 | 285 | 252 | 37.5 | 27 | 50.5 | 236 | 33 |
| November | 73 | 131 | 155 | 184 | 165 | 150 | 98 | 87 | 111 | 77 | 183 | 64 | 294 |
| December | 128 | 97 | 156 | 24.1 | 41 | 54 | 191 | 179 | 11 | 150 | 10 | 314 | 0 |
| June-December [b] | 725 | 421 | 790 | 377 | 554 | 285 | 868 | 723 | 250 | 591 | 452 | 818 | 365 |
| Year | 1255 | 762 | 1453 | 720 | 1156 | 447 | 1497 | 1328 | 425 | 912 | 730 | 1418 | 690 |

[a] A12 = Monte Buey, two planting dates, year 2012; A13 = Monte Buey, year 2013; D12 = Corral de Bustos, year 2012; D13 = Corral de Bustos, year 2013; F12 = Villa Saboya, year 2012; F13 = Villa Saboya, year 2013; G12 = Carmen de Areco, two planting dates, year 2012; H12 = Daireaux, year 2012; H13 = Daireaux, year 2013; I12 = Balcarce, year 2012; I13 = Balcarce, year 2013; P12 = Landeta, year 2012; P13 = Landeta, year 2013.

[b] Growing period

Field trials were established at each site following a completely randomized block design. Four replications were evaluated at all locations. Plots consisted of seven rows spaced 0.2 m apart and five meters in length. All field trials were bordered with plots of 7 rows and 5 meters' length. Prior to planting, seed pool of IND-ØØ412-7 and Cadenza were tested by PCR to confirm presence and absence of Hahb4 respectively. All seeds were treated with insecticide (Thiamethoxam, 0.4 mL $kg^{-1}$), and fungicide (Difenoconazole, 0.2 mL $kg^{-1}$ and Metalaxyl-M, 0.15 mL $kg^{-1}$) using the protocol indicated on the corresponding product label.

All chemicals applied to crop were performed according to farmer's usual practice. Herbicides applied during fall prior to planting consisted of Gliphosate (2.0 L $ha^{-1}$) and Metsulfuron-metil (6.8 g $ha^{-1}$). Fungicide was applied to control foliar fungal diseases at trials P12, D12, A12-1, A12-2, F12, H12, G12-1, G12-2 and I12. Fungicide was sprayed once at each trial when 50% of the plots reached the growth stage 5.1 (Zadoks, 1974). An insecticide spray to control stink bugs (*Nezara* sp., *Piezodorus* sp. and *Dichelops* sp.) was applied at Zadoks growth stage 3.1 on trials A12-1, A12-2, D12, F12, P12. Conversely, trials P13, D13, A13, F13, H13 and 113 were grown without fungicide or insecticide spray due to low pressure of diseases and pests. Fertilizers and chemicals applied at each trial are described in Table 11.

TABLE 11

Fertilization and chemical inputs for pest control at each trial

| Site ID | Chemical | Growth Stage[a] | Rate | Units | Purpose |
|---|---|---|---|---|---|
| A12-1 | Monoammonium phosphate[b] | GS 0 | 160 | kg $ha^{-1}$ | Fertilizer |
| | Urea[c] | GS 2.4 | 150 | kg $ha^{-1}$ | Fertilizer |
| | Cypermethrin 25 EC | GS 3.1 | 25 | g $ha^{-1}$ | Insecticide |
| | Azoxystrobin + Cyproconazole (Amistar Xtra ® 28 SC) | GS 5.1 | 0.5 | l $ha^{-1}$ | Fungicide |
| A12-2 | Monoammonium phosphate | GS 0 | 160 | kg $ha^{-1}$ | Fertilizer |
| | Urea | GS 2.3 | 150 | kg $ha^{-1}$ | Fertilizer |
| | Cypermethrin 25 EC | GS 3.1 | 25 | g $ha^{-1}$ | Insecticide |
| | Azoxystrobin + Cyproconazole (Amistar Xtra ® 28 SC) | GS 5.1 | 0.5 | l $ha^{-1}$ | Fungicide |
| A13 | Monoammonium phosphate | GS 0 | 160 | kg $ha^{-1}$ | Fertilizer |
| | Urea | GS 0 | 150 | kg $ha^{-1}$ | Fertilizer |
| | Urea | GS 2.6 | 150 | kg $ha^{-1}$ | Fertilizer |
| D12 | Monoammonium phosphate | GS 0 | 160 | kg $ha^{-1}$ | Fertilizer |
| | Urea | GS 2.3 | 150 | kg $ha^{-1}$ | Fertilizer |
| | Cypermethrin 25 EC | GS 3.1 | 25 | g $ha^{-1}$ | Insecticide |
| | Azoxystrobin + Cyproconazole (Amistar Xtra ® 28 SC) | GS 5.1 | 0.5 | l $ha^{-1}$ | Fungicide |
| D13 | Monoammonium phosphate | GS 0 | 160 | kg $ha^{-1}$ | Fertilizer |
| | Urea | GS 0 | 150 | kg $ha^{-1}$ | Fertilizer |
| | Urea | GS 2.6 | 150 | kg $ha^{-1}$ | Fertilizer |
| F12 | Monoammonium phosphate | GS 0 | 160 | kg $ha^{-1}$ | Fertilizer |
| | Urea | GS 2.3 | 150 | kg $ha^{-1}$ | Fertilizer |
| | Cypermethrin 25 EC | GS 3.1 | 25 | g $ha^{-1}$ | Insecticide |
| | Azoxystrobin + Cyproconazole (Amistar Xtra ® 28 SC) | GS 5.1 | 0.5 | l $ha^{-1}$ | Fungicide |

TABLE 11-continued

Fertilization and chemical inputs for pest control at each trial

| Site ID | Chemical | Growth Stage[a] | Rate | Units | Purpose |
|---|---|---|---|---|---|
| F13 | Monoammonium phosphate | GS 0 | 160 | kg $ha^{-1}$ | Fertilizer |
| | Urea | GS 0 | 150 | kg $ha^{-1}$ | Fertilizer |
| | Urea | GS 2.6 | 150 | kg $ha^{-1}$ | Fertilizer |

[a]GS: Zadoks Scale (Zadoks, 1974)

[b]Equivalent Grade 11-52-0

[b]Equivalent Grade 46-0-0

Note:

Dose in the table corresponds to the commercial product

TABLE 11

Fertilization and chemical inputs for pest control at each trial. Continued.

| Site ID | Chemical | Growth Stage[a] | Rate | Units | Purpose |
|---|---|---|---|---|---|
| G12-1 | Monoammonium phosphate | GS 0 | 160 | kg $ha^{-1}$ | Fertilizer |
| | Urea | GS 2.3 | 150 | kg $ha^{-1}$ | Fertilizer |
| | Azoxystrobin + Cyproconazole (Amistar Xtra ® 28 SC) | GS 5.1 | 0.5 | l $ha^{-1}$ | Fungicide |
| G12-2 | Monoammonium phosphate | GS 0 | 160 | kg $ha^{-1}$ | Fertilizer |
| | Urea | GS 2.3 | 150 | kg $ha^{-1}$ | Fertilizer |
| | Azoxystrobin + Cyproconazole (Amistar Xtra ® 28 SC) | GS 5.1 | 0.5 | l $ha^{-1}$ | Fungicide |
| H12 | Monoammonium phosphate | GS 0 | 160 | kg $ha^{-1}$ | Fertilizer |
| | Urea | GS 3.1 | 300 | kg $ha^{-1}$ | Fertilizer |
| | Azoxystrobin + Cyproconazole (Amistar Xtra ® 28 SC) | GS 5.1 | 0.5 | l $ha^{-1}$ | Fungicide |
| H13 | Monoammonium phosphate | GS 0 | 160 | kg $ha^{-1}$ | Fertilizer |
| | Urea | GS 0 | 150 | kg $ha^{-1}$ | Fertilizer |
| | Urea | GS 2.6 | 150 | kg $ha^{-1}$ | Fertilizer |
| I12 | Monoammonium phosphate | GS 0 | 160 | kg $ha^{-1}$ | Fertilizer |
| | Urea | GS 2.3 | 150 | kg $ha^{-1}$ | Fertilizer |
| | Azoxystrobin + Cyproconazole (Amistar Xtra ® 28 SC) | GS 5.1 | 0.5 | l $ha^{-1}$ | Fungicide |
| I13 | Monoammonium phosphate | GS 0 | 160 | kg $ha^{-1}$ | Fertilizer |
| | Urea | GS 0 | 150 | kg $ha^{-1}$ | Fertilizer |
| | Urea | GS 2.6 | 150 | kg $ha^{-1}$ | Fertilizer |
| P12 | Monoammonium phosphate | GS 0 | 160 | kg $ha^{-1}$ | Fertilizer |
| | Urea | GS 2.3 | 150 | kg $ha^{-1}$ | Fertilizer |
| | Cypermethrin 25 EC | GS 3.1 | 25 | g $ha^{-1}$ | Insecticide |
| | Azoxystrobin + Cyproconazole (Amistar Xtra ® 28 SC) | GS 5.1 | 0.5 | l $ha^{-1}$ | Fungicide |
| P13 | Monoammonium phosphate | GS 0 | 160 | kg $ha^{-1}$ | Fertilizer |
| | Urea | GS 0 | 150 | kg $ha^{-1}$ | Fertilizer |

Agronomic data were assessed at each field trial. The agronomic variables consisted of early stand (NPL), number of spikes $m^{-2}$ (NE), number of kernels by $spike^{-1}$ (NGE), thousand kernel weight (PMG), test weight (PH), yield (REND), aerial biomass (BMA) and harvest index (IC).

Early stand was assessed by counting emerged plants in a central plot area of 0.6 $m^2$ before tillering. NE, BMA, weight of grains (PG), PMG and IC were assessed at harvest on a central plot sample of 0.6 $m^2$. PMG was assessed on a sample of 10 g of the grains harvested at each plot. The NGE was calculated according to:

$$NGE=(PG/NE)\times 1000/PMG \qquad \text{Eq. [1]}$$

PH was assessed with the Argentinean standard protocol used for wheat commercialization (Shopper's grain scale). Yield was assessed on the five central rows of each plot for trials A12-1, A12-2, D12, F12 and H12. In the rest of the trials, yield was assessed on the whole plot (7 rows). Yield was corrected by grain moisture (13.5%) and expressed as kg $ha^{-1}$.

Data of the transgenic event and the control Cadenza were analyzed using ANOVA with a completely randomized block design at a 95% confidence level using Infostat (Di Rienzo et al., 2010). Comparisons between the transgenic event and Cadenza were performed in a combined site analysis for REND, PMG, PH, NPL, NE, NGE, BMA and IC. In this analysis the data were pooled among sites, and sources of variation included genotypes (transgenic and control), environments and the genotype by environment interaction.

In the combined site analysis, three statistically significant differences were detected out of 8 comparisons between IND-ØØ412-7 and the control (Table 12). A statistically significant difference was detected between IND-ØØ412-7 and the conventional control for REND (p=0.0103), PMG (p=0.0039) and PH (p=0.0430). In addition, no statistically significant trial by genotype interaction was detected.

The REND of IND-ØØ412-7 was 133 kg $ha^{-1}$ higher than the control, which represents an average yield increase of 5%. Conversely, PMG and PH showed lower values in IND-ØØ412-7 compared with the control. No consistent differences were observed in cycle or biotic stress response between the event and the parental control. Overall, significant differences in yield between IND-ØØ412-7 and the control suggests that the transgenic event set more seeds per unit land area. Smaller seed size might occur due to lower source-to-sink ratio during seed filling that also leads to lower PH. Differences between IND-ØØ412-7 and the control represented 5% and 2% for PMG and PH respectively.

TABLE 12

Comparison between IND-ØØ412-7 and the parental control Cadenza in a combined site analysis of yield and yield components.

| | | Mean (MSE) [b] | | | | |
|---|---|---|---|---|---|---|
| Variable [a] | Unit | IND-ØØ412-7 | | Cadenza | | |
| NPL | Plants $m^{-2}$ | 225 | (6.7) | 221 | (6.7) | |
| NE | Spikes $m^{-2}$ | 412 | (11.1) | 410 | (9.7) | |
| NGE | Kernels $spike^{-1}$ | 21.7 | (0.8) | 21.8 | (0.7) | |
| PMG | g | 28.3 | (0.8) | 29.7 | (0.7) | * |
| PH | kg $hl^{-1}$ | 63.7 | (1.1) | 64.8 | (1.0) | * |
| YIELD | kg $ha^{-1}$ | 2641 | (163) | 2508 | (156) | * |
| BMA | kg $ha^{-1}$ | 10583 | (743) | 10081 | (750) | |
| IC | — | 0.31 | (0.01) | 0.31 | (0.01) | |

[a] NPL = plants $m^2$; NE = spikes $m^2$; NG = kernels $spike^{-1}$; PH = test weight; PMG = thousand kernel weight; REND = yield; BMA = aerial biomass; IC = harvest index. n = 60 for NPL; n = 56 for PMG, PH and REND; n = 52 for NG and NE; n = 24 for BMA and IC.

[b] SE: standard error of the mean

* Statistically significant differences ($\alpha$ = 0.05) between control Cadenza and event IND-ØØ412-7

Having especially described and determined the nature of the present invention and having explained how to implement it, we claim the exclusive property right on:

1. A recombinant DNA molecule comprising the sequences of SEQ ID NO: 7, 8, 9 and 10.

2. A non-living plant material comprising the recombinant DNA molecule according to claim 1.

* * * * *